(12) United States Patent
Geiger et al.

(10) Patent No.: US 8,481,278 B2
(45) Date of Patent: Jul. 9, 2013

(54) APPARATUS AND METHODS FOR ANALYZING FLUID VARIABLES

(75) Inventors: Timothy Robert Geiger, Louisville, CO (US); Dean Michael Kingston, Arvada, CO (US); Steven Patrick Tyrrell, Erie, CO (US); Christopher Paul Mattison, Longmont, CO (US); Barry Patrick Vant-Hull, Boulder, CO (US)

(73) Assignee: Lyzer Diagnostics, Inc., Boulder, CO (US)

( * ) Notice: Subject to any disclaimer, the term of this patent is extended or adjusted under 35 U.S.C. 154(b) by 545 days.

(21) Appl. No.: 12/732,109

(22) Filed: Mar. 25, 2010

(65) Prior Publication Data
US 2010/0267065 A1 Oct. 21, 2010

Related U.S. Application Data

(60) Provisional application No. 61/163,044, filed on Mar. 25, 2009, provisional application No. 61/163,046, filed on Mar. 25, 2009, provisional application No. 61/163,048, filed on Mar. 25, 2009, provisional application No. 61/163,050, filed on Mar. 25, 2009, provisional application No. 61/163,053, filed on Mar. 25, 2009, provisional application No. 61/222,311, filed on Jul. 1, 2009, provisional application No. 61/226,058, filed on Jul. 16, 2009, provisional application No. 61/231,508, filed on Aug. 5, 2009.

(51) Int. Cl.
*C12Q 1/56* (2006.01)
(52) U.S. Cl.
CPC ........................................ *C12Q 1/56* (2013.01)
USPC ........................................................... 435/13
(58) Field of Classification Search
None
See application file for complete search history.

(56) References Cited

U.S. PATENT DOCUMENTS

| | | |
|---|---|---|
| 6,440,725 B1 | 8/2002 | Pourahmadi et al. |
| 2002/0098526 A1 | 7/2002 | Bamdad |
| 2004/0043479 A1 | 3/2004 | Briscoe et al. |
| 2005/0009101 A1 | 1/2005 | Blackburn |
| 2007/0243630 A1 | 10/2007 | Boehringer et al. |

FOREIGN PATENT DOCUMENTS

WO WO 2008025945 A1 * 3/2008

OTHER PUBLICATIONS

Bell et al. (1954) *Nature* 174:880-881.
Eckmann et al. (2000) *Anesth. Analg.* 91:539.

(Continued)

*Primary Examiner* — Jon P Weber
*Assistant Examiner* — Robert Yamasaki
(74) *Attorney, Agent, or Firm* — Peter B. Scull; Hamilton, DeSanctis & Cha, LLP

(57) ABSTRACT

Methods and devices for analyzing fluid variables such as viscosity, surface tension, analyte concentration, and the presence of particulates or aggregates are provided. The devices analyze fluid variables by measuring cessation of fluid flow through the medium or a change in flow rate due to an inherent property of the fluid variable, or due to a modification of the fluid variable as the fluid migrates through the medium. The lateral flow devices measure relative rates of capillary flow down converging arms of a common element of porous media in which at least one of the arms has been modified by the addition of flow-modifying agents which affect the flow rate in response to the concentration of the analyte. The fluid fronts will converge at a position determined by their relative flow rates, which is thus indicative of a fluid variable, such as analyte concentration, in the sample fluid.

7 Claims, 13 Drawing Sheets

OTHER PUBLICATIONS

Figure 1A:
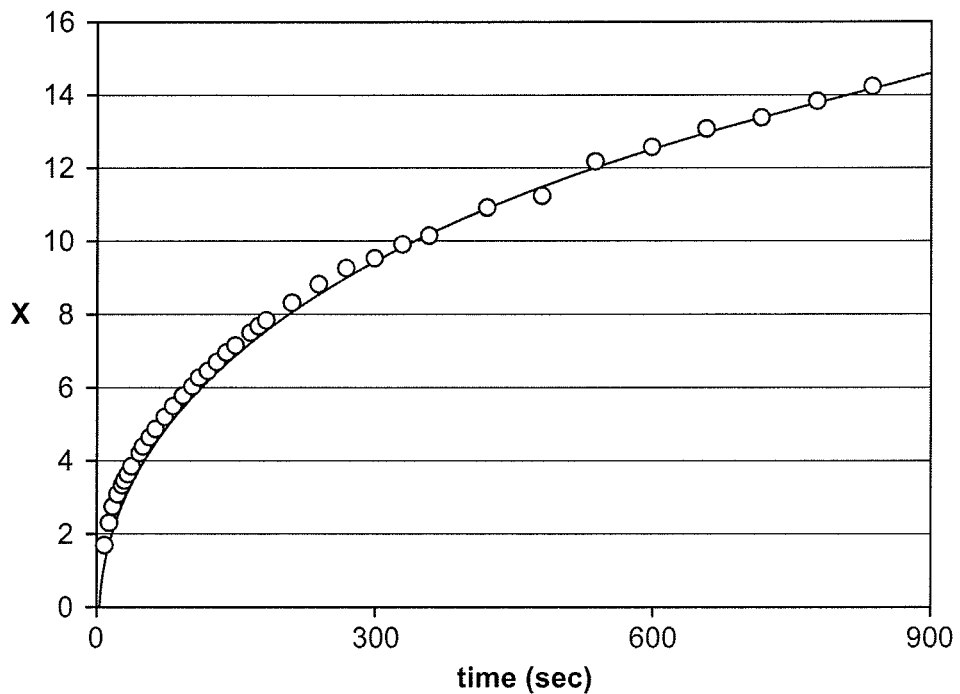

Juszczak and Fortuna (2003) EJPAU vol. 6, No. 11; www.ejpau.media.pl/volume6/issue2/food/art-11.html.
King (2010) themedicalbiochemistrypage.org/blood-coagulation.html#clinical.
Moriarty et al. (2005) *Curr. Opin. Cardiol.* 20:318-323.
Pries et al. (1992) *Am. J Physiol.* 96:562.
Qian et al. (2003) "A mathematical model of lateral flow bioreactions applied to sandwich assays". *Analytical Biochemistry.* 322:89-98.
Rafai et al. (2010) *Phys. Rev. Lett.* 104:098102.
Sokolov and Aranson (2009) *Phys. Rev. Lett.* 103:148101.
Washburn EW (1921). "The dynamics of capillary flow." *The Physical Review* 17(3):273-283.

* cited by examiner

APPARATUS AND METHODS FOR ANALYZING FLUID VARIABLES

RELATED APPLICATIONS

This application claims priority under 35 U.S.C. §119(e) to U.S. Provisional Application Ser. No. 61/163,044 entitled "A LATERAL FLOW DEVICE UTILIZING COMPETING FLOW RATES FOR QUANTITATIVE ANALYSIS" filed Mar. 25, 2009, and also to U.S. Provisional Application Ser. No. 61/163,046 entitled "A LATERAL FLOW DEVICE UTILIZING COMPETING FLOW RATES FOR QUANTITATIVE ANALYSIS WITHOUT SAMPLE METERING" filed Mar. 25, 2009, and also to U.S. Provisional Application Ser. No. 61/163,048 entitled "A LATERAL FLOW DEVICE UTILIZING COMPETING FLOW RATES MODIFIED BY CHEMICAL PRECIPITATION FOR QUANTITATIVE ANALYSIS WITHOUT SAMPLE METERING" filed Mar. 25, 2009, and also to U.S. Provisional Application Ser. No. 61/163,050 entitled "A LATERAL FLOW DEVICE UTILIZING COMPETING FLOW RATES MODIFIED BY IMMUNOCHEMICALLY MODIFIED BEADS FOR QUANTITATIVE ANALYSIS WITHOUT SAMPLE METERING" filed Mar. 25, 2009, and also to U.S. Provisional Application Ser. No. 61/163,053 entitled "A LATERAL FLOW DEVICE UTILIZING COMPETING FLOW RATES TO [sic] COAGULATION FUNCTION" filed Mar. 25, 2009, and also to U.S. Provisional Application Ser. No. 61/222,311 entitled "A LATERAL FLOW DEVICE UTILIZING COMPETING FLOW RATES MODIFIED BY IMMUNOCHEMICALLY MODIFIED MICROPARTICLES FOR QUANTITATIVE OR QUALITATIVE ANALYSIS WITHOUT SAMPLE METERING" filed Jul. 1, 2009, and also to U.S. Provisional Application Ser. No. 61/226,058 entitled "A LATERAL FLOW DEVICE UTILIZING CESSATION OF CAPILLARY FLOW RATES FOR QUALITATIVE ANALYSIS" filed Jul. 16, 2009, and also to U.S. Provisional Application Ser. No. 61/231,508 entitled "A LATERAL FLOW DEVICE UTILIZING COMPETING FLOW RATES MODIFIED BY CHANGES IN VISCOSITY FOR QUANTITATIVE ANALYSIS WITHOUT SAMPLE METERING" filed Aug. 5, 2009. The subject matter of the provisional application is incorporated in its entirety by reference herein. This application also is related to International PCT Application No. PCT/US2010/28732 filed on the same day herewith. The subject matter of the PCT application is incorporated by reference herein.

FIELD OF THE INVENTION

Devices and methods for assessing variables of a fluid through analysis of the migration characteristics of a fluid, such as flow rate and migration distance of the fluid front, through a medium. In one embodiment, the methods and devices provided herein measure clotting time of blood or plasma by analyzing migration of the blood or plasma in a porous medium. In other embodiments, a method and apparatus for measuring analytes in fluid samples by measuring the rate of capillary flow and/or migration of a fluid front through porous media is provided. The devices provided herein could be used for measuring coagulation rates, immunochemical testing, analyzing blood chemistry components such as glucose or cholesterol, monitoring for infectious diseases, or many other fluid concentration measurement uses.

BACKGROUND

Lateral-flow immunoassay tests have been in wide use since their introduction in the mid-1980's [Rosen]. The device format has proven to be very popular due to its flexibility, low cost, ease and speed of use, and rapid development cycle for new assays. Lateral flow devices are usually comprised of a plastic housing and a porous test strip. The housing protects and binds the components of the test strip together, provides a controlled means for sample application to the test strip, and provides indicator markings and directions for use. The sample strip is the heart of the device, usually comprised of four separate, but overlapping strips, allowing the sample fluid to flow by capillarity from one strip, or zone, to the next [O'Farrell]. The first zone is the sample pad, which draws sample fluid into the device and may perform treatments (filtration, buffering, etc.) necessary for the assay to function. The second zone is the conjugation pad, containing certain dried components for the assay. In the case of sandwich-type immunoassays, these components will usually be the detection part of the sandwich—monoclonal antibodies specific for the analyte that are conjugated to a detection agent, such as an enzyme, or colored latex microbeads. These components are solubilized by the sample fluid, and available for reaction. The next zone is the reaction matrix, containing components of the assay necessary for reading a result, usually immobilized in well-defined detection zones for easy readout as visible indicator lines. In the case of sandwich-type immunoassays, these components would usually be polyclonal antibodies specific to the analyte. The last zone is the wick, which soaks up excess sample fluid and keeps fluid flowing through the rest of the sample strip until the reaction reaches completion.

These assays can also use enzyme-mediated reporter formats. One example of this can be demonstrated by an assay to measure glucose in a sample fluid. Enzymes glucose oxidase and horseradish peroxidase can be bound to a region of a test strip. The sample can be mixed in a known ratio with a substrate such as 3,3'-Diaminobenzidine (DAB) and the sample applied to the test strip. As the sample migrates toward and through the region with the immobilized enzymes, the glucose contained within the sample will react with the glucose oxidase producing hydrogen peroxide and d-Gluconic Acid. In turn, the hydrogen peroxide and the DAB will react with the horseradish peroxidase to produce an insoluble brown-black precipitate which will be visible as an indicator line.

The above assays can also be run in competitive formats, useful when there may be high concentrations of analyte in the sample fluid, or cases when sandwich assays are not feasible, such as small molecule analytes. In one example of this strategy, polyclonal antibodies specific to the analyte would be immobilized at the indicator lines. The conjugate pad would include latex beads coated with analyte. In the absence of analyte, the beads would bind at the indicator lines as the sample flows through to produce a readable signal. In the presence of high concentrations of analyte in the sample fluid, the analyte would compete for the immobilized antibodies in the detection zone with the analyte bound to the beads, producing a much reduced signal.

The assays described above depend on an accumulation of reporter molecule at a specific point on the test strip to form indicator lines. The flow rate of the sample fluid through the detection zone in effect determines the incubation time, and thus determines the minimum reaction constants that the antibodies must have [Brown]. Too high of an analyte concentration in the sample can actually lead to a drop-off in signal by as much as two orders of magnitude, as the sample saturates both the capture and indicator antibodies without forming sandwiches, a phenomenon known as "sensor poisoning" [Qian]. Optimal conditions depend on many factors, including flow rate, and therefore much design time is spent trying to minimize the effect of varying flow rate.

In contrast, the devices described herein rely on changes in flow rate and/or measurement of a fluid front as an analytical tool.

SUMMARY

The methods and devices provided herein are characterized by a variety of component ingredients, steps of preparation, and biophysical, physical, biochemical or chemical parameters. As would be apparent to those of skill in the art, the devices and methods provided herein include any and all permutations and combinations of the ingredients, steps and/or parameters described below.

Provided herein are methods for analyzing or assessing variables of a fluid by measuring the movement of a fluid front through a medium or by measuring flow rate. The medium can be porous, such as glass fiber filters or nitrocellulose, non-porous, such as glass, or a mixture of porous and non-porous materials. Also provided are devices for measuring the movement of a fluid front through a medium, assessing migration characteristics such as flow rate or migration distance, and using the migration characteristics to analyze a fluid variable. The fluid variable can be a property that is a characteristic of a fluid, such as viscosity or surface tension, or it can be a property of a component or analyte that is present in the fluid as a suspension or in solution, e.g., the amount, concentration or extent of binding/aggregation/complexation of the component or analyte. Processes such as the formation of gels, meshes or aggregates that can impede the flow of a fluid through a medium can be analyzed using the methods and devices provided herein. The fluid variable can directly be measured as a function of flow rate of the fluid or migration distance in a medium, or it can be analyzed indirectly by its interaction with a flow modifying agent.

In a "stopped flow" method, the fluid variable can be analyzed by cessation of the flow of the fluid through the medium, either due to the presence of flow-impeding components in the fluid or due to the addition of flow-modifying agents. The migration distance of the fluid front relative to the proximal or distal end of the medium can be used to analyze the fluid variable, such as analyte amount/concentration or viscosity of the fluid. In a "split flow" method, migration of the fluid front is simultaneously effected through two divergent, parallel or opposing paths in the medium. One path contains a flow-modifying agent that impedes flow rate or migration of the fluid front, while the other path does not. The relative migration distances of the fluid front through each of the paths can then be used to analyze the fluid variable of interest. In an "arc flow" method, the fluid front migrates along two convergent paths that form a closed circuit; one containing a flow-modifying agent and the other free of the agent. The point of convergence on the closed circuit provides a measure of the fluid variable of interest.

The methods and devices provided herein can analyze fluid variables in fluids such as blood, milk, water, solutions containing biological molecules such as proteins and nucleic acids, and biological fluids other than blood such as plasma, serum, urine, saliva, seminal fluid, lavages, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof. The methods and devices provided herein are designed to be employed at the point of care, such as in the home, in hospital emergency rooms or operating rooms, hospital laboratories and other clinical laboratories, doctor's offices, in the field, or in any situation in which a rapid and accurate result without the use of a cumbersome, expensive device is desired. In some embodiments, the device provided herein is disposable. In further embodiments, the device is made of laminated plastic sheets and paper, thereby providing significant cost savings over other devices containing injection-molded or cast parts.

Provided herein are methods for analyzing the chemical composition of a liquid sample using a porous medium, or several elements of porous media in serial contact with one another, treated to allow capillary flow of desired sample fluid through these media wherein the media contain a means for introducing sample fluid at a position in the porous media whereby the sample fluid may move by capillary flow along one or more separate paths. The one or more of separate paths, or the sample, are treated in a fashion that causes a cessation of flow, or a reduction of flow to an extent that for the purposes of this method it may be treated as a cessation of flow, of the liquid sample, such cessation in flow being dependent on the presence of a specific component or components in the liquid sample at or above certain threshold levels. The medium can be in a device that includes a means for measuring the positions of the liquid front in the porous media along each path compared with the position at which the sample was introduced, thereby monitoring whether flow has ceased along each path thereby determining whether the components are present at or above the aforesaid threshold levels. In some embodiments, the agents that cause the cessation of flow are pre-mixed with the sample fluid before being introduced to the element of porous media. In other embodiments, the agents that cause the cessation of flow are present in a region of the porous media through which the sample fluid flows. In yet other embodiments, the treatment of at least one of the possible liquid paths leads to a change in viscosity, thus leading to cessation of the flow rate. In some embodiments, treatment of at least one of the possible liquid paths leads to the formation of a polymeric gel or mesh, thus leading to cessation of the flow rate. The treatment can include micro-particles that are introduced into the fluid to enhance the flow-restriction properties of the polymeric gel or mesh. In some embodiments, the micro-particles are coated or conjugated with binding agents specific for components that are to be measured in the sample fluid. In yet other embodiments, the treatment of at least one of the possible liquid paths leads to the formation of an insoluble precipitate, thereby changing the permeability of the media and leading to cessation of the flow rate. In further embodiments, immunochemical principles are used to either cause the concentration, or agglomeration of latex microspheres or similar agents, thereby changing the permeability of the media and thus leading to cessation of the flow rate.

Also provided are methods for analyzing the chemical composition of a liquid sample using an element of porous media treated to allow capillary flow of desired sample fluid through this media; and a means for introducing sample fluid at a position in this porous media whereby the sample fluid may move by capillary flow along two or more separate paths. Treatment of one or more of these separate paths in a fashion that causes a change in flow rate of the liquid sample compared to an untreated path, such change in flow rate is dependent on the presence of a specific component or components in the liquid sample. The device used to perform the method includes a means for measuring the positions of the liquid front in the porous media along each path compared with the position at which the sample was introduced, thereby making a comparison of the relative flow rates along each path. Also provided is a method to relate this comparison of flow rates to the chemical composition of the sample. In some embodiments, the volume of the liquid sample is known, and only two paths are possible, so that only the measurement of the position of one of the liquid fronts is necessary. In other embodiments, treatment of at least one of the possible liquid paths leads to a change in viscosity, thus modifying the flow rate. In yet other embodiments, the treatment of at least one of the possible liquid paths leads to the formation of an insoluble precipitate, thereby changing the permeability of the media and modifying the flow rate. In further embodiments, immunochemical principles are used to either cause the concentration, or agglomeration of latex microspheres or similar agents, thereby changing the permeability of the media and modifying the flow rate.

Also provided are methods for analyzing the chemical composition of a liquid sample that use an element of porous media treated to allow capillary flow of desired sample fluid through this media, and a means for introducing sample fluid at a single position in this porous media whereby the sample fluid may move by capillary flow along two or more separate paths, where these paths converge at a common point or points. Treatment of one or more of these separate paths in a fashion causes a change in flow rate of the liquid sample compared to an untreated path, such change in flow rate being dependent on the presence of a specific component or components in the liquid sample which causes the capture or aggregation of polymers which have been modified immunochemically. The sample fluid is permitted to move by capillary action along each of these paths simultaneously, until the fluid fronts converge, effectively ending all movement of the fluid and thereby defining an endpoint to the assay. The position at which the fluid fronts converge is used to determine relative flow rates along each of the paths, and this comparison is related to the chemical composition of the sample. In some embodiments, the treatment of one of the separate paths includes the use of micro-particles which have been modified immunochemically in addition to the polymers which have been modified immunochemically. In other embodiments, treatment of one of the separate paths includes the use of micro-particles which have not been modified immunochemically in addition to the polymers which have been modified immunochemically. In yet other embodiments, the sample is introduced simultaneously at two or more points, thereby defining the separate paths. In some embodiments, the sample purportedly containing an analyte is mixed with polymers immunochemically modified with an antibody specific to this analyte, and optionally with micro-particles coated with antibody specific to this analyte, and the treated area has immobilized antibody also specific to this analyte, so that the polymers or micro-particles will collect in a confined region, affecting flow rate.

Also provided is a method for analyzing the chemical composition of a liquid sample that uses an element of porous media treated to allow capillary flow of desired sample fluid through this media, and a means for introducing sample fluid at a single position in this porous media whereby the sample fluid may move by capillary flow along a defined path. The defined path is treated in a fashion that causes a change in flow rate of the liquid sample, such change in flow rate being dependent on the presence of a specific component or components in the liquid sample which causes the capture or aggregation of polymers which have been modified immunochemically, or a combination of polymers and micro-particles which have been modified immunochemically. The sample fluid is allowed to move by capillary action along the defined path until the formation of a mesh or gel by the immunochemically-modified polymer stops all apparent movement of the fluid, thereby defining an endpoint to the assay. The position at which the fluid front ceases motion is correlated to the chemical composition of the sample. In some embodiments, the micro-particles are not immunochemically modified.

Also provided are methods for analyzing the chemical composition of a liquid sample using an element of porous media treated to allow capillary flow of desired sample fluid through this media; and a means for introducing sample fluid at a single position in this porous media whereby the sample fluid may move by capillary flow along two or more separate paths, where these paths converge at a common point or points. One or more of these separate paths is treated in a fashion that causes a change in flow rate of the liquid sample compared to an untreated path, such change in flow rate being dependent on the presence of a specific component or components in the liquid sample. The sample fluid is allowed to move by capillary action along each of these paths simultaneously, until the fluid fronts converge, effectively ending all movement of the fluid and thereby defining an endpoint to the assay. The position at which the fluid fronts converged to determine relative flow rates along each of the paths is then determined and correlated to the chemical composition of the sample. In some embodiments, the sample is introduced simultaneously at two or more points.

Also provided are methods for analyzing the chemical composition of a liquid sample using an element of porous media treated to allow capillary flow of desired sample fluid through this media, and a means for introducing sample fluid at a single position in this porous media whereby the sample fluid may move by capillary flow along two or more separate paths, where these paths converge at a common point or points. One or more of these separate paths can be treated in a fashion that causes a change in flow rate of the liquid sample compared to an untreated path by inducing chemical precipitation in response to the presence of a specific component or components in the liquid sample. The sample fluid is allowed to move by capillary action along each of these paths simultaneously, until the fluid fronts converge, effectively ending all movement of the fluid and thereby defining an endpoint to the assay. The position at which the fluid fronts converge is analyzed to determine relative flow rates along each of the paths, and relating this comparison to the chemical composition of the sample. In some embodiments, the sample is introduced simultaneously at two or more points. In other embodiments, the sample can contain glucose and is premixed with DAB, and the treated path contains glucose oxidase and horseradish peroxidase, thereby forming an insoluble precipitate that modifies flow. In other embodiments, the sample can contain an analyte of interest, and the sample is premixed with glucose, DAB, and an antibody to the analyte which is conjugated with horseradish peroxidase, and the treated path contains glucose oxidase and a second, non-competing antibody to the analyte, thereby forming an immune-complex sandwich at the detection area in which an insoluble precipitate which modifies flow.

Also provided are methods for analyzing the chemical composition of a liquid sample using an element of porous media treated to allow capillary flow of desired sample fluid through this media, and a means for introducing sample fluid at a single position in this porous media whereby the sample fluid may move by capillary flow along two or more separate paths, where these paths converge at a common point or points. One or more of these separate paths can be treated in a fashion that causes a change in flow rate of the liquid sample compared to an untreated path, such change in flow rate being dependent on the presence of a specific component or components in the liquid sample which causes the capture or agglutination of micro-particles which have been modified immunochemically. The sample fluid is allowed to move by capillary action along each of these paths simultaneously, until the fluid fronts converge, effectively ending all movement of the fluid and thereby defining an endpoint to the assay. The position at which the fluid fronts converge can be analyzed to determine relative flow rates along each of the paths, and this comparison can be related to the chemical composition of the sample. In some embodiments, the sample is introduced simultaneously at two or more points. In other embodiments, sample containing a specific analyte is mixed with micro-particles coated with antibody specific to this analyte, and the treated area has immobilized antibody also specific to this analyte, so that the micro-particles will collect in a confined region, affecting flow rate. In other embodiments, the treated area contains micro-particles coated with polyclonal antibodies specific to the analyte to be tested, thereby causing agglutination in the presence of the analyte, blocking pores and restricting flow.

Also provided is a method for analyzing the coagulation ability of a blood sample using an element of porous media treated to allow capillary flow of desired sample fluid through this media, and a means for introducing sample fluid at a single position in this porous media whereby the sample fluid may move by capillary flow along two or more separate paths, where these paths converge at a common point or points. One or more of these separate paths can be in a fashion that activates the coagulation pathway, thereby increasing the viscosity, which in turn can lead to a change in flow rate. The sample fluid can be allowed to move by capillary action along each of these paths simultaneously, until the fluid fronts converge, effectively ending all movement of the fluid and thereby defining an endpoint to the assay. The position at which the fluid fronts converge can be analyzed to determine relative flow rates along each of the paths, and this comparison is correlated to the coagulation time of the sample. In some embodiments, the sample is introduced simultaneously at two or more points.

Also provided is a method for analyzing the coagulation ability of a blood sample using an element of porous media treated to allow capillary flow of desired sample fluid through this media and a means for introducing sample fluid at a single position in this porous media, whereby the sample fluid may move by capillary flow along two or more separate paths, where these paths converge at a common point or points. One or more of these separate paths can be treated in a fashion that activates the coagulation pathway, thereby increasing the viscosity and leading to a change in flow rate. The sample fluid can be allowed to move by capillary action along each of these paths simultaneously until the fluid fronts converge, effectively ending all movement of the fluid and thereby defining an endpoint to the assay. The position at which the fluid fronts converge can be analyzed to determine relative flow rates along each of the paths, and this comparison correlated to the coagulation time of the sample. In some embodiments, the sample is introduced simultaneously at two or more points. In other embodiments, micro-particles, of size significantly smaller than the pore-size of the porous media, can be introduced into the sample fluid in order to enhance the effect coagulation has on the difference in capillary flow rate between the two or more separate paths. In further embodiments, the micro-particles are only introduced along the path which has been treated to promote coagulation. In yet other embodiments, the micro-particles, of size significantly smaller than the pore-size of the porous media, can be introduced into the sample fluid in order to enhance the effect coagulation has on the difference in capillary flow rate between the two or more separate paths.

Also provided is a lateral flow device that measures the concentration of specific analytes in a sample by detecting changes in the rate of the capillary flow of the sample fluid through porous media such as filter paper. In particular, sample fluid containing analyte flows by capillarity down two or more converging arms of a common element of porous media, in which at least one of the arms has been modified by the addition of flow-modifying agents which affect the flow rate in response to the concentration of the analyte. The fluid fronts will converge at a position determined by their relative flow rates, which is thus indicative of the concentration of analyte in the sample fluid.

Another lateral flow device provided herein measures the concentration of specific analytes in a sample by detecting changes in the rate of the capillary flow of the sample fluid through porous media such as filter paper. In particular, sample fluid containing analyte flows by capillarity down two or more arms of a common element of porous media, in which at least one of the arms has been modified by the addition of flow-modifying agents which affect the flow rate in response to the concentration of the analyte. The relative distance at completion of the fluid fronts from the sample introduction point is determined by their relative flow rates, which is thus indicative of the concentration of analyte in the sample fluid.

Other lateral flow devices provided herein qualitatively measure the concentration of specific analytes in a sample by detecting changes in the rate of the capillary flow of the sample fluid through porous media such as filter paper. In particular, sample fluid containing one or more analytes flows by capillarity along a path through an element of porous media, or through multiple elements of porous media which are in serial contact with each other, in which the sample and/or the fluid path has been modified by the addition of flow-modifying agents which cause flow to stop in the presence of the specific analytes. If the properties of the fluid or the media do not change with time, then it is expected that the position of the fluid front will be directly proportional to the square root of time [Washburn], so that a sufficient quantity of sample fluid will saturate the porous media if given sufficient time. If the fluid front has not moved at least a specified distance after a specified period of time, this indicates that capillary flow has ceased, thereby indicating that a threshold concentration of analyte exists in the sample fluid.

One example of flow-modifying agents would be a set of enzymes and substrates that in the presence of the analyte form a precipitate that blocks the pores of the media, thus restricting flow. Another example would be latex microspheres suspended in the sample fluid and having diameters significantly smaller than the pore size of the porous media, which through commonly used immunochemistry methods would be made to congregate in certain zones of the porous media as the sample fluid flowed through these zones, thereby restricting flow. Yet another example of flow-modifying agents would be agents which change the viscosity of the sample fluid in the presence of the specific analyte, thereby slowing flow.

One example of the use of precipitation to change flow rate can be demonstrated by an assay to measure glucose in a sample material. In this embodiment, enzymes glucose oxidase and horseradish peroxidase can be bound to a region of a test strip. The sample can be mixed in a known ratio with a substrate such as 3,3'-Diaminobenzidine (DAB) and the sample applied to the test strip. As the sample migrates toward and through the region with the immobilized enzymes, the glucose contained within the sample will react with the glucose oxidase producing hydrogen peroxide and d-Gluconic Acid. In turn, the hydrogen peroxide and the DAB will react with the horseradish peroxidase to produce an insoluble brown-black precipitate that will serve to locally decrease the pore size of the support membrane thus decreasing the local flow rate. This change in flow rate can then be measured and related directly to the quantity of glucose present in the sample. The quantity of the precipitating material is proportional to the quantity of the glucose present in the sample, thus more glucose present would result in more precipitate forming thus slowing the flow of the liquid fraction of the sample more. It is also possible to have only one of the enzymes immobilized and have the other mixed with the sample traveling through the test strip, the goal being for a precipitate to form in a localized region of the membrane thus affecting the flow rate. In addition, the process could be performed simply by mixing the substrate and the sample directly with the enzymes so that precipitate will form in a non-localized fashion but still serve to decrease the pore size of the membrane and affect flow rates. Persons skilled in the art will recognize that many other types of analysis could be performed using this process the requirements being that a precipitate can be caused to form, the quantity of this precipitate being proportional to the quantity of the analyte to be measured and that this precipitate can affect the flow rate of the liquid portion of the sample through the membrane. Other potential substrate systems include but are not limited to combining alkaline phosphatase with the commonly known substrate pair BCIP/NBT.

In yet another example, localized formation of a precipitate can be caused by antibody binding in a localized area of a test strip that a liquid sample can migrate through. In a preferred embodiment intended to measure C-Reactive Protein (CRP) in a sample, two antibodies designated a1 and a2 that can bind to a CRP molecule or molecular complex can be employed. Antibody a1 can be associated either covalently or non-covalently with an enzyme such as horseradish peroxidase. The second antibody a2 can be unmodified or modified with a molecule such as biotin. In this embodiment, a sample suspected of containing CRP can be mixed with antibody a1, glucose and a precipitating substrate such as 3,3'-Diaminobenzidine (DAB). A region of the test strip will have antibody a2 and glucose oxidase bound either specifically or non-specifically to a region distal to the point of sample application. The sample will then migrate through the prepared test strip such as a nitrocellulose or nylon membrane, CRP bound antibody a1 will be retained by binding to antibody a2 causing an increase in the localized concentration of glucose oxidase in a dose responsive manner. Membrane bound glucose oxidase will react with glucose added to the sample producing hydrogen peroxide, in turn, the hydrogen peroxide will react with the peroxidase labeled antibody a1 forming an insoluble precipitate that will affect the flow rate of the liquid fraction of the sample in a dose responsive manner. This change in flow rate can be measured to determine the concentration of CRP in the sample. It is noted that unbound antibody a1 will also cause the formation of precipitate however due to the transient nature of this antibody presence, the quantity and rate of formation will simple contribute to a reasonable constant rate of precipitate formation that will be reasonable consistent from sample to sample. Those skilled in the art will recognize that many different targets can be measured using this approach, the major requirements being that antibody binding cause the formation of a precipitate that can affect flow rate of the liquid fraction of a sample in a manner proportional to the amount of antibody binding. In addition, those skilled in the art will recognize that this system can be used in a competitive binding fashion where the presence of analyte in the sample will compete with added target analyte to cause a decrease in binding to a localized area of the test strip causing a decrease in the localized formation of a precipitate to form thus increasing the flow rate of the liquid portion of the sample in a manner inversely proportional to concentration of target in a sample. In addition, those skilled in the art will recognize that antibody a2 may be biotinylated or labeled with some other specific capture label and a specific capture moiety such as a biotin binding protein such as avidin, neutraavidin or streptavidin bound to the test strip enabling both antibodies (a1, a2) to be added to the sample and the entire complex captured, but only antibody a2 captured in a dose responsive manner. Those skilled in the art will recognize that there are many ways to capture antibodies that include but are not limited to His tag, species specific anti-antibodies, Protein A and Protein G in addition to many others. Other potential substrate systems include but are not limited to combining alkaline phosphatase with the commonly known substrate pair BCIP/NBT.

Measurement of coagulation time is one example of using viscosity to monitor the state of a sample. Coagulation describes a complex process through which blood is clotted.

Prothrombin time (PT) measures the extrinsic pathway of coagulation. Induction of this pathway requires calcium. The process can be accelerated by the introduction of thromboplastin, a saline brain extract containing tissue factor, which initiates the extrinsic pathway. This pathway proceeds through a protein cascade that eventually leads to the activation of thrombin (factor IIa), a protease that cleaves fibrinogen. Fibrinogen is a soluble protein, but when cleaved into fibrin, coagulates into an insoluble gel. The consequence of production of fibrin polymers is increased viscosity of blood or plasma and impedance of flow, which in consequence, is therefore measurable by this device.

Calcium is a required cofactor in the coagulation cascade, so blood treated with a calcium chelator, such as citrate, does not clot. The coagulation cascade can be reactivated by introducing a molar excess of calcium relative to citrate. For the herein described coagulation test, the blood sample is initially treated with citrate. Other calcium chelators, such as EDTA, produce similar effects. The initial vertical separation component of the device separates plasma from blood. (The test could also be performed using whole blood.) The separated plasma reaches the quantitative dial and migrates both directions at equal rates. One direction of the dial is treated with calcium to allow the coagulation cascade to initiate. This side of the dial can also be treated with thromboplastin or other materials that accelerate coagulation. The other side of the dial remains untreated so that migration of plasma in this direction is not retarded due to coagulation. The plasma migrating in each direction on the dial eventually meets somewhere on the opposing side of the dial. The point where the plasma meets directly indicates the capability of the blood sample to coagulate. For example, a blood sample that is completely deficient in coagulation will meet 180° from where the plasma entered the quantitative dial since blood migrating in each direction will have traveled at the same rate. With blood samples that have increasingly healthy coagulation function, the point of convergence of the plasma on the dial increasing favors the side of the dial where coagulation (and therefore retardation of plasma migration) occurs.

Deficiencies in the intrinsic, or activated partial thromboplastin time (aPTT), are tested similarly. Factors that induce the intrinsic pathway such as kaolin (insoluble silicate) or negatively-charged phospholipids can be introduced to one side of the quantitative dial along with calcium. Blood is administered and exposed to citrate as described above then plasma migrates along the dial converging elsewhere on the dial based on coagulation via the intrinsic pathway.

Uses for this device also include, but are not limited to: (1) Basic monitoring of coagulation deficiencies. (2) Monitoring of patients taking anticoagulants, for example: aPTT is monitored in patients taking heparin and PT is monitored in patients taking Warfarin. (3) Thromboplastin generation tests (TGT) to differentiate between factor VIII clotting issues in people suffering from hemophilia A and factor IX clotting issues as in hemophilia B individuals. (4) Testing of specific factors to ascertain deficiencies within coagulation pathways.

There are several possible means to use micro-sized polystyrene beads combined with immunochemistry principles to change porosity/permeability of the porous media. The change in flow rate provides an inversely proportional indication of target analyte concentration within a sample. Accumulation of beads within the void volume of a porous membrane such as lateral flow papers (Fusion 5, Whatman) or nitrocellulose membranes (Vivid) serves to attenuate flow of the applied sample by changing the effective porosity and permeability. Precise accumulation of beads can be achieved through the application of specific molecular recognition elements such as antibodies, proteins, nucleic acids and their derivatives targeting a desired analyte. Immobilization of beads at a desired segment on the membrane will cause a change in sample flow rate on a test strip designed for a specific target. The combination of reagents and materials described in this procedure provide a rapid, analyte specific, semi-quantitative test to measure solutes such as protein, nucleic acids, and metabolites from biological samples.

In one form, a sandwich immuno-assay could be used to measure C-Reactive Protein (CRP) from a sample. The sample is mixed with a known amount of beads coated with antibody to CRP (a1) and then applied to a lateral flow membrane or paper. One segment of the membrane or paper is also coated with neutravidin (or other biotin binding protein) and a second anti-CRP antibody (a2) that is conjugated to biotin. The interaction between neutravidin and the a2 antibody generates a target-specific capture segment within the test strip. Once sample is applied it will flow through the immobilized neutravidin-biotin-antibody coated segment and beads coated with the a1 anti-CRP protein will accumulate in proportion to the amount of CRP in the sample. Accumulation of beads at this region of the test strip will effectively decrease the void volume available to the sample and retard sample flow. As beads accumulate, the effective pore size and the available space for fluid flow within the test strip is reduced and the quantity of beads immobilized at this segment of the test strip is directly proportional to the amount of CRP in the sample. Other instances of this example could consist of a1 antibody coated beads and biotin conjugated a2 antibody mixed with the sample. It is also possible to have the a1 antibody coated beads and a2 biotin conjugated antibodies coated on a sample pad to a reagent pad that precedes the immobilized neutravidin segment and are taken up by the sample as it flows through the test strip. For the latter two cases just described above, a segment of the test strip is coated with neutravidin to allow capture of immune-complexes. This application would also cover beads of smaller (nano scale) and larger sizes, combinations of bead sizes, colored indicator beads, and the coupling of beads with appropriately sized flow matrices depending upon the paired separation paper used for the analysis. The use of colored indicator beads, allows their use as reporter molecules and the lack of migration or decreased migration distance of the colored indicator beads into the test strip provides a direct correspondence to the migration of liquid sample into the strip and presence of target analyte. The beads may also be non-spherical modified shapes, functionalized with different surface chemistries, or combined with other mechanisms to affect flow rate within a porous membrane. The addition of non-specific beads (beads not bound to a molecular recognition element) can be used to cause a further reduction in flow rate generated from protein or antibody coated beads specifically recognizing a target analyte and effectively amplify the signal. This method can be adapted to a competitive assay format with the inclusion of target analyte to compete with sample analyte. Here, the presence of competing target analyte will reduce the localized accumulation of target specific beads, prevent blockage of membrane pores, and result in increased sample flow rate in direct proportion to the concentration of target in the sample. Experts familiar with lateral flow and other immunological techniques with recognize that many other types of analysis can be performed with this method. The essential aspect of this assay is the specific accumulation of beads within the flow matrix resulting in a proportional decrease in flow rate due to the reduction in void volume available for sample flow.

An alternative version of this type of assay uses the agglutination of beads within a sample to prevent or decrease flow of a sample on a test strip. Using the CRP example above, a sample is mixed with a1 and a2 antibodies to CRP adhered to beads. The sample is then applied to a porous lateral flow membrane strip. If the sample contains CRP, the beads will agglutinate, plug the void volume, and create a barrier preventing or slowing entry of the sample into the membrane. In the absence of CRP, the beads remain dispersed throughout the sample and allow sample flow into the membrane. The agglutination of beads at the sample addition site effectively reduces pore size and the available space for fluid flow within the test strip. The degree of agglutination and quantity of beads accumulated at this segment of the test strip is directly proportional to the amount of CRP in the sample. Thus, the flow rate of sample and beads into the test strip is a direct indicator of CRP concentration within the sample. As above, the migration of colored indicator beads provides a direct correspondence to the migration of liquid sample into the strip and presence of target analyte. Similarly, beads may also be non-spherical modified shapes, functionalized with different surface chemistries, or combined with other mechanisms to affect flow rate within a porous membrane. The addition of non-specific beads (beads not bound to a molecular recognition element) can be used to cause a further reduction in flow rate generated from protein coated beads specifically recognizing a target analyte and effectively amplify the signal. It is also possible to have antibody coated beads on a sample or reagent pad that precedes the immobilized neutravidin segment and are taken up by the sample as it flows through the test strip. Experts familiar with lateral flow and other immunological techniques with recognize that many other types of analysis can be performed with this method. The essential aspect of this assay is the specific accumulation of beads within the flow matrix resulting in a proportional decrease in flow rate due to the reduction in void volume available for sample flow.

Several approaches can be used to accentuate bead localized membrane pore blocking and reduce sample flow in response to a target analyte. One of these is to combine the obstruction of membrane pores by bead accumulation with enzyme mediated precipitation reactions directed by bead localization. In this instance, the combination of beads coated with enzymes or antibody enzyme fusions can be used to generate localized precipitates in the presence of specific target analytes. The combination of a non-uniform localized precipitate formation and bead accumulation would very effectively generate a reduction in sample flow rate. The presence of very small precipitates would complement pore blocking by beads as localized precipitation would plug remaining gaps due to variations in membrane pore size that are left open by beads. Alternatively, the incorporation of water soluble polymers alone or in combination with beads or enzymes would also serve to reduce flow rates in proportion to the target analyte concentration. These polymers could be used as non-specific blocking reagents or be functionalized with molecular recognition elements to add specificity to bead accumulation or precipitate formation reaction. Polymers could be conjugated or fused to bead surfaces or enzymes to add shape and create a more non-uniform blocking agent to restrict flow. The added non-uniform volume of the polymers would work in the same vein as precipitation formation to plug remaining gaps not blocked by beads due to varying membrane pore size and more effectively reduce sample flow rates.

One possible embodiment of the device would comprise a strip of filter paper in which one end has been treated with flow-modifying agents and the other end is unmodified. The sample fluid would be split in half, and introduced to both ends of the strip simultaneously. If specific analyte is present, the fluid would flow more slowly from the treated end than the untreated end, and the fluid fronts would meet closer to the treated end, while if the analyte was not present, the fluid fronts would meet in the center of the strip. If the restriction of the flow was dependent on analyte concentration, then the position of the front convergence would be an indication of analyte concentration.

Another embodiment of the device would use a circular or ellipsoid strip of filter paper (the “dial”) with the sample introduced at a single position, thereby flowing in two directions around the dial, with one arm of the dial containing flow-modifying agents. The concentration of the analyte would then correlate with the position of the front convergence on the dial. Clearly, the dial could be of any shape that would allow a sample to flow in two or more directions initially and converge at the completion of the test, but rounded shapes should lead to minimal distortion of the buffer fronts.

BRIEF DESCRIPTION OF THE DRAWINGS

FIGS. 1A, 1B, 2 and 3 show plotting of exemplary data demonstrating the theoretical basis for analyzing a fluid variable by the point of convergence of two fluid fronts along a closed circuit FIG. 4 shows a top view of an exemplary embodiment of a stopped flow device.

FIG. 5 shows a top view of the stopped flow device with a top cover removed.

FIG. 6 shows a side, cross-sectional view of the stopped flow device.

FIG. 7 shows an exploded view of an exemplary set of layered components that form the stopped flow device.

FIG. 8 shows an exemplary strip medium component that enables analysis of a fluid variable in the device.

FIG. 9A shows a top view of an embodiment of the arc flow device, in which the point of convergence is measured along a curve of the closed circuit medium through which two converging fluid paths migrate.

FIG. 9B shows another embodiment of the arc flow device, in which the point of convergence is measured along a linear portion of the closed circuit medium through which two converging fluid paths migrate.

FIG. 10 shows a top view of the device depicted in 9A with a top cover removed.

FIG. 11 shows a side, cross-sectional view of the device depicted in 9A.

FIG. 12 shows an exploded view of an exemplary set of layered components that form the device depicted in 9A.

FIG. 13 shows an exemplary component (closed circuit porous medium) that enables analysis of a fluid variable by measuring a point of convergence along two separate paths, one having a modified flow rate.

FIG. 14 shows the migration of serum, impaired coagulation plasma and healthy plasma fluid fronts relative to serum, and their points of convergence along a 110 mm circular strip of porous medium.

FIG. 15 shows a graphical plot of the relative migration distances and points of convergence depicted in FIG. 14.

DETAILED DESCRIPTION

A. Definitions

Unless defined otherwise, all technical and scientific terms herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

The term “fluid” as used herein generally refers to a solution, a liquid suspension or a colloidal suspension, including a sol, although the term could also refer to any composition that is fluidizable, whether liquid, solid or gas. “Fluidizable” means a property that renders the ability to “flow,” or be “deformable,” i.e., the ability of a substance to be poured and to assume the shape of a container that it is poured into without hindrance. A “liquid suspension” is used interchangeably with “suspension” herein and refers to a system in which solid particles, often only microscopically visible such as red blood cells in blood, are dispersed throughout a less dense liquid from which they can be filtered but are not easily settled due to system viscocity or molecular interactions. A “colloidal suspension” as used herein refers to a suspension in which the solid particles are dispersed evenly throughout the liquid.

The term fluid as used herein can also refer to solutions. The term “solution” as used herein refers to a homogeneous mixture of two or more ingredients in a single phase, generally liquid but can also be a frozen liquid or gas, where the distinct ingredients only are recognizable at the molecular level. For example, the methods and devices provided herein can be used to monitor the aggregation of an analyte of interest, where the analyte is initially in solution but forms solid particles upon aggregation.

Exemplary fluids that can be used in the methods and devices provided herein include, but are not limited to, fluids such as blood, milk, water, solutions containing biological molecules such as proteins and nucleic acids, and biological fluids other than blood such as plasma, serum, urine, saliva, seminal fluid, lavages, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof. Analytes that can serve as fluid variables or flow modifiers affecting flow rate and/or migration distance of the fluid front can be particulates that are present as a suspension or colloid in the fluid; alternatively, the analytes can be dissolved in the fluid as a homogeneous solution and can modify the flow rate or migration of a fluid front upon their transformation (e.g., aggregation or complexation with a binding partner) to form particulates. The fluid sample collected can be taken from any source, as provided herein or otherwise known in the art. Fluid samples (e.g., blood) can directly be applied from a subject onto the device provided herein, or they can be collected and/or stored prior to loading onto the device.

The term "flow rate," as used herein, refers to the amount of fluid that moves through a medium in a standard amount of time (usually, minutes).

The term "fluid front" as used herein refers to the leading edge of the fluid as it migrates along the medium. It is this leading edge of the migrating fluid that is used to measure flow rate and/or migration distance, which in turn is used to analyze a fluid variable, or an assessment parameter associated with the fluid variable.

The term "fluid variable" as used herein is any component, aspect, property or characteristic of a fluid that influences, or can be made to influence, the flow of the fluid in a porous medium. Some fluid variables can affect migration of the fluid in a manner that is dependent on the amount and/or the extent to which the variable occurs in the fluid, e.g., aggregates suspended in a fluid. Examples of fluid variables include, but are not limited to, the amount or concentration of an analyte in solution in a fluid, particles (including colloidal particles) that may be mixed within or suspended in a fluid, and fluid properties such as viscosity and surface tension. For the fluid blood, exemplary variables include blood glucose concentration, hemoglobin concentration, the concentration of clotting factors such as fibrinogen, and viscosity.

The term "value" of a fluid variable, as used herein, refers to a qualitative, semi-quantitative or quantitative measure of the fluid variable. Examples of values of a variable include the measure of viscosity in centipoise and the concentration of an analyte in weight/unit volume.

As used herein, "viscosity" refers to a physical property of fluids, including liquids, which determines the internal resistance to shear forces or resistance to "flow," and is generally expressed in centipoise (cps).

The term "internal forces," as used herein, refers to forces that can affect movement of fluid in medium. Internal forces include, but are not limited to, capillary action, wicking, bulk flow and pressure differentials. Thus, internal forces are forces inherent in a system or device and are distinct from external forces, such as gravity and forces supplied by pumps, which are not generated by the materials and/or design of a medium-containing system.

The term "internal influences," as used herein, refers to influences that can affect movement of fluid in a medium that are inherent to the fluid and/or the system that includes a medium for the flow of fluid therethrough. Internal influences include, but are not limited to, paticulates in suspension in the fluid, chemical or biological reactions that impede fluid flow, interparticle and particle-medium adhesion.

The term "bulk flow," as used herein, refers to a property of the movement of fluids and components thereof in which the movement of fluids due to forces such as capillary forces entrains components of the fluid and causes them to flow.

The term "absorptive capacity," as used herein, refers to a measure of the quantity of liquid a material can hold. It is reported on either an area basis (e.g., gm of liquid per square meter of material) or a weight basis (e.g., gm of liquid per gm of material)."

The term "absorption," as used herein, refers to the process whereby atoms, molecules or ions enter or permeate a bulk phase (e.g., liquid, gas or solid) and are taken up by the volume of the phase.

The term "adsorption," as used herein, refers to the adhesion of molecules to a surface referred to as the adsorbent. A variety of forces of varying strengths can promote such adhesion, including but not limited to, van der Waals forces, electrostatic interactions and chemical bonds, e.g., ionic and covalent bonds.

The term "blood components", as used herein, refers to red blood cells, platelets, white blood cells, plasma, serum, proteins such as CRP, glucose, clotting factors and any other component that is naturally present in blood or can be obtained from blood.

The term "parameter," used interchangeably herein with "assessment parameter," refers to a property associated with a fluid variable that is analyzed by the methods and devices provided herein. The property can be used to identify and/or monitor the cause or nature of a condition, situation or problem. For example, the detection of glucose in blood as assessed by a change in its flow rate or migration distance can be used to diagnose and/or monitor diabetes. As another example, the detection of decreased flow rate of blood by the methods and devices provided herein can be correlated with clotting time, a parameter that is indicative of whether the plasma is healthy or coagulation-impaired. The term "blood parameters" as used herein refers to a property that is associated with a particulate analyte (such as red blood cells, white blood cells, clotting factors such as fibrinogen, hemoglobin or platelets) present in blood that can be used to identify and/or monitor a blood-related disease or other disease. Exemplary blood parameters include clotting time and hemoglobin concentration.

The term "hematocrit" as used herein refers to the percentage by volume of packed red blood cells after the blood has been processed, such as by centrifugation to separate the red blood cells from the plasma. The term "hematocrit", as used herein, is considered equivalent to and linearly related to "hemoglobin concentration" (3% hematocrit approximately equals 1 g/dL of hemoglobin). Therefore, all references to hematocrit within this document also refer to hemoglobin concentration and the device provided herein both hematocrit and hemoglobin conventration. Both these blood parameters can be used to identify and monitor disease conditions, such as anemia.

The terms "medium," "media," "substrate" are used interchangeably herein, and refers to any material through which movement of a fluid can occur, and measurement of a fluid front can be effected. The movement of the fluid through the medium is such that its flow rate and/or migration distance is directly dependent, or can be modified to depend, on a variable of the fluid. In particular methods and devices for separating components of a fluid mixture provided herein, the medium is a solid material. In some embodiments, the medium is porous and the flow rate of the fluid is modulated by the relative ability of one more components of the fluid to move through the pores. In other embodiments, the medium can be non-porous and channels can be etched on the non-porous medium to effect migration of the fluid. Exemplary materials for the medium include, but are not limited to, filter paper, nitrocellulose, glass fiber filters and glass. In methods provided herein wherein the fluid mixture is an aqueous fluid mixture, the medium is a hydrophilic material. "Differential migration" as defined herein refers to the different rates at which a fluid whose flow rate is modified and a fluid whose flow rate is not modified migrate in the medium.

The term "liquid component" of a fluid refers to the portion of the fluid that remains after substantially all the solid component(s) of interest, or particulate analytes, have been separated from the fluid. The term "solid component," used interchangeably with "particulates" or "particulate analyte" refers to solid particles of interest in a fluid; generally they are fluid variables that impact, or can be modified to impact, the flow rate of the fluid. In some embodiments, the solid particle of interest is an aggregate of an analyte that is originally in solution in the fluid and forms a solid particle suspended in the fluid upon aggregation. The term "solid particle" as used herein can refer to particles in the size range (average length, width or diameter) of about or at 0.001 micron (μm) to about or at 500 microns, but generally are in the range of about or at 0.5 micron to about or at 1.0, 2.0, 3.0, 4.0, 5.0, 6.0, 7.0, 8.0, 9.0, 10.0, 15.0, 20.0, 25.0, 30.0, 40.0 or 50.0 microns.

The term "agglomerates" refers to the association of one or more particles, such as particulate analytes, loosely held together by van der Waals forces or surface tension or electrostatic or combinations thereof. In some instances, associations held by electrostatic forces can be defined as "Flocculates." For the purposes herein, "agglomerates" also encompasses "Flocculates".

The term "aggregates" refers to the association of one or more particles, such as particulate analytes or analytes in solution, to form larger solid particles (or, if the analyte was originally in solution, particles). Aggregates generally are not easily broken apart, which inhibits their migration in a medium and allows the process of aggregation to be monitored.

As used herein, a "detectable label" or moiety or an imaging label or moiety refers to moieties used to image a particulate analyte of interest. Such moieties include, for example, fluorescent moieties, radionuclides, magnetically detectable isotopes or compounds, sonographic imaging agents, chromophores, latex microspheres, or quantum dots.

As used herein, a "binding partner" is a compound that specifically binds to a particular molecule or class of molecules (analyte(s) of interest). Binding partners as used herein bind to analytes and can, in some embodiments, promote or inhibit the formation of particle aggregates. Types of binding partners can include beads, proteins, nucleic acid molecules, carbohydrates, lipids, ligands, drugs, ions and any other compound that can specifically bind to a particular molecule.

As used herein, the term "proximal end" refers to the end of the device or component of the device (such as the indicator strip) that is closer to the point at which the fluid sample is loaded onto the device.

As used herein, the term "distal end" refers to the end of the device or component of the device (such as the indicator strip) that is farther from the point at which the fluid sample is loaded onto the device.

As used herein, the term "midsection" or "middle section" in general refers to the portion of the indicator strip of the device, flanked by the proximal and distal ends, on which the migration, detection, aggregation or other property of the analyte is measured.

As used herein, reference to a housing that "at least partially" covers the indicator strip or any other component of the device means that at least 10% of the device is covered.

As used herein, the term "dimensions" refers to shape, length, width and area

As used herein, the term "saturation" or "saturated" refers to a condition, point or stage where no more of the liquid or fluid can be absorbed or adsorbed by the medium through which it migrates.

The term "diffusion," as used herein, refers to movement of a fluid from an area of high concentration to an area of low concentration.

The term "adhesion" or "adhesive forces," as used herein, refers to the intermolecular attraction between unlike molecules. One example of adhesion is the intermolecular attraction between fluid molecules and the walls of a glass tube containing the fluid.

The term "capillary action" or "capillary force," as used herein, refers to the force that results from adhesive forces and surface tension acting on a fluid in a small passage or vessel, such as a tube, which serves to move a fluid through the vessel. When the adhesive force generated by intermolecular attraction between fluid molecules and the walls of a vessel in which the fluid is contained is stronger than the cohesive forces within the fluid resulting from intermolecular attraction between the fluid molecules, an upward force on the fluid at the edges of the vessel results. This force pulls the fluid at the vessel edges upward resulting in a meniscus. At the same time, surface tension generated by the enhanced cohesive forces between fluid molecules at the surface of the fluid acts to hold the surface intact resulting in the upward movement of the entire fluid surface and not only the edges of the fluid surface. This combination of forces is referred to as capillary force or action.

The term "wicking" or "wicking forces," as used herein, refers to the movement of fluid through a porous medium as a result of capillary forces occurring in the pores of the medium. Typically, a porous medium has some degree of capillarity to the extent that fluid moves through the medium due to capillary forces created by, for example, small diameter pores or the close proximity of fibers.

The term "meter" as used herein with reference to an action performed on a fluid sample, such as, for example, blood, refers to measuring a known amount of the fluid and analyzing a known amount of fluid loaded into a medium.

The term "flow-modifier" or "flow modifying agent," used interchangeably herein, refers to an agent or condition that modifies flow rate and/or migration of a fluid through a medium. Thus, for example, although a certain molecular analyte, e.g., a protein, may not directly affect fluid flow by its presence or amount in a fluid, it can be reacted with, bound to, or otherwise manipulated by another agent or condition to affect fluid flow through, for instance, blocking pores and filling void volumes of a medium or increasing the viscosity of a fluid. The nature of the fluid may be modified through changes in the viscosity, the surface tension, or through formation of gels or meshes via polymerization reactions. The effective media may be modified through changes in the porosity, pore radii or permeability. An agent or condition that is used to modify the flow of a fluid is referred to herein as a flow-modifying agent.

The term "closed circuit" as used herein refers to any medium that permits fluid to migrate along two or more convergent paths. The fluid may be applied to a single loading zone on the closed circuit medium, or it may be applied at more than one loading zone from which it converges and meets at a single point, referred to herein as the "point of convergence." Closed circuits can assume a variety of shapes, as long as they permit two or more fluid fronts to converge. Exemplary shapes include circular, elliptical, oval, oblong with two linear sides and curved ends ("race track" shape as in FIG. 9B), etc.

The term "convergent" as used herein refers to two or more fluid paths moving toward and/or meeting at a common point, referred to herein as the "point of convergence." The term "point of convergence," as used herein, refers to a point where more than one fluid front converges. The "point of convergence generally is on a closed circuit medium (with a single fluid application zone), but it can also refer to a point on a medium having one open end and one closed end, like a horseshoe (more than one fluid application zone converging at a single point).

The term "curvilinear," as used herein, refers to a fluid trajectory (path defined by the medium) that is characterized at least in part by a curved line. A curvilinear fluid trajectory follows a curved path but can also move linearly along a portion of the path.

B. Methods of Analysis of Fluid Variables

Provided herein are methods for analyzing and assessing variables of a fluid. The methods include application of a fluid to a substrate and analysis of the movement of the fluid through the substrate in order to assess a variable of the fluid based on fluid migration through the substrate. Because a variable of a fluid can influence, or can be made to influence, the flow of the fluid through a substrate, it is therefore possible to assess a fluid variable by analyzing fluid movement through a substrate. A variable of a fluid can affect, or be made to affect, migration of the fluid in a manner that is dependent on the amount and/or the extent to which a fluid variable occurs in the fluid. It is therefore possible to quantitatively assess a fluid variable by analyzing fluid movement through a substrate. Methods and devices provided herein for analyzing a variable of a fluid apply this correlation between variable presence in a fluid and fluid migration characteristics, such as migration distance and relative flow rate, to the determination of the presence and/or amount of a variable in the fluid.

In the methods and devices provided herein, analysis of fluid movement is based in the detection of cessation of fluid flow. Cessation of flow can be detected either through detection of a fluid front that has ceased to advance in a medium or through detection of the convergence of the fluid fronts of two or more paths through which a fluid flows. The point at which flow ceases defines the migration distance of the fluid which is indicative of the rate of flow of the fluid. As described herein, flow rate can be correlated to a fluid variable, such as, for example, amount or concentration of a component in a fluid. Thus, the methods and devices provided herein make possible the qualitative and/or quantitative assessment or measurement of a fluid variable through fluid front determinations.

1. Fluids and Variables Thereof

Provided herein are methods for analyzing a variable of a fluid. The methods utilize flow characteristics of a fluid as an indication of presence, absence, amount or extent of a variable of the fluid.

a. Fluids

Fluids that can be analyzed in the methods provided herein include, but are not limited to liquids, such as a pure liquid or a liquid mixture, including mixtures of two or more liquids or of one or more liquid(s) and one or more solids or gases. Pure liquids have a constant composition with fixed ratios of elements, such as, for example, water, alcohol and oil. Liquid mixtures include, for example, aqueous mixtures. Liquid-solid mixtures may contain any form of solid, including, for example particles.

b. Fluid Mixtures and Components

Fluid mixtures include solutions, suspensions, colloids, sols and heterogeneous mixtures. As described herein, one of the variables of a fluid that can be analyzed using methods and devices herein is the presence, amount or concentration of a component (also referred to as an analyte) of a fluid, e.g., a liquid, mixture. Examples of liquid mixtures that may contain an analyte to be assessed in methods provided herein include, but are not limited to, body fluids, water samples and beverages. Body fluids include native body fluids which are taken from or excreted by the body (e.g., of an animal, including mammals and, in particular, humans) and non-native liquids, in particular wash liquids, containing cells from the body, in particular from organs and body parts. Particular examples of body fluids include, but are not limited to, blood, bone marrow, cerebrospinal fluid, saliva, sweat, urine, lymph, ocular lens fluid, interstitial fluid, vaginal secretions, sputum, synovial fluid, pleural fluid, mucus, amniotic fluid, ascites, semen, feces, effusions, aspirates and wash liquids from organs (e.g., colon, lung, or bronchial lavage, bladder irrigation fluids).

c. Fluid Variables

A fluid variable can be any component, aspect, property or characteristic of a fluid that influences, or can be made to influence, the flow of the fluid in a porous medium. Some fluid variables can affect migration of the fluid in a manner that is dependent on the amount and/or the extent to which the variable occurs in the fluid. Examples of fluid variables include, but are not limited to, molecular entities that may be in solution in a fluid, particles (including colloidal particles) that may be mixed within or suspended in a fluid, and fluid properties such as viscosity, surface tension, density and adhesion forces with the medium, which is associated with contact angle.

i. Fluid Components as Fluid Variables

Fluid components include any entity or entities that forms the fluid, such as an element (e.g., mercury) or compound (e.g., water, alcohol, oil), or any entity that is mixed with the fluid. Entities that may be mixed with a fluid include any solid, liquid or gaseous components such as, for example, molecular entities and particles. A fluid component can be dissolved in the fluid (e.g., particles of a size on the molecular or ion level) or not dissolved in the fluid, such as, for example, particles suspended in a fluid. Generally, dissolved particles are of a size that is on the molecular or ion level. For example, the particles typically are less than 1 nanometer in size. Molecular entities include, but are not limited to, small molecules, such as pharmaceutical compounds (e.g., therapeutic drugs) or other drugs (e.g., theophylline, digoxin, phenyloin, thyroxins, cocaine and amphetamines), biomolecules (e.g., amino acids, fatty acids, peptides, polypeptides, oligopeptides, proteins, immunoglobulins, lipids, phospholipids, nucleotides, oligonucleotides, polynucleotides, nucleic acids, carbohydrates, oligosaccharides, polysaccharides and salts) and gases (e.g., oxygen and carbon dioxide).

Larger particles that generally may not be dissolved in the fluid are typically at least 1 nanometer in size (e.g., diameter) or larger than 1 nanometer. Such particle sizes include, for example, sizes of 2 or more nanometers, 1-5 nanometers, 1-10 nanometers, 10-20 nanometers, 1-100 nanometers, although most larger particles tend to be greater than 100 nanometers in diameter. For example, such particles may be 5-200 nanometers, 1-500 nanometers, 1-1000 nanometers, 100-500 nanometers, 500-1000 nanometers, at least 1000 nanometers, 1000 nanometers or more, or greater than 1000 nanometers, at least 1 micron, 1 micron or more, 1-5 microns, 5-8 microns, 1-10 microns, 10-50 microns, 50-100 microns, 1-100 microns, 100-150 microns in size. Thus, the particles may be such that they are not visible with an optical microscope, or visible with the aid of a microscope (e.g., microscopic), a magnifying glass or with the unaided eye.

In particular embodiments, the particle is one that is about the size of a red blood cell. For example, the particle may have a diameter in the range of 6-8 microns. Exemplary particles that can be analyzed using methods provided herein include, but are not limited to, cells (e.g., blood cells such as red blood cells (erythrocytes) and white blood cells (leukocytes, including agranulocytes such as lymphocytes and monocytes, and granulocytes, such as neutrophils, basophils, and eosinophils)), thrombocytes (platelets), synovial fluid cells and cancer cells, microorganisms, bacteria, yeast, pigments, particulates and aggregates of these and other particles.

iii. Viscosity

Viscosity is a fluid property that can be analyzed and assessed using the methods provided herein. Viscosity is a measure of the resistance to flow of a fluid due to the intermolecular forces acting in the fluid. Thus, the viscosity of a fluid directly affects the flow of a fluid. Generally, the fluidity, or ease of movement, of a fluid is inversely related to the viscosity of the fluid.

A number of factors can influence fluid viscosity. Such factors include, but are not limited to, concentration, aggregation, agglutination and polymerization of components in a fluid. Thus, fluid variables that can be analyzed using methods provided herein also include aggregation, agglutination and agglomeration of components of a fluid.

(a) Component Concentration

The amount or concentration of a component in a fluid can influence the viscosity of the fluid. In particular, there are several examples of the effect of the concentration of biological components on fluid viscosity. Living microorganisms, such as bacteria and algae, can affect viscosity of a fluid in which they occur. For example, *Chlamydomonas reinhardtii*, a type of single-celled, swimming green algae, has been reported to increase the viscosity of a fluid (see, e.g., Rafai et al. (2010) *Phys. Rev. Lett.* 104:098102) with increasing concentration of the algae cells, whereas *Bacillus subtilis*, a single-celled swimming bacterium, reportedly decreases the viscosity of a fluid (see, e.g., Sokolov and Aranson (2009) *Phys. Rev. Lett.* 103:148101). It has also been reported that the viscosity of strawberry juice increases with increasing concentration of soluble solids in the juice (see, e.g., Juszczak and Fortuna (2003) EJPAU vol. 6, no. 11; http://www.ejpau.media.pl/volume6/issue2/food/art-11.html). Additionally, several studies have reported that the viscosity of blood increases with increasing red blood cell fraction (i.e., hematocrit) in blood (see, e.g., Pries et al. (1992) *Am. J. Physiol.* 96:562 and Eckmann et al. (2000) *Anesth. Analg.* 91:539)

(b) Aggregation

Aggregation of components, such as particles, in fluids can also influence the viscosity of the fluid. For example, red blood cell aggregation in blood contributes to most of the increase in blood viscosity that occurs at low shear rates (see, e.g., Moriarty and Gibson (2005) *Curr. Opin. Cardiol.* 20:318-323). According to one proposed mechanism for red blood cell aggregation, under conditions of low shear rate (slow to stationary blood flow), the attractive Van der Waals forces between erythrocytes can lead to binding of the red blood cells. At the same time, plasma proteins can counteract the repulsive forces between the negatively charged erythrocyte cell membranes. Large plasma proteins, such as fibrinogen and low-density-lipoprotein cholesterol (LDL-C), can be absorbed onto red blood cell membranes and act as bridging molecules that facilitate aggregation of red blood cells. The bridging forces due to adsorption of these macromolecules to adjacent erythrocyte cell surfaces exceed the disaggregating forces of electrostatic repulsion, and red blood cell aggregation occurs.

(c) Agglutination

Agglutination of components, such as particles, in fluids can also influence the viscosity of the fluid. Agglutination refers to the clumping together of antigen-bearing cells, microorganisms or other particles in the presence of specific immunoglobulins or antibodies. The antibodies, which have multiple sites for binding to antigen, serve to link together the antigen-bearing particles to form an agglutinate, or clumped mass, of the particles.

An example of particle agglutination in blood is the agglutination of red blood cells of different antigenic types. Blood types arise due to the presence of different red blood cell membrane surface antigens or glycoproteins: the A antigen, B antigen and Rh antigen. Type A blood contains red blood cells carrying the A antigen and also contains anti-B antigen antibodies in the plasma. Type B blood contains red blood cells carrying the B antigen and also contains anti-A antigen antibodies in the plasma. Type AB blood contains red blood cells carrying the A and B antigens and contains no anti-A antigen antibodies or anti-B antigen antibodies in the plasma. In contrast, type O blood contains red blood cells that lack A and B antigens but contains anti-A and anti-B antigen antibodies in the plasma. Blood type also depends on whether red blood cells carry an Rh factor antigen on the cell membrane surface. If the antigen is present, the blood is referred to as positive for the Rh factor (i.e., Rh+), whereas if the antigen absent, the blood is negative for the Rh factor (i.e., Rh−). Rh negative blood can develop anti-Rh antibodies upon exposure to Rh positive red blood cells. In order for a blood transfusion to be successful, the ABO and Rh groups of the blood donor and recipient must be compatible. If they are not, the red blood cells from the donated blood will agglutinate due to the presence of recipient antibodies specific for antigens on the donated red blood cells.

(d) Polymerization

Polymer formation through the bonding of multiple monomers within a fluid can also influence fluid viscosity. For example, fibrin polymers are generated during blood clot formation through polymerization of the fibrous protein fibrin which forms a three-dimensional, cross-linked mesh around activated platelets. The clot structure of the fibrin polymer has been correlated with an increase in the viscosity of blood (see, e.g., Kaibara (1996) *Biorheology* 33:101).

iii. Surface Tension

Surface tension is another property of a fluid that can be analyzed and assessed using the methods provided herein. Surface tension provides the motive force for flow by capillary action. Surface tension is generated by the enhanced cohesive forces between fluid molecules at the surface of the fluid. This occurs because the molecules on the surface of a liquid are not surrounded by like molecules on all sides and thus they are more attracted to the adjacent like molecules at the liquid surface. These adhesive forces at the fluid front are transferred to the bulk fluid by surface tension along the fluid front interface. Changing solute concentrations lead to solute-dependent changes in surface tension. In general, surfactants (detergents) and alcohols tend to lower surface tension of aqueous solutions, while inorganic salts tend to raise surface tension, while sugars have little effect. Therefore, any reaction that results in the creation or destruction of surfactants, alcohols, or inorganic salts in the presence of an analyte can be used in this device to determine concentration.

2. Movement of Fluids through a Substrate

A fluid flows, or moves, through a substrate based on the continuous relative movement of the fluid components, e.g., particles, upon the application of a force to the fluid. The force applied to cause capillary flow is the force of adhesion between the fluid molecules and the surfaces of the medium. If the adhesion forces are greater than the internal cohesion forces between fluid molecules, the fluid molecules at the interface advance into the medium, and cohesion forces, in the form of surface tension, pulls the bulk fluid along. As the fluid, such as a liquid, flows in an overall bulk flow direction through the medium, the substance which previously occupied the medium (i.e., a gas, such as air, or possibly another fluid) is displaced. The fluid front is the boundary between the forward-most (relative to the direction of bulk flow) particles of the flowing liquid and the displaced substance. The fluid front is the point used in determining distance of migration of the fluid relative to the point at which flow was initiated. Methods and devices provided herein utilize detection of fluid front position in the analysis and assessment of fluid variables.

In general, the fluid front is not a sharply defined boundary, but rather diffuse, due to the distribution of pore sizes and shapes in the medium. However, a choice of medium can usually be made that allows a sufficiently objective visual determination of the position of the fluid front.

The flow of the fluid through the porous medium is promoted by the capillary forces which act at fluid front, and opposed by the viscous forces which act throughout the fluid column in the medium. Since the geometry of the fluid front is largely constant, while the size of the fluid column increases with time, the viscous forces become larger compared with the capillary forces (and the mass of the fluid being acted on by the forces increases), and the flow rate decreases with time.

The size of the pores also affects flow rate. The capillary forces are inversely proportional to the pore radius, while the viscous forces are inversely proportional to the radius squared. The net result is that the velocity of the fluid in capillary flow for a single channel is proportional to the pore radius. However, because in general, porous media have a distribution of pore radii, and these pores are interconnected in complex ways, it is not a simple matter to predict capillary flow characteristics for a porous medium.

a. Substrates

A substrate, also referred to as a medium, is any material on which or through which movement of a fluid, such as a liquid, can occur. In particular methods and devices provided herein, the substrate is one on which, or through which, fluid movement can occur via capillary action (i.e., capillarity). The movement of the fluid on or in or through the substrate is such that the distance of migration of the fluid will be affected by changes in one or more variables of the fluid. In methods and devices provided herein for analyzing a fluid variable, a substrate is a solid material. In particular methods and devices provided herein, a substrate is a porous medium. The medium may be made up of a material that is consistent in all aspects throughout the medium (i.e., a single material) or may vary in certain aspects at particular areas of the medium as can be achieved by using two or more different materials in fluid communication with each other or by modifying a single material at certain positions in the medium. In methods provided herein wherein the fluid is an aqueous fluid mixture, the medium is a hydrophilic material. Substrates for use in the methods and devices provided herein include surfaces modified by embossment or photolithography. Other suitable substrates can include fiber bundles or small surface channels.

For example, the medium can be, or contain, a natural and/or synthetic material containing spaces or holes of uniform or varied sizes. The spaces can form nets or can form pores, or passages, through which some components, e.g., liquids, molecules, ions, may readily move (i.e., the medium is readily permeable to the components) but through which movement of other components is retarded or impeded due, for example, to the size and/or shape of the component. Although these other components may move through the spaces of the medium, the movement will be at a slower rate. Thus, the medium is less permeable to such components. Some components may be of a size and/or shape such that they are trapped in or at the entrance to the spaces and, thus, will be excluded from movement in the medium. In this case, the medium is referred to as being impermeable to that component. Other moving components may pass completely through and exit the medium; however, such movement might be at a modified rate due to blockage of pores in the medium by the entrapped or slower moving components. Because the rate of rate of movement, or flow, through the medium of a fluid component(s) for which the medium is most permeable can be affected by the movement of a component(s) for which the medium is less permeable, the migration distance of the fluid front will vary depending on the behavior of the movement of the component(s) of the fluid. Media in which movement of certain components of a fluid may impeded based on component size are referred to as size exclusion media. Such media can also serve to effectively separate components of fluids.

Other media for use in the methods and devices provided herein can be, or contain, natural and/or synthetic materials having properties that provide for varying degrees of interactions with different components of a fluid mixture. Such media, can differentially affect movement of components in a fluid mixture based on the differential affinities of the different components of the fluid. For example, some components of a fluid mixture (e.g., liquids, molecules and ions) may have few interactions with the medium or may not interact with the medium at all. Such components are said to have little to no affinity for the medium and will move readily through the medium. Other components of the fluid mixture may interact with or weakly bind to the medium to a limited extent (i.e., with low affinity). These components will be loosely and reversibly retained in the medium and will thus move more slowly through the medium. Still other components of the fluid mixture may interact strongly (i.e., with high affinity) and/or irreversibly with the medium and will move short distances in the medium or not move in the medium at all. The interaction of a component of a fluid mixture with a medium may be specific for that component, such as between an antibody and antigen or a ligand and receptor, or may be non-specific. Media in which movement of certain components of a fluid may retarded based on differential interaction or binding of the components to the medium are referred to as adsorption-based media. Such media can serve to effectively separate components of fluids.

Different porous media may have pores of different sizes. The pore size of a porous medium to be used in the methods and devices provided herein is selected based on several factors, including: (1) the size of any component(s) of the fluid that is to be separated from other components of the fluid mixture, (2) the sizes of the other components in the fluid, (3) the extent to which it is desired to have a particular component move or travel in the medium, (4) the distance to which it is desired to have the fluid front travel in the medium and (5) the velocity at which is desired that the fluid should travel due to capillary action. For example, if it is desired that a particular component move far enough in the medium to be resolved from the other components but not as far in the medium as the other components, and the particular component is a large solid or passive particle (e.g., latex microbead or aggregate of microbeads), a suitable pore size for the medium would be one that is about the size of, or slightly larger than the size of, the particular component, but significantly larger than other smaller components of the fluid mixture. On the other hand, if the particular component is a large deformable, or otherwise active particle (e.g., a blood cell or other such cell that actively moves through small spaces) a suitable pore size for the medium would be one that is about the size of or slightly smaller than the size of the particular component, but significantly larger than other smaller components of the fluid mixture. Such a medium would permit movement of the particular component in the medium so that it could be detected, if desired, but would separate the component from other components by retarding the movement of the component relative to the movement of the other components. Thus, when it is desired to separate a particular component from the fluid mixture, the pore size of the medium will be defined by the ability of the medium to inhibit migration of that component relative to the other components in the fluid, including the fluid itself. A suitable pore size for a separation medium for use in the methods and devices provided herein can be determined empirically by those of skill in this art based on the teachings of desired outcomes and particular relevant factors as provided herein.

As described above, the pore size also has an effect on fluid velocity, thereby affecting how long it takes a test based on these devices to run. In general, a medium with larger pores will run faster than a medium with smaller pores. By causing the reduction of pore size in a medium, for instance by capturing particles on the walls of the pores, or by causing the sedimentation of precipitates in the pores, the velocity through this medium may be decreased, leading to a decrease in the distance traveled by the fluid in a certain amount of time. The ability to affect the distance traveled by the fluid front by changing the effective pore size is crucial for the operation of the devices described herein.

A medium having a relatively small pore size may be placed in serial contact with a medium with relatively larger pores. When the fluid front passes from the larger-pore medium to the smaller-pore medium, the increased capillary forces found in the smaller-pore medium, combined with the smaller viscous forces from the fluid in the larger-pore medium will cause an increase in the velocity of the fluid.

In particular methods and devices provided herein, the medium is any material that has a pore size capable of separating blood cells from plasma. Although red blood cells have an average diameter of 7-8 $\mu$m, they can deform such that the diameter is decreased. Thus, for example, suitable pore sizes of the medium for particular embodiments provided herein can be 1-8 $\mu$m in diameter, 1-5 $\mu$m in diameter or, in particular embodiments, 2-3 $\mu$m in diameter. The porous medium could also be any material made of packed beads or packed or woven fibers such that the effective pore size is suitable for separating blood cells from plasma.

In other embodiments of the methods and devices provided herein, the medium is any material in which the pores are of a size that they can be increasingly occluded with increasing amounts of a precipitate formed upon reaction of hydrogen peroxide, peroxidase and 3,3'-diaminobenzidine (DAB) or upon reaction of alkaline phosphatase with the substrate pair BCIP/NBT causing hydrolysis of BCIP (5-bromo-4-chloro-3-indolyl phosphate) and reduction of NBT (p-nitroblue tetrazolium chloride)

In a further embodiment of the methods and devices provided herein, the medium is any material in which the pores are of a size that they can be increasingly occluded with increasing amounts of a biotin-avidin (or other binding partner, e.g., neutravidin) complex mixed with latex beads.

In a particular embodiment of the methods and devices provided herein, the flow path for fluid analysis is made up of three separate media in fluid communication in series. The three media are, in order extending from the proximal end to the distal end of the path, as follows: a borosilicate glass fiber with polyvinyl alcohol (PVA) binding (8975; Ahlstrom, Helsinki, Finland), blocked polyester-backed nitrocellulose (Vivid 170; Pall Corporation, Port Washington, N.Y.), and a PVA-treated glass fiber paper that retains particles larger than 2 $\mu$m (LF1; Whatman, N.J., U.S.A.). It was determined that this combination of materials serves to exaggerate the effect of pore clogging. The initial borosilicate glass fiber material is designed to transition the flow of particles from the vertical conduit to the Vivid 170 nitrocellulose so that the beads properly enter the nitrocellulose material and therefore are capable of clogging up the pores in the nitrocellulose, as desired for flow modification. The nitrocellulose has very small pore sizes allowing small clumped beads and LPA-biotin aggregates to collect and impede flow; thus, this is where the effective clump of beads and LPA-biotin would remain and impart its effect on flow rate. The LF1 glass fiber paper displaces a larger fluid volume and has weaker capillary forces than the nitrocellulose. Therefore, effects in the nitrocellulose will lead to a dramatic change in flow within the distally located LF1 glass fiber paper.

i. Materials

Examples of materials that may be used as media for fluid flow in the methods and devices provided herein include, but are not limited to natural, synthetic, or naturally-occurring materials that are synthetically modified, such as polysaccharides (e.g., cellulose materials such as paper and cellulose derivatives such as cellulose acetate and nitrocellulose and coated cellulose); polyether sulfone; polyethylene; nylon; polyvinylidene fluoride (PVDF); polyester; polypropylene; silica; inorganic materials such as deactivated alumina; diatomaceous earth; $MgSO_4$; or other inorganic finely divided material uniformly dispersed in a porous polymeric matrix with polymers such as vinyl chloride, vinyl chloride-propylene copolymer and vinyl chloride-vinyl acetate copolymer; cloth, both naturally occurring (e.g., cotton) and synthetic (e.g., nylon or rayon); porous gels such as silica gel, agarose, dextran, and gelatin; polymeric films such as polyacrylamide; glass fibers; synthetic fibers; composites of glass and synthetic fibers; woven or non-woven glass fiber papers (coated or uncoated), plastic fibers and blends of any of these materials.

Media used in particular embodiments of the methods and devices provided herein are woven or non-woven glass fiber papers, coated cellulose, plastic fiber materials or blends of these materials. In other embodiments provided herein, the medium material contains long bundles of fibers or beads of any material that is inert to blood cells, does not induce severe cell lysis and creates a spacing within the range of 1-8 μm. Beads are preferably held in place or adhered together.

ii. Paths for Fluid Flow

One or more media may be used in the methods and devices provided herein. For example, one medium or two, three or four media can be used. In particular embodiments, two media or more than two media or four media are employed. A medium may be positioned such that bulk fluid flow through it is substantially normal (i.e., vertical or perpendicular) to the plane of the medium (often referred to as transverse flow) or substantially parallel (i.e., horizontal or lateral) to the plane of the medium. If two or more media are used, the media can be placed vertically, horizontally, or a combination of vertical and lateral placement can be employed. In a particular embodiment of the methods and devices provided herein, one medium is positioned laterally with respect to the bulk flow of fluid. In another embodiment of the methods and devices provided herein, two media, e.g., porous media, are employed: (1) a first medium is placed so that bulk fluid flow through it is vertical with respect to the plane of the medium, and (2) a second medium following, and in fluid communication with, the first medium wherein bulk fluid flow through the second medium is lateral with respect to the plane of the medium. In a further particular embodiment of the methods and devices provided herein, four media are employed: a first medium is placed so that bulk fluid flow through it is vertical with respect to the plane of the medium, and three additional media are positioned in series in fluid communication following the first medium, wherein bulk fluid flow through the second, third and fourth media is substantially lateral with respect to the plane of the media. Two or more media in fluid communication and placed in series can thus be positioned in any manner relative to each other as long as there is continuity of the fluid flow from medium to medium in the series. Fluid communication in a series of media can be accomplished in a number of ways. For example, two media in direct fluid communication with each other can be positioned such that they overlap; that is, a portion of a surface of one medium is layered over a portion of a surface of another medium. Two media can also be positioned adjacent to each other with no overlaying of surfaces. In general, however, media in fluid communication in series are positioned to maximize fluid transfer between the media and minimize disruption of flow of the fluid at the point of connection or contact of the media in order to maintain smooth and continuous fluid flow. Typically, this is achieved through overlap of media, that is, by contacting some portion of the broadest surface of one medium with the broadest surface of the other medium. The extent of overlap of media surfaces varies depending on the type of fluid flow in each medium. In general, the extent of overlap is such that efficiency and rate of fluid transfer between the media is maximized in order to maintain constant forward-moving bulk flow of the fluid. If media are placed in series for lateral fluid flow through connecting media, the extent of surface overlap necessary for efficient operation is determined empirically and is minimized. If media are placed in series for vertical flow through connecting media, the extent of overlap of media surfaces is maximized. If media are placed in series such that bulk fluid flow is vertical through one medium and lateral in the other, the extent of overlap is maximized by placing the entire surface of the vertical flow medium in contact with the lateral flow medium.

Typically, a fine separation and high resolution of a component of interest for use in detecting and/or quantifying the component in a fluid is conducted in a lateral flow format. Accordingly, the optional use of a vertically placed medium in the methods and devices provided herein is generally in addition to a horizontally placed medium and for the purpose of providing an initial gross separation of a component of interest from other components in the fluid mixture and/or staggering the presentation of the components of the fluid mixture to the lateral flow medium, and/or for providing a controlled introduction of the fluid mixture to the lateral flow medium.

A number of formats for fluid paths formed by the media are suitable for use in the methods and devices provided herein. In general, for the purpose of moving fluid from a first point to a second point, the shape of a fluid path is designed to promote forward-moving, efficient, smooth bulk flow of a fluid with minimal distortion of the fluid front. Typically, this is most readily accomplished using a straight, linear path that has a starting point and end point without curves, bends or turns. This applies to such a fluid path whether or not the path converges with one or more other fluid paths into a single path continuing path or into a common end point. In some embodiments of the devices and methods provided herein, the fluid path formed by the medium or media for each type of flow (i.e., vertical or horizontal) in the device is a linear path. These devices are designed for detection of cessation of fluid flow either through detection of a fluid front that has ceased to advance in a medium or through detection of a point of convergence in the medium when separate aliquots of sample fluid are applied to opposite ends of a linear fluid path. In other embodiments of the devices and methods provided herein, the fluid path formed by the medium or media is a circuit or closed path that is curvilinear. A curvilinear path may include linear segments but is not linear, and has no abrupt changes in direction (i.e. corners). Abrupt changes in direction would not destroy the functionality of the device, but would reduce the utility by distorting the shape of the fluid front, thereby introducing uncertainty into the position of the point of convergence. Examples of curvilinear shapes include, but are not limited to, ellipses, including circles, ovals and racetracks. Thus, curvilinear paths include elliptical, circular, and oval- and racetrack-shaped paths that have open-space interiors, as would a ring or doughnut. Curvilinear paths are closed circuits that have definite, and generally narrow, widths with clear side boundaries on both sides of the path in order to confine bulk flow in a forward-moving direction. Thus, curvilinear paths are rings, i.e., both sides of the path are distinctly identifiable, meeting or merging only at a single point; accordingly, a curvilinear path encircles an unbroken open space.

b. Forces Effecting Movement of Fluids in Porous Media

Movement of fluid through a medium is either pressure driven, or effected by the application of an external field, which could be gravitational (pressure head due to height differentials or centrifugation), electrical (electro-osmotic flow), or even magnetic (requiring either a fluid which is ferro-magnetic itself or which contains ferro-magnetic particles). Capillary forces, also known as wicking forces, can be analyzed as being the result of the pressure differential created by the curvature of the fluid/air interface (meniscus), but it is not necessary to view capillarity from this perspective in order to analyze the flow which arises from it. All devices described herein effect fluid movement through capillary forces, although gravitational forces may add to or diminish these forces if the fluid path does not lie completely in the horizontal plane.

The design of a medium, and the system of which it is a part, can also affect movement of a fluid. For example, a section of a medium exhibiting low capillary forces could be placed in series in fluid communication with a section of a medium having higher capillary forces. When the fluid front moves from the former to the latter medium, the increased capillary forces would increase the velocity of fluid migration, which would have an effect on variables of the fluid such as, for example, separation of fluid components. In another example, the medium can be compressed in order to minimize variability in the thickness of the medium thereby controlling the volumetric uptake of fluid. Changing the shape of the medium along the flow path may also affect flow rate, although these effects are not fully understood. For instance, decreasing the width of the medium (tapering) along the flow path increases flow rate, while increasing the width slows flow rate.

In alternative methods, forces external to the materials and design of the fluid analysis system are involved in effecting movement of a fluid within the medium or media. These ancillary motive forces include, but are not limited to, pumps, gravity and pressure, and external electrical or magnetic fields. Movement of fluid in a medium can involve internal forces and/or influences, external forces and/or influences or a combination of internal and external forces and/or influences.

c. Cessation of the Flow of Fluids in Porous Media

After application of a fluid sample to a porous medium for analysis of the fluid flow therein, by either direct application to the medium or indirect application at a site that is in fluid communication with the flow-analysis medium, the fluid is permitted to move through the medium due to the motive forces and/or influences acting on the fluid until flow ceases. Flow may cease for a number of reasons. For example, flow may cease because the amount of fluid applied to the medium is less than the total capacity of the medium for the fluid. In this case, flow ceases because bulk flow of the liquid due to capillary forces at the leading edge of the fluid cause the formation of a trailing edge of liquid as liquid is pulled through the medium. Capillary forces at this trailing edge oppose the capillary forces at the leading edge. Fluid movement may occur at each fluid edge due to diffusion, but no bulk flow occurs. Absent application of an external force, e.g., a pump, to the medium, the flow of fluid ceases.

Alternatively, fluid flow in an analysis medium may cease because the amount of fluid applied to the medium exceeds the total capacity of the medium for fluid. In this case, flow ceases because the medium is saturated with fluid, i.e., there is no space remaining in the medium for additional fluid. Absent some type of system for removing liquid from the saturated medium, the flow ceases and no further migration of the fluid and its components occurs in the medium.

The methods and devices provided herein for analysis and assessment of fluid variables are designed for detection of cessation of fluid flow either through detection of a fluid front that has ceased to advance in a medium or through detection of the convergence of the fluid fronts of two or more paths through which a fluid flows. The point at which flow ceases defines the migration distance of the fluid which is indicative of the rate of flow of the fluid and, in turn, of the presence, absence, amount or extent of a fluid variable that affects, or can be made to affect, fluid flow.

3. Effects of Fluid Variables on Fluid Migration

Methods and devices provided herein for analyzing and assessing a fluid variable are based on a correlation between fluid migration characteristics and the presence and/or amount or extent of a fluid variable in a fluid. This correlation arises from the ability of a fluid variable to influence fluid flow, such as by affecting migration distance or flow rate, in a medium. A fluid variable may directly and/or indirectly affect fluid migration. A fluid variable that directly affects fluid migration in a porous medium is one that in and of itself influences fluid flow. Examples of such variables include, but are not limited to, certain particles and molecules and fluid properties. For example, a particle may directly affect fluid flow in a porous medium due to its size. Large particles, such as cells and microorganisms, can effectively block pores in media thereby blocking and attenuating fluid flow. Precipitates of certain molecules in a fluid can also serve to directly block pores of a medium and thereby reduce fluid flow. Fluid viscosity can have a significant direct effect on fluid flow due to the increased resistance of flow as the viscosity of a fluid increases. For example, aggregation of red blood cells can directly increase the viscosity of blood thereby slowing blood flow.

A fluid variable that indirectly affects fluid migration is one that may not alone have a significant effect on fluid flow but that can be made or manipulated to influence flow based on its presence and/or concentration in the fluid. Thus, for example, although a certain molecular analyte, e.g., a protein, may not directly affect fluid flow by its presence or amount in a fluid, it can be reacted with, bound to, or otherwise manipulated by another agent or condition to affect fluid flow through, for instance, blocking pores and filling void volumes of a medium or increasing the viscosity of a fluid. Thus, fluid flow may be modified by modifying the fluid or the effective medium (i.e., the combination of the original media and any molecules or particles immobilized to the original medium). The nature of the fluid may be modified through changes in the viscosity, the surface tension, or through formation of gels or meshes via polymerization reactions. The effective media may be modified through changes in the porosity, pore radii or permeability. An agent or condition that is used to modify the flow of a fluid is referred to herein as a flow-modifying agent.

a. Modification of a Medium

There are numerous ways in which the medium through which a fluid migrates can be modified such that flow of the fluid is affected.

i. Blockage of Pores in a Porous Medium (a) Formation of Precipitates

Formation of precipitates in a fluid can effectively block pores in a porous medium and decrease the porosity or permeability of the medium. One example of a flow-modifying agent that could be used for this purpose is a set of enzymes and substrates that in the presence of a particular fluid variable or analyte form a precipitate that blocks the pores and thus blocks flow.

For example, localized formation of a precipitate can be caused by antibody binding in a localized area of a medium that a liquid sample can migrate through. In an embodiment of the methods provided herein intended to measure the concentration of an analyte, such as a protein (e.g., C-Reactive Protein (CRP)) in a sample, two antibodies designated a1 and a2 that can bind to an analyte molecule or molecular complex can be employed. Antibody a1 can be associated either covalently or non-covalently with an enzyme such as horseradish peroxidase. The second antibody a2 can be unmodified or modified with a molecule such as biotin. In this embodiment, a sample suspected of containing analyte can be mixed with antibody a1, glucose and a precipitating substrate such as 3,3'-Diaminobenzidine (DAB). A region of the medium will have antibody a2 and glucose oxidase bound either specifically or non-specifically to a region distal to the point of sample application. The sample will then migrate through the prepared medium such as a nitrocellulose or nylon membrane, analyte-bound antibody a1 will be retained by binding to antibody a2 causing an increase in the localized concentration of glucose oxidase in a dose-responsive manner. Medium-bound glucose oxidase will react with glucose added to the sample producing hydrogen peroxide. In turn, the hydrogen peroxide will react with the peroxidase-labeled antibody a1 and DAB forming an insoluble precipitate that will affect the flow rate of the liquid fraction of the sample in a dose-responsive manner. This change in flow rate can be measured to determine the concentration of analyte, e.g., CRP, in the sample. Above a certain threshold concentration of analyte, this precipitate could lead to a complete blocking of fluid flow in the medium.

It is noted that unbound antibody a1 will also cause the formation of precipitate; however, due to the transient nature of this antibody presence, the quantity and rate of formation will simply contribute to a reasonable constant rate of precipitate formation that will be reasonably consistent from sample to sample. Those skilled in the art will recognize that many different targets can be measured using this approach, the major requirements being that antibody binding cause the formation of a precipitate that can affect flow rate of the liquid fraction of a sample in a manner proportional to the amount of antibody binding, or that can block the flow of the liquid fraction of a sample.

In addition, those skilled in the art will recognize that this system can be used in a competitive binding fashion where the presence of analyte in the sample will compete with added target analyte to cause a decrease in binding to a localized area of the medium causing a decrease in the localized formation of a precipitate to form thus increasing the flow rate of the liquid portion of the sample in a manner inversely proportional to concentration of target in a sample.

Furthermore, those skilled in the art will recognize that antibody a2 may be biotinylated or labeled with some other specific capture label and a specific capture moiety such as a biotin-binding protein, e.g., avidin, neutraavidin or streptavidin, bound to the medium enabling both antibodies (a1, a2) to be added to the sample and the entire complex captured, but only antibody a2 captured in a dose-responsive manner. Those skilled in the art will recognize that there are many ways to capture antibodies that include but are not limited to His tag, species specific anti-antibodies, Protein A and Protein G in addition to many others. Other potential substrate systems include but are not limited to combining alkaline phosphatase with the commonly known substrate pair BCIP/NBT.

(b) Microbeads

Accumulation of microbeads or microspheres in the pores of a porous medium can also lead to blockage of the pores. For example, latex micro-spheres suspended in the sample fluid and having diameters significantly smaller than the pore size of the porous media, can, through commonly used immunochemistry methods, be made to congregate in certain zones of a porous medium as the sample fluid flows through these zones, thereby restricting or blocking flow. Accumulation of beads within the void volume of a porous membrane such as lateral flow papers (Fusion 5, Whatman) or nitrocellulose membranes (Vivid) serves to attenuate flow of the applied sample by changing the effective porosity and permeability, potentially to the point where flow is stopped. Precise accumulation of beads can be achieved through the application of specific molecular recognition elements such as antibodies, proteins, nucleic acids and their derivatives targeting a desired analyte. Immobilization of beads at a desired segment on the medium may lead to complete cessation of capillary flow in a medium designed for a specific target, if the target concentration is high enough. The combination of reagents and materials described in this procedure provide a rapid, analyte-specific, semi-quantitative test to measure solutes such as protein, nucleic acids, and metabolites from biological samples.

ii. Alteration of Pore Size in a Porous Medium (a) Formation of Precipitates

Formation of precipitates in a fluid can also serve to reduce pore size without completely blocking a pore. For example, the use of precipitation to change flow rate can be demonstrated by an assay to measure glucose in a sample material. In this immediate embodiment, enzymes glucose oxidase and horseradish peroxidase can be bound to a region of a medium. The sample can be mixed in a known ratio with a substrate such as 3,3'-Diaminobenzidine (DAB) and the sample applied to the medium. As the sample migrates toward and through the region with the immobilized enzymes, the glucose contained within the sample will react with the glucose oxidase producing hydrogen peroxide and d-Gluconic Acid. In turn, the hydrogen peroxide and the DAB will react with the horseradish peroxidase to produce an insoluble brown-black precipitate that will serve to locally decrease the pore size of the medium thus decreasing the local flow rate. This change in flow rate can then be measured and related directly to the quantity of glucose present in the sample. The quantity of the precipitating material is proportional to the quantity of the glucose present in the sample, thus more glucose present would result in more precipitate forming thus slowing the flow of the liquid fraction of the sample more.

It is also possible to have only one of the enzymes immobilized and have the other mixed with the sample traveling through the medium, the goal being for a precipitate to form in a localized region of the medium thus affecting the flow rate. In addition, the process could be performed simply by mixing the substrate and the sample directly with the enzymes so that precipitate will form in a non-localized fashion but still serve to decrease the pore size of the membrane and affect flow rates. Persons skilled in the art will recognize that many other types of analysis could be performed using this process, the requirements being that a precipitate can be caused to form, the quantity of this precipitate being proportional to the quantity of the analyte to be measured and that this precipitate can affect the flow rate of the liquid portion of the sample through the medium. Other potential substrate systems include but are not limited to combining alkaline phosphatase with the commonly known substrate pair BCIP/NBT.

(b) Microbeads

There are several possible ways to use micro-sized polystyrene beads combined with immunochemistry principles to change porosity/permeability of the porous media. The change in flow rate provides an inversely proportional indication of target analyte concentration within a sample. Accumulation of beads within the void volume of a porous membrane such as lateral flow papers (Fusion 5, Whatman) or nitrocellulose membranes (Vivid) serves to attenuate flow of the applied sample by changing the effective porosity and permeability. Precise accumulation of beads can be achieved through the application of specific molecular recognition elements such as antibodies, proteins, nucleic acids and their derivatives targeting a desired analyte. Immobilization of beads at a desired segment on the medium will cause a change in sample flow rate on a test strip designed for a specific target. The combination of reagents and materials described in this procedure provide a rapid, analyte-specific, quantitative test to measure solutes such as protein, nucleic acids, and metabolites from biological samples.

In one embodiment, a sandwich immunoassay can be used to measure an analyte, e.g., C-Reactive Protein (CRP), in a sample. The sample is mixed with a known amount of beads coated with antibody to analyte (a1) and then applied to a lateral flow medium or paper. One segment of the medium or paper is also coated with neutravidin (or other biotin-binding protein) and a second anti-analyte antibody (a2) that is conjugated to biotin. The interaction between neutravidin and the a2 antibody generates a target-specific capture segment within the medium. Once sample is applied to the medium, it will flow through the immobilized neutravidin-biotin-antibody coated segment and beads coated with the a1 anti-analyte protein will accumulate in proportion to the amount of analyte in the sample. Accumulation of beads at this region of the medium will effectively decrease the void volume available to the sample and retard sample flow. As beads accumulate, the effective pore size and the available space for fluid flow within the medium is reduced, and the quantity of beads immobilized at this segment of the medium is directly proportional to the amount of analyte in the sample. Other instances of this example include a1 antibody-coated beads and biotin conjugated a2 antibody mixed with the sample. It is also possible to have the a1 antibody-coated beads and a2 biotin-conjugated antibodies coated on a sample pad to a reagent pad that precedes the immobilized neutravidin segment and are taken up by the sample as it flows through the medium. For the latter two cases just described above, a segment of the medium is coated with neutravidin to allow capture of immune-complexes.

This application would also cover beads of smaller (nano scale) and larger sizes, combinations of bead sizes, colored indicator beads, and the coupling of beads with appropriately sized flow matrices depending upon the paired separation paper used for the analysis. The use of colored indicator beads allows their use as reporter molecules and the lack of migration or decreased migration distance of the colored indicator beads into the medium provides a direct correspondence to the migration of liquid sample into the strip and presence of target analyte. The beads may also be non-spherical modified shapes, functionalized with different surface chemistries, or combined with other mechanisms to affect flow rate within a porous membrane. The addition of non-specific beads (beads not bound to a molecular recognition element) can be used to cause a further reduction in flow rate generated from protein or antibody-coated beads specifically recognizing a target analyte and effectively amplify the signal. This method can be adapted to a competitive assay format with the inclusion of target analyte to compete with sample analyte. Here, the presence of competing target analyte will reduce the localized accumulation of target specific beads, prevent blockage of membrane pores, and result in increased sample flow rate in direct proportion to the concentration of target in the sample. Those of skill in the will recognize that many other types of analysis can be performed with this method. A significant aspect of this assay is the specific accumulation of beads within the flow matrix resulting in a proportional decrease in flow rate due to the reduction in void volume available for sample flow.

Another manner in which beads may be used to alter pore size in a medium uses the agglutination of beads within a sample to prevent or decrease flow of a sample on a medium. For example, a sample is mixed with a1 and a2 antibodies to an analyte, such as a protein (e.g., CRP) adhered to beads. The sample is then applied to a porous lateral flow medium. If the sample contains analyte, the beads will agglutinate, plug the void volume, and create a barrier preventing or slowing entry of the sample into the membrane. In the absence of analyte, the beads remain dispersed throughout the sample and allow sample flow into the membrane. The agglutination of beads at the sample addition site effectively reduces pore size and the available space for fluid flow within the medium. The degree of agglutination and quantity of beads accumulated at this segment of the medium is directly proportional to the amount of analyte in the sample. Thus, the flow rate of sample and beads into the medium is a direct indicator of analyte concentration within the sample. As above, the migration of colored indicator beads provides a direct correspondence to the migration of liquid sample into the strip and presence of target analyte. Similarly, beads may also be non-spherical modified shapes, functionalized with different surface chemistries, or combined with other mechanisms to affect flow rate within a porous membrane. The addition of non-specific beads (beads not bound to a molecular recognition element) can be used to cause a further reduction in flow rate generated from protein coated beads specifically recognizing a target analyte and effectively amplify the signal. It is also possible to have antibody coated beads on a sample or reagent pad that precedes the segment of the medium in which migration occurs and are taken up by the sample as it flows through the medium. Those of skill in the art of lateral flow and other immunological techniques will recognize that many other types of analysis can be performed with this method. A significant aspect of this assay is the specific accumulation of beads within the flow matrix resulting in a proportional decrease in flow rate due to the reduction in void volume available for sample flow.

Several approaches can be used to accentuate bead-localized membrane pore blocking and reduce sample flow in response to a target analyte. One of these is to combine the obstruction of membrane pores by bead accumulation with enzyme-mediated precipitation reactions directed by bead localization. In this instance, the combination of beads coated with enzymes or antibody enzyme fusions can be used to generate localized precipitates in the presence of specific target analytes. The combination of a non-uniform localized precipitate formation and bead accumulation can very effectively generate a reduction in sample flow rate. The presence of very small precipitates complements pore blocking by beads as localized precipitation would plug remaining gaps due to variations in membrane pore size that are left open by beads. Additionally, the incorporation of water soluble polymers alone or in combination with beads or enzymes would also serve to reduce flow rates in proportion to the target analyte concentration. These polymers could be used as non-specific blocking reagents or be functionalized with molecular recognition elements to add specificity to bead accumulation or precipitate formation reaction. Polymers could be conjugated or fused to bead surfaces or enzymes to add shape and create a more non-uniform blocking agent to restrict flow. The added non-uniform volume of the polymers would work in the same vein as precipitation formation to plug remaining gaps not blocked by beads due to varying membrane pore size and more effectively reduce sample flow rates.

b. Modification of the Nature of a Fluid

Another way to modify fluid flow is to change the nature of the fluid in the presence of a specific analyte. For example, fluid viscosity or surface tension may be altered, and polymerization reactions can be used to generate gels or meshes in the fluid thereby slowing or even stopping flow. Microparticles can be used in addition to the polymer to increase the effectiveness. The microparticles can be coated or conjugated in such a way to bind the analyte so that they actively become part of the mesh or gel, or can be uncoated or unconjugated so that they are passively caught in the mesh or gel.

There are several possible ways to use immunochemically-modified polymers (in the presence or absence of microparticles) combined with immunochemistry principles to change the flow characteristics through a porous medium. In all cases, analyte in the sample serves as a bridge either to cross-link polymer to polymer, or polymer to micro-particle. The cross-links are due to the formation of the classical sandwich complex formed in many immunoassays, in which the analyte is bound by two different antibodies which are linked to two different polymer molecules or micro-particles. As the polymers become more highly cross-linked with each other in the presence of analyte—either directly, or through microparticles as intermediaries—the viscosity of the fluid increases, slowing flow. If the extent of cross-linking is high enough, a gel will form, leading to cessation of flow.

If the two antibodies bind to different epitopes on the analyte to form a sandwich complex, then these antibodies will be different, denoted ab1 and ab2. If only polymer is used, then one scheme would be to conjugate ab1 to one preparation of polymer, and ab2 to another preparation of polymer. These two preparations of polymer could then be mixed in different ratios in order to tune the system to be responsive to different concentration ranges of analyte. In another polymer-only scheme, the antibodies ab1 and ab2 could be conjugated in different ratios to the same preparation of polymer, so that all polymer chains could potentially be conjugated with both ab1 and ab2. Any combination of the above schemes could also be used to form a gel or mesh that would stop flow.

Micro-particles coated with ab1 or ab2 or both could be added to any of the above polymer-only schemes, or appropriated preparations of antibody-coated micro-particles could replace an analogous preparation of polymer in any of the above schemes. In general, micro-particles will have different effects on flow rate than polymers. Captured or immobilized particles can affect flow rates by changing the effective porosity, pore size, and/or permeability of the porous medium. Gels or meshes which are formed by the combination of polymer and micro-particles will behave differently than gels or meshes formed by polymers alone.

In all of the above schemes, ab1 and ab2 could be monoclonal or polyclonal antibodies, antibody fragments, aptamers, or other specific binding agents. The polymer could be linear polyacrylamide, branched polyacrylamide, polyethylene glycol, dextran, or any other polymer that may be chemically modified to allow conjugation or linkage of binding agents. The micro-particles could be latex or polystyrene micro-spheres, colloids, or any spherical or irregularly-shaped particle that allows the conjugation or coating of binding agents. The binding agents could be conjugated directly to the polymers or micro-particles, or could use an intermediary linkage. For instance, both linear polyacrylamide and antibodies could be biotinylated using known chemistry. The polymer could be reacted with an excess or neutravidin to prevent intramolecular cross-linking, then the biotinylated antibody could be added to effectively conjugate it to the polymer. The addition of the antibody to the polymer could occur either before or during the assay.

Measurement of blood or plasma coagulation time is one example of using viscosity to monitor the state of a sample. Coagulation describes a complex process through which blood is clotted. Prothrombin time (PT) measures the extrinsic pathway of coagulation. Induction of this pathway requires calcium. The process can be accelerated by the introduction of thromboplastin, a saline brain extract containing tissue factor, which initiates the extrinsic pathway. This pathway proceeds through a protein cascade that eventually leads to the activation of thrombin (factor IIa), a protease that cleaves fibrinogen. Fibrinogen is a soluble protein, but when cleaved into fibrin, coagulates into an insoluble gel. The consequence of production of fibrin polymers is increased viscosity of blood or plasma and impedance of flow, and potential formation of a fibrin gel, which in consequence, is therefore measurable using the methods and devices provided herein.

4. Sample Preparation and Application to Porous Media

In carrying out the methods provided herein for analyzing and assessing fluid variables, a sample of a fluid is applied to an analysis medium. The sample may be applied directly to the medium in which fluid migration will be analyzed (i.e., analysis medium) or applied to a separate sample receiving or delivery position that is in fluid communication with the analysis medium.

The amount of sample that is applied to the medium can differ for different embodiments of the methods and devices provided herein. In some embodiments, such as those in which cessation of fluid flow is detected as a convergence of the fluid fronts in two or more paths through which a fluid flows, the amount of fluid introduced into the medium is such that it is sufficient to saturate the porous medium. Thus, the amount of sample applied to the medium is such that it is in excess of the absorptive capacity of the medium (or the combined absorptive capacities of the media if more than one medium is used) in order for the medium to become saturated with the fluid sample. The actual amount of the sample need not be known as long as the amount exceeds the capacity of the medium (or media). Minimal amounts of a fluid required to saturate a particular material can be determined based on the absorptive capacity of the material or can be determined empirically. Because an excess, rather than a specific, amount of sample is applied to a medium in these embodiments of the methods provided herein, it is not necessary to meter or measure precise volumes of sample.

In other embodiments of the methods and devices provided herein, the amount of sample applied to the medium is such that it does not exceed the absorptive capacity of the medium (or media). In these embodiments, the amount of sample applied to the medium is pre-determined and metered so that a known amount of sample that is less than the amount required to saturate the medium is introduced. For example, in one such embodiment, a known volume of sample fluid which is insufficient to saturate a medium is introduced at a single location into the medium and flows from that common site into two or more paths (also referred to as "arms") in fluid communication with the common site. Because the fluid migration distances in the two or more non-convergent paths are compared in these methods, the points at which the fluid fronts cease to advance should be located within the medium, which would not be the case if the fluid saturated the medium. Accordingly, in these methods, a known amount of sample fluid that is insufficient to saturate the medium is introduced into the medium. Such amounts of a fluid can be determined based on the absorptive capacity of the material or can be determined empirically. In particular embodiments of the methods provided herein, sample amounts applied to a medium can range from about 10 μl to about 200 μl, typically between about 25 μl to about 100 μl and in one embodiment about 75 μl.

In particular embodiments of the devices provided herein for use with the methods for analyzing and assessing fluid variables, the device includes a surface at which fluid sample can be applied to the device. The surface can be a concave depression that forms a well to receive fluid sample without loss of the sample by having it run off the device before contacting the medium. The sample receiving surface is in fluid communication with the analysis medium or media. However, such a sample delivery well does not serve to meter or measure any particular volume of sample. Thus, for embodiments of the methods provided herein in which a known amount of sample fluid is introduced into the medium, the sample is metered prior to application to the medium. For embodiments of the methods in which the amount of sample fluid introduced into the medium need only be sufficient to saturate the medium, the volume of sample applied to the medium (either directly or through fluid communication with upstream elements, such as a well), is whatever unknown amount is delivered to the device.

Depending on the fluid and/or fluid components being applied to the medium, the fluid sample may be treated prior to or during migration through the medium or media. Such treatments include, for example, buffers, preservatives, dyes or other materials that serve to label the fluid front to facilitate detection or visualization thereof in the medium, and additives that inhibit coagulation of components. In a particular embodiment of the methods provided herein for analysis of blood or serum, an anticoagulant can be added to the fluid to prevent clotting of the blood sample.

Calcium is a required cofactor in the coagulation cascade, so blood treated with a calcium chelator, such as citrate, does not clot. The coagulation cascade can be reactivated by introducing a molar excess of calcium relative to citrate. Thus, in methods and devices provided herein for assessing coagulation, a blood or plasma sample can initially be treated with citrate or another chelator. Other calcium chelators, such as EDTA, produce similar effects. The initial vertical separation component of the device separates plasma from blood. (The test could also be performed using whole blood.)

C. Methods of Detecting and/or Quantifying Variables of Fluids

Provided herein are methods for detecting and/or quantifying a fluid variable, such as, for example, a component of a fluid or characteristic or property of a fluid. Because these and other fluid variables form the basis of assessment parameters used in a number of biological, diagnostic, health care, veterinary, agricultural and commercial applications. Accordingly, also provided herein are methods for evaluating assessment parameters.

Methods provided herein for detecting and/or quantifying fluid variables include application or introduction of a fluid into a medium for convergent or non-convergent flow that is analyzed with respect to the flow or migration through one, two, at least two, two or more flow paths. In convergent flow embodiments of the methods, a fluid sample, in an amount sufficient to saturate the medium, is applied to a medium and flows through two or more, or at least two, convergent paths or arms of the medium. One, or at least one, of the paths and/or the fluid sample is modified such that the presence of the fluid variable, e.g., analyte, in the fluid affects the flow in the modified path relative to the unmodified path. The migration distances of the two or more fluid fronts are readily determined by detecting the point of convergence of the two or more fluid fronts. These distances are indicative of the rate of flow of the fluid in each path.

In particular methods provided herein, the concentration of a specific analyte in a fluid is determined or measured by detecting changes in the rate of the capillary flow of the sample fluid through porous media such as filter paper. In particular, sample fluid containing analyte flows by capillarity down two or more converging arms of a common element of porous media, in which at least one of the arms has been modified by the addition of agents which affect the flow rate in response to the concentration of the analyte. The fluid fronts will converge at a position determined by their relative flow rates, which is thus indicative of the concentration of analyte in the sample fluid. The front convergence provides a well defined endpoint for the assay, without a tightly constrained read-time window. A preferred embodiment of the device would introduce the sample fluid at a single point on a filter paper strip shaped like a circle or doughnut (the "dial"), in which one arm of the dial is treated to cause a change in flow rate in response to an analyte. Sample fluid travels around both arms of the dial by capillary action. The point around the dial at which the fluid fronts converge is an indication of analyte concentration.

Many methods and materials for modifying flow in a fluid path in any of the devices or methods described herein are provided herein, e.g., viscosity modifiers, polymerization inducers, pore size-modifiers, immunochemical-based specific modifiers including antibodies and microbeads. Based on the teachings provided herein, the skilled artisan can identify additional modifiers.

In other embodiments of the methods, the fluid path is a non-convergent linear path. This lateral flow device measures the concentration of specific analytes in a sample by detecting the cessation of the capillary flow of the sample fluid through porous media such as filter paper. In particular, an aliquot of sample fluid containing analyte flows by capillarity down at least one path through a single element of porous media, or separate elements of porous media which are in serial contact with one another. Either the sample or the media is treated so that if a threshold concentration of a specific analyte is present in the sample, capillary flow is slowed to a stop. Otherwise, flow of the sample fluid by capillary action ceases once the fluid saturates the media. Flow rates may be modified by changes in either the fluid or changes in the effective media (the combination of the original media and any molecules or particles immobilized to the original media). The nature of the fluid may be changed through changes in the viscosity, the surface tension, or through formation of gels or meshes through polymerization reactions. The effective media may be changed through changes in the porosity, pore radii, or permeability, for instance by the immobilization of microbeads on the walls of the pores in the presence of analyte. Qualitative analyses of analyte concentrations in the sample may be obtained by determining whether the buffer front has moved past a specified distance after a specified time period has elapsed. Thus, provided herein are methods and apparatus for measuring analytes in fluid samples by analyzing the rate of capillary flow through porous media. The device could be used for analyzing blood chemistry components such as proteins, nucleic acids or metabolites, monitoring for infectious diseases, or many other fluid concentration measurement uses.

In particular embodiments of the methods and devices provided herein, the cessation of fluid flow is detected by cessation, near cessation or substantial slowing of advancement of one, two or more fluid fronts in a medium or media.

Such devices described herein rely on cessation of capillary flow as an analytical tool. It is the position of the buffer front that is used as an indicator of analyte concentration rather than the accumulation of reporter molecules or particles at specific positions. Some of these devices tend to exhibit a threshold analyte concentration below which flow may be only slightly restricted, and above which flow ceases or nears cessation. They are therefore ideal for qualitative analysis of analyte concentration.

In one embodiment, a known volume of sample fluid which is insufficient to saturate a medium, is introduced at a single location into the medium and flows from that common site into two or more paths (also referred to as "arms") in fluid communication with the common site. The medium in one or more, but not all, i.e., less than all, of the fluid paths is modified such that fluid flow in the path is affected in a manner that is dependent on the presence, amount, concentration or extent of a fluid variable, or analyte, in the fluid sample. The flow of the fluid in the two or more paths proceeds until sample volume is exhausted, at which point flow ceases and the two or more separate fluid fronts cease to advance in the medium. The distance of migration of the fluid in each path is determined by measuring the distance from the point of sample introduction to each fluid front. These distances, which are indicative of the relative rates of fluid flow in the paths, are compared and correlated with amount, concentration or extent of the fluid variable or analyte in the sample. In an alternative of this embodiment, a known amount of sample fluid is introduced into each of two or more separate media that do not share a common element. One or more, but not all, of the separate paths is modified to affect fluid flow in an analyte concentration-dependent manner, and the fluid migration distances in each path or arm are measured and compared to quantitatively assess fluid variable or analyte.

In another embodiment of the methods and devices provided herein which are designed for detection of cessation of fluid flow by detection of a fluid front, the amount of fluid introduced into the medium is such that it is sufficient to saturate a porous medium if given enough time Thus, after a finite period of time during which the fluid front would continue to advance, the medium would eventually become filled with fluid and the fluid front would no longer be present. However, the medium and/or the sample fluid in these devices and methods is modified such that if a fluid variable or analyte is present in the fluid in an amount, concentration or extent that is at or greater than a threshold amount, concentration or extent, the flow of the fluid will completely or substantially cease. The cessation of fluid flow is detected in these embodiments as a complete cessation or substantial or significant slowing of advancement of a fluid front. Accordingly, using these particular methods and devices provided herein, it is possible to semi-quantitatively assess the presence of a fluid variable by the cessation or substantial slowing of fluid front advancement.

In a further embodiment of the devices and methods provided herein, the cessation of fluid flow is detected as a convergence of the fluid fronts in two or more paths through which a fluid flows. For example, in a particular embodiment, cessation of fluid flow is detected as convergence of the fluid fronts that occurs when separate aliquots of sample fluid are introduced to opposite ends of a linear medium and allowed to flow towards the other end of the medium. In another particular embodiment, cessation of fluid flow is detected as convergence of fluid fronts advancing in opposite directions Devices provided herein that are designed to detect a point of convergence of two paths flowing toward each other have several advantages over fluid flow devices and methods relying on determination of analyte position based on reporter molecule accumulation. In contrast, many embodiments of the devices provided herein yield clear, sharp and well-defined endpoints herein because the meeting, or convergence, point of the separate fluid fronts is the stopping point of the fluid flow for each fluid path.

D. Apparatus for Analysis of Variables of Fluids and for Measuring Parameters Associated with a Fluid Variable Provided herein is an "arc flow" lateral flow device that analyzes fluid variables in a sample by detecting changes in the rate of the capillary flow of the sample fluid through porous media such as filter paper. In particular, sample fluid containing flows by capillarity down two or more converging arms of a common element of porous media, in which at least one of the arms has been modified by the addition of flow-modifying agents which affect the flow rate in response to the fluid variable, such as concentration of the analyte. The fluid fronts will converge at a position determined by their relative flow rates, which is thus indicative of the concentration of analyte in the sample fluid.

Another lateral flow device, a "split flow" device provided herein analyzes fluid variables in a sample by detecting changes in the rate of the capillary flow of the sample fluid through porous media such as filter paper. In particular, sample fluid containing analyte flows by capillarity down two or more arms of a common element of porous media, in which at least one of the arms has been modified by the addition of flow-modifying agents which affect the flow rate in response to the fluid variable, such as concentration of the analyte. The relative distance at completion of the fluid fronts from the sample introduction point is determined by their relative flow rates, which is thus indicative of the concentration of analyte in the sample fluid.

Other lateral flow devices provided herein, "stopped flow" devices, qualitatively assess fluid variables in a sample by detecting changes in the rate of the capillary flow of the sample fluid through porous media such as filter paper. In particular, sample fluid flows by capillarity along a path through an element of porous media, or through multiple elements of porous media which are in serial contact with each other, in which the sample and/or the fluid path has been modified by the addition of flow-modifying agents which cause flow to stop in the presence of the specific fluid variables, such as analytes. If the properties of the fluid or the media do not change with time, then it is expected that the position of the fluid front will be directly proportional to the square root of time [Washburn], so that a sufficient quantity of sample fluid will saturate the porous media if given sufficient time. If the fluid front has not moved at least a specified distance after a specified period of time, this indicates that capillary flow has ceased, thereby indicating that a threshold concentration of analyte exists in the sample fluid.

Theory of "Split Flow"

The devices described herein rely on changes in flow rate as an analytical tool. For the analysis and design of devices based on analyzing rates of capillary flow, it is necessary to have a theory that describes such flow. We use a modified form of an equation known as the Washburn equation, which describes transient flow through a circular tube due to capillary forces. We have adapted this equation to describe such flow through a porous medium, according to modern theory of fluid transport.

For a description of transient flow through a capillary, Washburn begins with the Poiseuille equation, which describes laminar flow through a circular channel due to a pressure differential:

$$v_{ave} = \frac{\Delta P r^2}{8\mu L} \quad (1)$$

where $v_{ave}$ is the average fluid velocity (volumetric flowrate divided by cross-sectional area), r is the radius of the channel, $\mu$ is the viscosity, and L is the length of the channel. For simplicity, we present a derivation that assumes a no-slip condition at the channel wall, and assumes no pressure head at the inlet of the channel. For a channel filling by capillary action, Washburn equates the average velocity with the velocity of the fluid front, and similarly takes the length of the channel to be the position x of the fluid front. The pressure generated by surface tension is given by $(2\sigma \cos \alpha)/r$ [Batchelor, Lambert], where $\sigma$ is the surface tension of the fluid, and $\alpha$ is the contact angle between the fluid and the wall of the channel. The pressure head of the column of fluid itself is given by $g\rho x \sin \theta$, where g is the acceleration of gravity, $\rho$ is the density of the fluid, and $\theta$ is the angle of the channel from the horizontal. Combining these:

$$\frac{dx}{dt} = \frac{(2\sigma \cos \alpha / r - g\rho x \sin \theta) r^2}{8\mu x} \quad (2)$$

For a horizontal channel which is fully wettable (contact angle of zero), this equation is easily integrated to give x as a function of time:

$$x = \sqrt{\frac{\sigma r t}{2\mu}} \quad (3)$$

Though Washburn and others have applied these equations to porous media as well, modeling these materials as a collection of capillary tubes, a better approach is to start with equations specifically applicable to flow through porous media. Darcy's Law (Ingham, Nield) describes laminar flow through porous media in response to a pressure differential:

$$v_{ave} = \frac{\Delta P K}{\varphi \mu L} \quad (4)$$

where K is the permeability of the media (defined by Darcy's Law, with units of area), and $\varphi$ is the porosity (void volume, or pore volume divided by total volume). Darcy's Law is usually expressed in terms of filtration velocity (volumetric flow divided by cross-sectional area, in which case the porosity term is dropped), but for the present purposes, it is better to use the intrinsic velocity, or velocity of fluid in the pores. The presence of the porosity in the denominator seems counter-intuitive, as it implies that more porous materials will have a slower flow rate. However, the permeability is itself a function of porosity, estimated by the Carman-Kozeny relationship, derived for a packed bed of spherical particles:

$$K = \frac{r_p^2 \varphi^3}{k_{ck}(1-\varphi)^2} \quad (5)$$

where $r_p$ is the average pore (or particle) radius, and $k_{ck}$ is an empirically derived constant that varies from about 35 to 50. Though this relationship combined with the above equation leads to an intuitively satisfying drop in velocity as porosity drops, and has success with empirically fitting data, it should be regarded with caution at high porosities where it predicts lower pressure drops than found experimentally [McCabe], and has K approach infinity as the porosity approaches unity. Following Washburn, Darcy's Law is converted to a differential equation in the fluid front position:

$$\frac{dx}{dt} = \frac{K(k_s \sigma - g\rho x \sin \theta)}{\varphi \mu x} \quad (6)$$

In this case, the pressure due to capillary action is not so easily defined, as pore shape deviates significantly from circular, pore size follows a variable distribution, and for pores less than 1 micron, contact angles approaching zero are not possible as this would yield pressures drops greater than atmospheric. All of these considerations are rolled into the constant $k_s$, which will vary between zero and the surface-to-volume ratio of the medium (units of inverse length). An empirical fit for these parameters can be found by recording the position of the buffer front with time, then plotting velocity (found by central difference techniques) against the inverse of the position. If the porous medium is not horizontal, then a straight line should result, having a slope of $k_d/k_r$ (as defined below) and an intercept of $-g/k_r$ (see FIG. 5). $k_d$ and $k_r$ may be thought of as the relative driving and resistive forces respectively.

$$v = \frac{K k_s \sigma}{\varphi \mu} \frac{1}{x} - \frac{K \rho g \sin \theta}{\varphi \mu} = \frac{k_d}{k_r}\frac{1}{x} - \frac{1}{k_r} g \sin \theta \quad (7a)$$

$$k_d = \frac{k_s \sigma}{\rho}, \quad k_r = \frac{\varphi \mu}{K \rho} \quad (7b)$$

For fluid flowing by capillary action through a horizontal porous medium, the following relationship is found:

$$x = \sqrt{\frac{2 k_s \sigma K t}{\varphi \mu}} = \sqrt{2 \frac{k_d}{k_r} t} \quad (8)$$

It is clear from Equation 8 that the rate of capillary flow may be modified by changing any of the constants under the radical, including surface tension, permeability, porosity, or viscosity. In most cases, the change in the fluid front would be proportional to the square root of the change in the parameter (increasing the viscosity four-fold would lead to a doubling in the front position). The exception is porosity, which would show roughly a proportional change, as the permeability also depends on porosity.

As a simple illustration, we apply this theory to a device described in this patent, in which a known volume of sample fluid is added to the center of a linear strip, and flows by capillary action down the two arms of the strip. To make the calculations tractable, we make the large simplification of assuming that the flow rate constants (as described above) are constant (but different between the two arms) throughout the entire assay. Of course, in a real scenario, the constants $R_1$ and $R_2$ would have to be integrated over both time and media length. The governing equations are thus:

$$x_1 = \sqrt{R_1 t}, \; x_2 = \sqrt{R_2 t}, \; x_1 + x_2 = L$$

where L is the distance between the two fluid fronts, and is defined by the sample volume by volume=$\phi$ w h L, w=width of the strip, and h=thickness of the strip.

Solving for $x_1$ and $x_2$ at completion therefore yields:

$$x_1 = \frac{L}{1+\sqrt{R_2/R_1}}, \quad x_2 = \frac{L}{1+\sqrt{R_1/R_2}}$$

If $R_2$ is four times $R_1$, then the distance $x_1$ of the fluid front from the sample introduction point will be half the distance $x_2$.

Theory of "Arc Flow"

For the analysis and design of devices based on analyzing rates of capillary flow, it is necessary to have a theory that describes such flow. We use a modified form of an equation known as the Washburn equation, which describes transient flow through a circular tube due to capillary forces. We have adapted this equation to describe such flow through a porous medium, according to modern theory of fluid transport.

For a description of transient flow through a capillary, Washburn begins with the Poiseuille equation, which describes laminar flow through a circular channel due to a pressure differential:

$$v_{ave} = \frac{\Delta P r^2}{8 \mu L} \tag{1}$$

where $v_{ave}$ is the average fluid velocity (volumetric flowrate divided by cross-sectional area), r is the radius of the channel, $\mu$ is the viscosity, and L is the length of the channel. For simplicity, we present a derivation that assumes a no-slip condition at the channel wall, and assumes no pressure head at the inlet of the channel. For a channel filling by capillary action, Washburn equates the average velocity with the velocity of the fluid front, and similarly takes the length of the channel to be the position $\lambda$ of the fluid front. The pressure generated by surface tension is given by $(2\sigma \cos \alpha)/r$ [Batchelor, Lambert], where $\sigma$ is the surface tension of the fluid, and $\alpha$ is the contact angle between the fluid and the wall of the channel. The pressure head of the column of fluid itself is given by gpx sin $\theta$, where g is the acceleration of gravity, $\rho$ is the density of the fluid, and $\theta$ is the angle of the channel from the horizontal. Combining these:

$$\frac{d\lambda}{dt} = \frac{(2\sigma \cos\alpha/r - g\rho\lambda\sin\theta)r^2}{8\mu\lambda} \tag{2}$$

For a horizontal channel (sin $\theta$=0) which is fully wettable (contact angle $\alpha$ of zero), this equation is easily integrated to give the position of the fluid front $\lambda$ as a function of time:

$$\lambda = \sqrt{\frac{\sigma r t}{2\mu}} \tag{3}$$

Though Washburn and others have applied these equations to porous media as well, modeling these materials as a collection of capillary tubes, a better approach is to start with equations specifically applicable to flow through porous media. Darcy's Law [Nield] describes laminar flow through porous media in response to a pressure differential:

$$v_{ave} = \frac{\Delta P K}{\varphi \mu L} \tag{4}$$

where K is the permeability of the media (defined by Darcy's Law, with units of area), and $\phi$ is the porosity (void volume, or pore volume divided by total volume). Darcy's Law is usually expressed in terms of filtration velocity (volumetric flow divided by cross-sectional area, in which case the porosity term is dropped from Equation 4), but for the present purposes, it is better to use the intrinsic velocity, or velocity of fluid in the pores. The presence of the porosity in the denominator seems counter-intuitive, as it implies that more porous materials will have a slower flow rate. However, the permeability is itself a function of porosity, estimated by the Carman-Kozeny relationship, derived for a packed bed of spherical particles:

$$K = \frac{r_p^2 \varphi^3}{k_{ck}(1-\varphi)^2} \tag{5}$$

where $r_p$ is the average particle radius, and $k_{ck}$ is an empirically derived constant that varies from about 35 to 50. Some researchers will use pore radius for $r_p$ in the above equation, however our own theoretical derivations suggest that this is only sensible if the $(1-\phi)^2$ term is replaced with an approximation (see below). Though this relationship combined with the above equation leads to an intuitively satisfying drop in velocity as porosity drops, and has success with empirically fitting data, it should be regarded with caution at high porosities where it predicts lower pressure drops than found experimentally [McCabe], and has K approach infinity as the porosity approaches unity. In addition, microscopic pictures of the cross-section of filter papers show a wide distribution of pores, which is not accounted for in Equation 5.

Following Washburn, Darcy's Law is converted to a differential equation in the fluid front position:

$$\frac{d\lambda}{dt} = \frac{K(k_s \sigma - g\rho\lambda\sin\theta)}{\varphi\mu\lambda} \tag{6}$$

In this case, the pressure due to capillary action is not so easily defined, as pore shape deviates significantly from circular, pore size follows a variable distribution, and for pores less than 1 micron, contact angles approaching zero are not possible as this would yield pressures drops greater than atmospheric. All of these considerations are rolled into the constant $k_s$, which will vary between zero and the surface-to-volume ratio of the medium (units of inverse length).

An empirical fit for these parameters can be found by recording the position of the buffer front with time, then plotting velocity (found by central difference techniques) against the inverse of the position. If the porous medium is not horizontal, then a straight line should result, having a slope of $k_d/k_r$ (as defined below) and an intercept of $-g \sin\theta/k_r$. $k_d$ and $k_r$ may be thought of as the relative driving and resistive effects respectively.

$$v = \frac{Kk_s\sigma}{\varphi\mu}\frac{1}{\lambda} - \frac{K\rho g \sin\theta}{\varphi\mu} = \frac{k_d}{k_r}\frac{1}{\lambda} - \frac{1}{k_r}g\sin\theta \quad (7a)$$

$$k_d = \frac{k_s\sigma}{\rho}, \quad k_r = \frac{\varphi\mu}{K\rho} \quad (7b)$$

For fluid flowing by capillary action through a horizontal porous medium, the following relationship is found:

$$\lambda = \sqrt{\frac{2k_s\sigma Kt}{\varphi\mu}} = \sqrt{2\frac{k_d}{k_r}t} \quad (8)$$

It is clear from Equation 8 that the rate of capillary flow may be modified by changing any of the constants under the radical, including surface tension, permeability, porosity, or viscosity. In most cases, the change in the fluid front would be proportional to the square root of the change in the parameter (decreasing the viscosity four-fold would lead to a doubling in the front position). The exception is porosity, which would show roughly a proportional change, as the permeability also depends on porosity. Equation 8 implies that for horizontal flow with constant flow parameters, plotting the position of the fluid front against the square root of time yields a straight line.

As a simple illustration, we apply this theory to a device described in this patent, in which sample fluid flows around two arms of a circular filter (the "dial") with a circumference of L, with flow ceasing once the two fluid fronts converge. To make the calculations tractable with the theory presented thus far, we make the large simplification of assuming that the flow rate parameters (as described above) are constant (but different between the two arms) throughout the entire assay. The governing equations are thus:

$$x_1 = \sqrt{R_1 t}, x_2 = \sqrt{R_2 t}, x_1 + x_2 = L$$

Solving for $x_1$ and $x_2$ at the time of front convergence therefore yields:

$$x_1 = \frac{L}{1+\sqrt{R_2/R_1}}, \quad x_2 = \frac{L}{1+\sqrt{R_1/R_2}}$$

If $R_2$ is four times $R_1$, then the fluid fronts will converge at a point ⅔ of the way around the dial along arm 2, ⅓ around along arm 1.

The above illustration depends on the flow rate parameters being constant along each arm. In general, this is not a realistic assumption. In order to develop a theory that allows for changing parameters, we must start with more basic assumptions. We therefore present an alternative derivation of the above theory using Newton's 2nd Law as the starting point:

$$\Sigma F = m\frac{d^2\lambda}{dt^2} \quad (9)$$

or, $$F_{cap} - F_{visc} - mg\sin\theta = A_{xs}\lambda\varphi\rho\frac{d^2\lambda}{dt^2}$$

where $F_{cap}$ is the driving force due to capillarity, $F_{visc}$ is the resistive force due to fluid viscosity, $mg \sin\theta$ is the gravitational force acting on the fluid, and $A_{xs}$ is the cross-sectional area of the filter paper. To maintain internal consistency, we will use Equation 6 to find the relevant forces, rearranging it, and multiplying both sides by $A_{xs}\varphi$:

$$\frac{A_{xs}\varphi^2\mu\lambda}{K}\frac{d\lambda}{dt} = A_{xs}\varphi(k_s\sigma - g\rho\lambda\sin\theta) \quad (10)$$

The $A_{xs}\varphi$ on the right side of the equation is necessary to get the proper form for the gravitational force (in the x or $\lambda$ direction), and also converts the capillary pressure into the force applied across the pore space. Equation 10 then represents the balance of forces at constant velocity, with the left side representing the viscous resistance to flow. Clearly, the terms in Equation 10 represent the forces on the left side of Equation 9. Substituting in:

$$A_{xs}\varphi\left(k_s\sigma - \frac{\mu\varphi\lambda}{K}\frac{d\lambda}{dt} - g\rho\lambda\sin\theta\right) = A_{xs}\lambda\varphi\rho\frac{d^2\lambda}{dt^2} \quad (11a)$$

$$\frac{d^2\lambda}{dt^2} + \frac{\mu\varphi}{K\rho}\frac{d\lambda}{dt} - \frac{k_s\sigma}{\rho}\frac{1}{\lambda} + g\sin\theta = 0 \quad (11b)$$

$$\frac{d^2\lambda}{dt^2} + k_r\frac{d\lambda}{dt} - k_d\frac{1}{\lambda} + g\sin\theta = 0 \quad (11c)$$

If the acceleration is zero (or close to it) then Equation 11 is the same as Equation 7. In fact, aside from the first few hundreds of milliseconds, the numerical solution (Fourth order Runge-Kutta [Press]) for Equation 11 is identical to Equation 7 out to five significant figures. Dropping the acceleration term has the significant advantage of allowing the required time step to be increased from 10 microseconds to the order of seconds, with a corresponding increase in computation speed.

It is not clear from the above equations how to model things when the parameters change with x. In particular, if the width (or thickness or porosity) changes with x, then the velocity must as well, according to continuity:

$$\frac{d}{dx}(A_{xs}\varphi v_x) = 0 \quad (12)$$

(Equation 12 relies on the simplifying assumptions that all velocity is in the x direction, and that the density ρ is constant.) However, the above derivations have assumed that the fluid moves monolithically, with the velocity varying with time, but not in x. To allow variation in the flow parameters, the theory presented in Equation 11a may be reformulated as a work/energy equation:

$$\int_0^\lambda \Sigma F \, dx = \frac{1}{2} \oint v^2 dm = \frac{1}{2} \int_0^\lambda v^2 A_{xs} \varphi \rho dx \qquad (13)$$

Since the limits of integration in Equation 13 include a variable (λ), the integrands also exhibit equality. Removing the integrals and rearranging:

$$v^2 = \frac{2}{(A_{xs}(\lambda)\varphi(\lambda)\rho)(F_{cap} - F_{visc} - mg\sin\theta)} \qquad (14)$$

The forces on the right side of Equation 14 may be adapted (in differential form, if necessary) from Equation 11a. The capillary force only exists at the capillary front. The viscous force and the gravitational force, however, must be integrated over the length of the wetted paper:

$$v^2 = \frac{2}{A_{xs}(\lambda)\varphi(\lambda)\rho}\left(A_{xs}(\lambda)\varphi(\lambda)k_s\sigma - \int_0^\lambda \frac{A_{xs}(x)\varphi^2(x)\mu(x)}{K(x)} v_x dx - g\sin\theta \int_0^\lambda x A_{xs}(x)\varphi(x)\rho dx\right) \qquad (15)$$

If the flow is horizontal, the gravitational term is zero. Applying Equation 12 to the viscous term:

$$v^2(\lambda) = \frac{2}{A_{xs}(\lambda)\varphi(\lambda)\rho}\left(A_{xs}(\lambda)\varphi(\lambda)k_s\sigma - A_{xs}(\lambda)\varphi(\lambda)v(\lambda)\int_0^\lambda \frac{\varphi(x)\mu(x)}{K(x)} dx\right) \qquad (16a)$$

$$v^2(\lambda) = \frac{2}{\rho}\left(k_s\sigma - v(\lambda)\int_0^\lambda \frac{\varphi(x)\mu(x)}{K(x)} dx\right) \qquad (16b)$$

This is a quadratic equation in v(λ):

$$v(\lambda) = \sqrt{\beta^2 + \frac{2k_s\sigma}{\rho}} \bigg| \beta; \; \beta = \frac{1}{\rho}\int_0^\lambda \frac{\varphi(x)\mu(x)}{K(x)} dx \qquad (17)$$

Equation 17 has two advantages over previous equations. The velocity does not go to infinity as x goes to zero, and it allows all the parameters (aside from the density) to change with x. As v(λ)=dλ/dt, Equation 17 may be used in a differential equation solver, such as the fourth-order Runge-Kutta, to find λ as a function of time. The integral form for β allows the porosity, viscosity, and permeability to change with position, allowing the simulation of various techniques to change flow rates in response to analyte concentration.

In some embodiments of the device, the effective permeability of the porous medium may be modified by capturing treated microbeads within the pores in an analyte-specific manner. This would have the effect of decreasing the permeability, both by decreasing the porosity and by decreasing the pore size according to the Carman-Kozeny relationship (Equation 5). While the Carman-Kozeny relationship was developed for packed beds having relatively small porosities, filter papers generally have porosities in the range of 70%-90%. The permeability according to Equation 5 goes to infinity as the porosity approaches 1.0. It would be more sensible for the permeability to go to a value such that as the porosity approaches 1.0, Equation 4 (flow through a porous medium) approaches Equation 1 (flow through an open channel). Formally:

$$\lim_{\varphi \to 1} \frac{\Delta P K}{\varphi \mu L} = \frac{\Delta P r^2}{8\mu L} \qquad (18)$$

Using Equation 5 for the permeability K, assuming the pore radius in Equation 5 becomes the radius in Equation 1, and using the value 45 for $k_{ck}$:

$$\lim_{\varphi \to 1} \frac{\varphi^2}{45(1-\varphi)^2} = \frac{1}{8} \qquad (19a)$$

The obvious problem of the denominator going to zero when the porosity goes to unity is avoided by realizing that Equation 5 is an approximation for low porosities. The predictions of this equation can be preserved at low porosities while satisfying Equation 18 by using the Taylor Series expansion on the 1−φ term, and then truncating to the first three terms:

$$\frac{1}{1-\varphi} = 1 + \varphi + \varphi^2 + \varphi^3 \ldots \approx 1 + \varphi + a\varphi^2 \qquad (20)$$

Putting this into Equation 19:

$$\lim_{\varphi \to 1} \frac{\varphi^2(1 + \varphi + a\varphi^2)^2}{k_{ck}} = \frac{1}{8} \qquad (19b)$$

Letting φ→1 and solving for a:

$$\varphi(1 + \varphi + a\varphi^2) = 2 + a = \sqrt{\frac{k_{ck}}{8}} \qquad (19c)$$

yields a=0.37 when $k_{ck}$=45. Equation 5 therefore becomes:

$$K = \frac{r_p^2 \varphi^3(1 + \varphi + 0.37\varphi^2)^2}{45} \qquad (21)$$

If Equation 21 is used to predict the effect of the capture of microbeads in a porous medium on the permeability of that medium, there are two extreme cases of how this might occur: the beads could completely clog up some pores leaving all others unaffected, or the beads could be evenly distributed across all pores, occluding their cross-sectional area. In the first case, the porosity would be affected but not the average pore radius $r_p$, while in the second case both the porosity and the radius would be affected. Since the porosity is equal to the fraction of the cross-sectional area within the pore space, and since the number of pores would not change if all are occluded evenly, the following results:

$$\frac{r_{p1}^2}{r_{p2}^2} = \frac{\varphi_1}{\varphi_2} \tag{22}$$

Figure 1B:
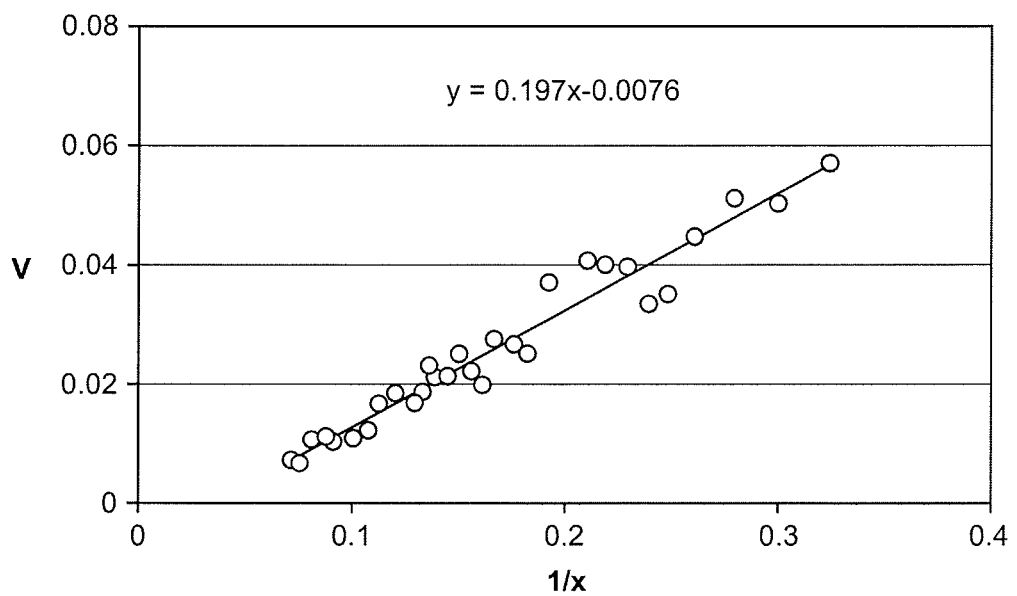

FIG. 1A shows data collected for vertical flow of water through a 0.25" wide strip of Fusion-5 separation paper (Whatman). The strip was contained in a plastic housing. At time zero, the bottom 1 mm of the strip was submerged in water containing a blue dye. At periodic intervals, the position of the liquid front was marked on the housing, and later measured with calipers. The velocity of the front (in cm/s) was determined by the central difference technique on the position data. The velocity versus 1/x was plotted in FIG. 1B. A line was fit to this data, and $k_d$ and $k_r$ (Equation 7b) were derived from the slope and the intercept. These values were then used to integrate Equation 7a, using a $4^{th}$-order Runge-Kutta method. The values from this model were then plotted in FIG. 1A as a solid line.

Figure 2:
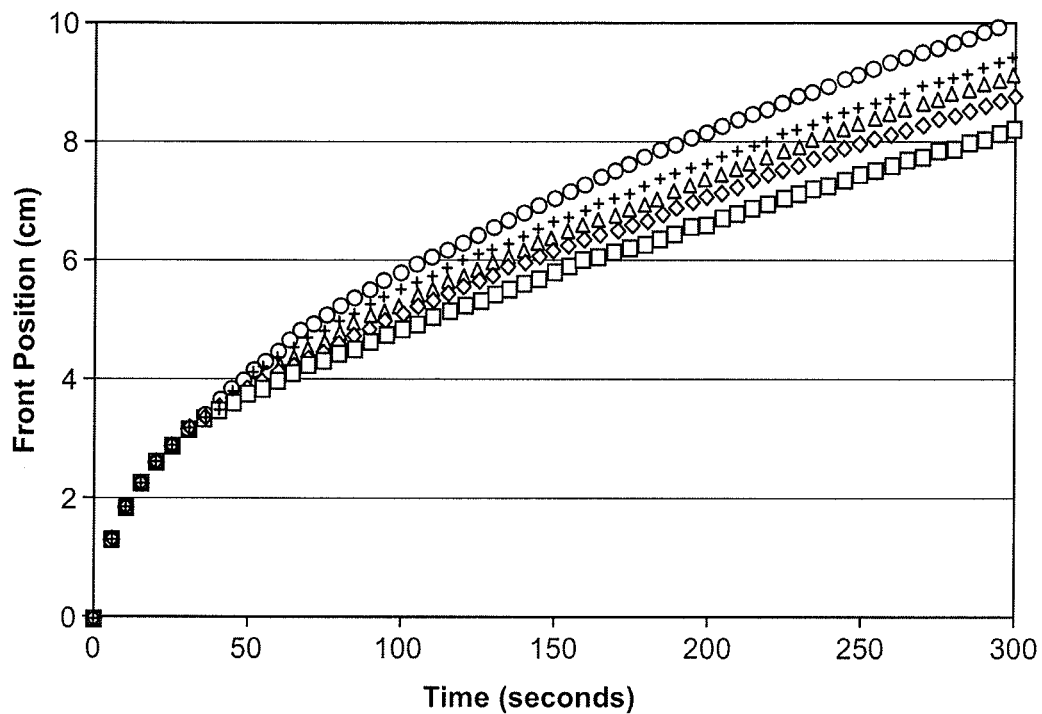

FIG. 2 the effects of changing the distribution of captured microspheres in a porous medium on flow rate. The circles show flow without any microspheres. The other plots show the results of different distributions of equal amounts of microspheres. In each case, the total volume of microspheres would be sufficient to completely fill the pore volume of a 2 mm length of the porous medium. The distribution of microspheres starts at 30 mm, and is constant until the volume of microspheres is exhausted. For the run indicated with crosses, the microspheres are distributed across a 20 mm length, so that the porosity in this section is reduced by 10%. For the run indicated with triangles, the microspheres are distributed across a 10 mm length, so that the porosity in this section is reduced by 20%. For the run indicated with squares, the microspheres are distributed across a 6.7 mm length, so that the porosity in this section is reduced by 30%. For the run indicated with squares, the microspheres are distributed across a 5 mm length, so that the porosity in this section is reduced by 40%. In each case, it is assumed that the microspheres are distributed evenly across the pores, so that the pore area of each pore is reduced proportionately to the total reduction of the porosity. In these cases, the $\beta$ term in Equation 17 is given by:

$$\beta(\lambda < x_s) = \frac{\mu \varphi_o}{\rho K_o} \lambda \tag{23a}$$

$$\beta(x_s < \lambda < x_f) = \frac{\mu}{\rho}\left(x_s \frac{\varphi_o}{K_o} + \frac{(\lambda - x_s)\varphi_t}{K_t}\right) \tag{23b}$$

$$\beta(\lambda > x_f) = \frac{\mu}{\rho}\left((x_s + \lambda - x_f)\frac{\varphi_o}{K_o} + \frac{(x_f - x_s)\varphi_t}{K_t}\right) \tag{23c}$$

where $\lambda$ is the position of the buffer front, $x_s$ is the start position of the microbead distribution (treated medium), $x_f$ is the final position of the treated medium, $\phi_o$ and $K_o$ is the porosity and permeability in the medium without any microbeads, $\phi_t$ is the effective porosity of the treated medium (microbeads added) and $K_t$ is the permeability in the treated medium as given by Equation 21, using a pore radius given by Equation 22. More complex (and more realistic) distributions could be handled by numerical integration, but this simple distribution more clearly illustrates the basic principle that more compact distributions (due to higher concentrations of analyte) lead to greater flow restriction.

Figure 3:
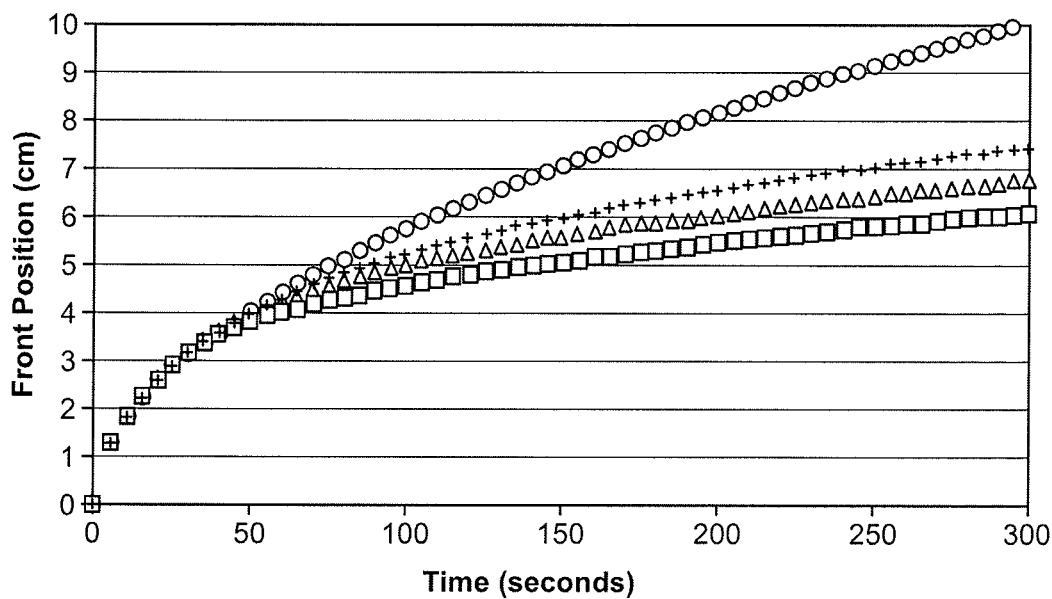

FIG. 3 shows the effects of changing viscosity on flowrate. As a simple model of coagulation, the viscosity in a treated arm of porous medium changes from $\mu_o$ to $\mu_f$ as the buffer front moves from $x_s$ to $x_f$. All other parameters stay the same. The viscosity is therefore:

$$\mu(\lambda < x_s) = \mu_o \tag{24a}$$

$$\mu(x_s < \lambda < x_f) = \mu_o(1 + a(\lambda - x_s)) \tag{24b}$$

$$\mu(\lambda > x_f) = \mu_f \tag{24c}$$

where $$a = \frac{1(\mu_f - \mu_o)}{\mu_o(x_f - x_s)} \tag{25}$$

From Equation 17:

$$\beta(\lambda < x_s) = \frac{\mu_o \varphi}{\rho K}\lambda \tag{26a}$$

$$\beta(x_s < \lambda < x_f) = \frac{\mu_o \varphi}{\rho K}\left(\lambda + \frac{a}{2}(\lambda - x_s)^2\right) \tag{26b}$$

$$\beta(\lambda > x_f) = \frac{\varphi}{\rho K}\left(\mu_o x_s + \frac{1}{2}(\mu_f + \mu_o)(x_f - x_s) + \mu_f(\lambda - x_f)\right) \tag{26c}$$

Greater values of $x_f$-$x_s$ simulate longer coagulation times. In FIG. 3, the circles show flow without any change in viscosity. All others show change in viscosity from 1 centipoise to 10 centipoise. The change in viscosity starts at 30 mm for all runs. For the crosses, viscosity reaches its maximum of 10 centipoise at 90 mm. For the triangles, the maximum viscosity is reached at 60 mm. For the squares, the maximum viscosity is reached at 40 mm. More realistic models for coagulation would necessarily be more complex, likely involving numerical integration of the $\beta$ term in Equation 17.

Stopped Flow Device

The device provided herein includes the following physical elements that can be adhered in a layered format to generate the assembled device: a proximal bottom, proximal housing, proximal cover, vertical conduit, indicator housing, indicator strip and distal top portion. Without being bound by a particular mechanism or configuration, the elements thus assembled can create within the device a fluid pathway as follows: a proximal well for receiving a blood sample which is in fluid communication with a volumetric capillary reservoir for transfer of the sample to the underside of a vertical conduit via a distal exit orifice, and a point of contact between the top of the vertical conduit and the proximal end of the indicator strip.

a. Overall Configuration and Dimensions

The dimensions of the device provided herein can range from about 0.125 to about 0.15, 0.2, 0.3, 0.5, 0.8, 1, 1.5, 2, 2.5 or 3 inches wide and about 0.5 to 1, 2, 3, 4, 5, 6, 7, 8, 9 or 10 inches long. In one embodiment, the device is 0.787 inches wide by 3.0 inches long. In an exemplary embodiment, an assembled device is rectangular in shape with rounded proximal and distal ends.

The outer housing of an exemplary device provided herein is a rigid material. Any one of a number of rigid materials known to those of skill in the art can be used, including, but not limited to, acrylonitrile butadiene styrene (ABS), Black (CYCLOLAC® MG47-BK4500); acrylonitrile butadiene styrene (ABS), Black (LUSTRAN® 433-904000); acrylonitrile butadiene styrene (ABS), Black (POLYLAC® PA-765); acrylonitrile butadiene styrene (ABS), Black (POLYLAC®

PA-746); acrylonitrile butadiene styrene (ABS), Light Grey (Platable) (LUSTRAN® PG 298-703693); acrylonitrile butadiene styrene (ABS), Natural (LUSTRAN® 433-000000); acrylonitrile butadiene styrene (ABS), Natural (POLYLAC® PA-765 (Natural)); acrylonitrile butadiene styrene (ABS), Sno White (LUSTRAN® 348-012002); acrylonitrile butadiene styrene (ABS), White (LUSTRAN® 248-SB02664900); acrylonitrile butadiene styrene (ABS), Black 30% Glass Fiber (RTP 600 605); polycarbonate/acrylonitrile-butadiene-styrene (PC/ABS), Black (CYCOLOY® C1200HF-701); polycarbonate/acrylonitrile-butadiene-styrene (PC/ABS), Black (CYCOLOY® C2950-701); polycarbonate/acrylonitrile-butadiene-styrene (PC/ABS), Black (BAYBLEND® FR 110-901510); polycarbonate/acrylonitrile-butadiene-styrene (PC/ABS), Black (BAYBLEND® T85-901510); polycarbonate/acrylonitrile-butadiene-styrene (PC/ABS), Natural (BAYBLEND® FR 110-000000); polycarbonate/acrylonitrile-butadiene-styrene (PC/ABS), Natural (BAYBLEND® T65-000000); polycarbonate/acrylonitrile-butadiene-styrene (PC/ABS), Natural (CYCOLOY® C6800-111); acetal polyoxymethylene (POM), Black 10% Glass Bead (RTP 800 GB 10); acetal polyoxymethylene (POM), Black 20% Glass Bead (RTP 800 GB 20); acetal polyoxymethylene (POM) copolymer, Black (CELCON® M90 CD3068); acetal polyoxymethylene (POM) copolymer, Natural (CELCON® M90 CF2001); acetal homopolymer, Black (DELRIN® 500 CL BK601); acetal homopolymer, Black (DELRIN® 500 P BK602); acetal homopolymer, Natural (DELRIN® 500P NC010); poly(methyl methacrylate) (PMMA) i.e. acrylic, Clear (PLEXIGLAS® V052-100); engineering thermoplastic polyurethane resin (ETPU), Natural (ISOPLAST® 202EZ); high density polyethylene (HDPE), Natural (MARLEX® 9006); liquid crystal polymer (LCP), Black 30% Glass Fiber (VECTRTA® E130i); low density polyethylene (LDPE), Natural (DOW™ LDPE 722); linear low density polyethylene (LLDPE), Natural (DOWLEX™ 2517); Nylon 6 (polyamide 6), Natural 15% Glass Fiber (ZYTEL® 73G15L NC010); Nylon 6/12 (polyamide 6/12), Black 33% Glass Fiber (ZYTEL® 77G33L BK031); Nylon 66 (polyamide 66), Black (ZYTEL® 101L BKB009); Nylon 66 (polyamide 66), Black (RTP 200 UV); Nylon 66 (polyamide 66), Black (HYLON® Select N1000EHL); Nylon 66 (polyamide 66), Natural (ZYTEL® 103 HSL); Nylon 66 (polyamide 66), Natural (ULTRAMID® 1000-2); Nylon 66 (polyamide 66), Black 13% Glass Fiber (ZYTEL® 70G13 HS1L BK031); Nylon 66 (polyamide 66), Black 13% Glass Fiber (HYLON® Select N1013HL); Nylon 66 (polyamide 66), Natural 13% Glass Fiber (ZYTEL® 71G13L); Nylon 66 (polyamide 66), Natural 13% Glass Filled (ZYTEL® 70G13 HS1L NC010); Nylon 66 (polyamide 66), Black 14% Glass Fiber (ZYTEL® 8018HS BKB085); Nylon 66 (polyamide 66), Black 20% Glass Fiber (RTP 200 203 FR); Nylon 66 (polyamide 66), Black 33% Glass Fiber (ZYTEL® 70G33 HS1L BK031); Nylon 66 (polyamide 66), Black 33% Glass Fiber (HYLON® Select N1033HL); Nylon 66 (polyamide 66), Natural 33% Glass Fiber (ZYTEL® 70G33 HSIL NC010); Nylon 66 (polyamide 66), Black 40% Mineral Reinforced (MINLON® 10B40 BK061); Nylon 66 (polyamide 66), Black Impact Modifier, Rubber (ZYTEL® ST-801 BK010); Nylon 66 (polyamide 66), Natural Impact Modifier, Rubber (ZYTEL® ST-801 NC010); polybutylene terephthalate (PBT), Black (VALOX® 357-BK1066); polybutylene terephthalate (PBT), Black (CRASTIN® S610 same as 600F20BK810); polybutylene terephthalate (PBT), Black (VALOX® 364-BK1066); polybutylene terephthalate (PBT), Natural (VALOX® 357-1001); polybutylene terephthalate (PBT), Black 30% Glass Fiber (VALOX® 420SEO-BK1066-BG); polybutylene terephthalate (PBT), Natural 30% Glass Fiber (VALOX® 420 SEQ Nat 1001); polycarbonate (PC), Black (LEXAN® 940-701); polycarbonate (PC), Black (MAKROLON® 2405-901510); polycarbonate (PC), Clear (MAKROLON® 2458-550115); polycarbonate (PC), Clear (LEXAN® HP1-112); polycarbonate (PC), Infrared (LEXAN® 121 S-80362); polycarbonate (PC), Smoke (RTP 300 399X71833 S-94450); polycarbonate (PC), Natural 10% Glass Fiber (RTP 300 301); polycarbonate (PC), Natural 20% Glass Fiber (LEXAN® 3412R-131); polycarbonate/polybutylene-terephthalate (PC/PBT), Black (XENOY® 6620-BK1066); polyethylene terephthalate (PET), Black 30% Glass Fiber (RYNITE® 530-BK503); polyethylene terephthalate (PET), Black 35% Glass Mica Low Warp (RYNITE® 935 BK505); polyethylene terephthalate (PET), Black 45% Glass Mineral Flame Retardant (RYNITE® FR 945 BK507); polyethylene terephthalate glycol (PETG), Clear (EASTAR™ 6763); polypropylene (PP), Natural (RTP Anti-static Permastat 100); polypropylene (PP) homopolymer, Black (MAXXAM® FR PP 301BLK1284-11S); polypropylene (PP) homopolymer, Natural (PRO-FAX® 6323); polypropylene (PP) homopolymer, Natural (PRO-FAX® 6523); polyphthalamide (PPA), Natural 35% Glass Fiber (ZYTEL® HTN 51G35HSL); polyphenylene-ether/polystyrene (PPE/PS), Black (NORYL® 731-701); polyphenylene-ether/polystyrene (PPE/PS), Black (NORYL® N300X-701); polyphenylene-ether/polystyrene/polyamide (PPE/PS/Nylon), Black 10% Glass Fiber (NORYL® GTX GTX810-1710); polyphenylene sulfide (PPS), Black 40% Glass Fiber (RYTON® R-4-02); polyphenylene sulfide (PPS), Natural 40% Glass Fiber (RYTON® R-4); polyphenylsulfone (PPSU), Natural Transparent Amber (RADEL® R-5000 NT); general purpose polystyrene (GPPS), Clear (STYRON™ 666DW2); high impact polystyrene (HIPS), Natural (STYRON™ 498); polysulfone (PSU), Natural (UDEL® P-3703 NT 11); styrene butadiene (SB), Clear (K-RESIN® KR01); thermoplastic elastomer (TPE), Black (SANTOPRENE® 101-64); thermoplastic elastomer (TPE), Black (SANTOPRENE® 101-73); thermoplastic elastomer (TPE), Black (SANTOPRENE® 111-35); thermoplastic elastomer (TPE), Black (SANTOPRENE® 111-45); thermoplastic elastomer (TPE), Black (Santoprene 111-55); thermoplastic elastomer (TPE), Black (SANTOPRENE® 111-87); thermoplastic elastomer (TPE), Natural (SANTOPRENE® 211-45); thermoplastic elastomer (TPE), Natural (SANTOPRENE® 211-64); thermoplastic elastomer (TPE), Natural (SANTOPRENE® 251-70W232); thermoplastic polyurethane elastomer (polyester) (TPU-Polyester), Natural (TEXIN® 245); and thermoplastic polyurethane elastomer (polyether) (TPU-Polyether), Natural (TEXIN® 985-000000).

The outer housing forming the top of the device also can include an opening for air escape. A portion of the top of outer housing can be positioned above the narrow midsection of the indicator strip to facilitate visualization of the interface of the separated blood cell and plasma following migration through the strip. Additional portions of the top of the outer housing can include proximal and distal windows positioned above the proximal and distal wide ends of the indicator strip, which provide visual indications of successful migration of blood through the strip. The portion(s) can have relieved windows to view the indicator strip and the proximal and distal lobes. Alternatively, the portion(s) can be a transparent solid material through which the indicator strip and proximal and distal lobes can be viewed. Exemplary transparent, solid materials that can be used are known to those of skill in the art and include, but are not limited to, general purpose polystyrene (GPPS), Clear (STYRON™ 666DW2); polyethylene terephthalate glycol (PETG), Clear (EASTAR™ 6763); polycarbonate (PC), Clear (MAKROLON® 2458-550115); and poly (methyl methacrylate) (PMMA) i.e. acrylic, Clear (PLEXIGLAS® V052-100).

b. Proximal Bottom

The Proximal Bottom creates the closure for a volumetric capillary reservoir as well as provides a surface for the blood sample to be applied. The proximal bottom is a solid, thin, rigid material having an outer surface and an inner surface. Such materials are known to those of skill in the art and include, but are not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). The thickness of the material can range from about 0.003 inches to about 0.005, 0.007, 0.008, 0.01, 0.015, 0.0175 or 0.020 inches. In some embodiments, the thickness is 0.010 inches. The outer surface of the proximal bottom provides the outer-facing, solid base of the device, whereas the opposite, or inner, surface provides the inner-facing bottom of the device. The inner-facing bottom serves as a bottom of a volumetric capillary reservoir and can also provide a surface for the fluid sample to be applied. In an exemplary embodiment, the fluid sample to be applied is blood. The fluid sample application area of the inner surface of the proximal bottom can be coated with materials that facilitate preservation, migration or other property of the fluid (for example, when the fluid is blood, the inner surface of the proximal bottom can be coated with heparin or other clotting inhibitor to inhibit clotting of the blood sample, and/or a buffer such as polysorbate 20 (i.e. Tween-20®) to promote migration of blood into the volumetric capillary reservoir).

c. Proximal Housing

The Proximal Housing is bonded to the Proximal Bottom. The Proximal Housing sets the volume for the capillary reservoir and directs the fluid sample to the distal exit of the volumetric capillary reservoir. The Proximal Housing also contains a thin, rigid material as described for the Proximal Bottom, and in a range of thickness as described for the Proximal Bottom. In an exemplary embodiment, rigid Polyvinyl Chloride can be used as the material, at a thickness of about 0.020 inches. The material in some embodiments is inert to the fluid, such as blood; exemplary materials include plastic, glass and metal. The material can be prepared, coated, or covered in a way to prevent the fluid, such as blood, from travelling across it and instead traveling exclusively within the strip to facilitate proper separation. Any coating known to those of skill in the art to create a hydrophobic surface, such as an adhesive, can be used. In some embodiments, the size and shape of the Proximal Housing are similar to or the same as those of the Proximal Bottom.

The Proximal Housing includes a hole in the shape of a tear drop of about 0.1, 0.2, 0.3, 0.4, 0.5, 0.55, 0.575, 0.576, 0.6, 0.7, 0.75, 0.8, 0.9 or 1.0 inch long, center to center. In one embodiment, the tear drop-shaped hole is 0.576 inch long, center to center, with the wide end of the tear drop positioned proximally compared to the position of the narrow end of the tear drop. The Proximal Housing can be adhered to the Proximal Bottom using adhesive transfer tape, glue or other adhesive known to those of skill in the art. Once adhered to the Proximal Bottom, the edges of the hole in the Proximal Housing provide the walls of a volumetric capillary reservoir and set the volume for the reservoir. The volume of the reservoir can be in a range of about 1 microliter to about 5, 10, 15, 20, 25, 30, 35, 40, 45, 50, 55, 60, 65, 70, 75, 80, 85, 90, 95 or 100 microliters or more. In some embodiments, the volume of the reservoir is from about 25 to about 30, 31, 32, 33, 34, 35, 36, 37, 38, 39 or 40 microliters.

The capillary reservoir can include any surface that permits the fluid, such as blood, to pass over it. In some embodiments, when the fluid is blood, the surface is hydrophilic, or hydrophobic with a coating that renders it hydrophilic. The capillary reservoir can also be replaced with a porous material that the blood can soak into, as long as the pore size is large enough to prevent blood cells (~1-8 μm particle size) from separating from plasma before entering the separation medium (indicator strip) (e.g., porous material of pore size of 20 um or more in diameter). In some embodiments, the capillary reservoir is not present and the fluid, such as blood, is directly applied to the strip.

The wide, circular end of the tear drop shape of the reservoir can be used to deliver the fluid to the device. The edges of the reservoir and the portion of the proximal cover that caps the volumetric capillary reservoir can be coated with substance or solutions that inhibit degradation of the fluid and/or promote migration of the fluid. In an exemplary embodiment, when the fluid is blood, the coating can be heparin and/or a buffer such as polysorbate 20 (i.e. Tween-20®) solution to inhibit clotting of the blood and to promote migration of blood into the volumetric capillary reservoir.

d. Proximal Cover

The Proximal Cover is bonded to the Proximal Housing. The Proximal Cover caps the volumetric capillary reservoir and provides the distal exit orifice. The distal exit is sized and located to promote capillary wicking into the Vertical Conduit. The Proximal Cover contains a thin, rigid material known to those of skill in the art and as described in regard to the Proximal Bottom and the Proximal Housing. Such materials can include styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). In some embodiments, the material is rigid Polyvinyl Chloride.

The thickness of the Proximal Cover can range from about 0.003 inches to about 0.005, 0.007, 0.008, 0.01, 0.015, 0.0175 or 0.020 inches. In some embodiments, the thickness is 0.010 inches. In other embodiments, the size and shape of the proximal cover can be similar to or about the same as those of the proximal housing. The Proximal Cover contains two holes; the first hole is circular in the shape of about 0.2, 0.3, 0.4, 0.5, 0.6, 0.7, 0.8, 0.9 or 1.0 inches in diameter and is positioned proximally with respect to the second hole. In some embodiments, the second hole is smaller than the first (proximal) hole; in one embodiment, it is less than about 0.2 inches in diameter and is about 0.1, 0.125, 0.15, 0.175, 0.18 or 0.19 inches in diameter. The Proximal Cover is adhered to the Proximal Housing, using adhesive transfer tape, glue or other adhesives known to those of skill in the art such that the larger, proximal, circular hole is positioned over the wide, circular end of the tear drop shape of the reservoir formed by the Proximal Housing. In some embodiments, the portion of the Proximal Cover that caps the volumetric capillary reservoir and edges of the reservoir can be coated with substances or solutions that inhibit degradation of the fluid and/or promote migration of the fluid into the volumetric capillary reservoir. In an exemplary embodiment, the fluid is blood and the coating can be heparin and/or a buffer such as polysorbate 20 (i.e. Tween-20®) solution to inhibit clotting of the blood and promote migration of blood into the volumetric capillary reservoir.

Once adhered, the Proximal Cover caps the volumetric capillary reservoir, leaving a circular opening for the blood sample delivery reservoir. The smaller, distal circular hole in the Proximal Cover provides the distal exit orifice of the volumetric capillary reservoir. The distal exit orifice is sized and located to promote capillary wicking of blood into the vertical conduit.

e. Vertical Conduit

The Vertical Conduit in one exemplary embodiment of the device is a polyethylene dry blend surfactant (DBS) filter. In embodiments in which the fluid to be analyzed is whole blood, the vertical conduit can be a material, such as a glass fiber filter (e.g., Millipore AP25), capable of separating cells from fluid (i.e., plasma or serum) in a vertical orientation, if such separation is desired. A particular polyethylene filter that can be used is Porex x4897 polyethylene dry blend surfactant (DBS) disk (3/16 inch diameter) with the following specifications can be used: 15-45 µm pore size; 1/16 inch thickness (Porex, Fairburn, Ga., U.S.A.). A semicircular or crescent shape is used to make the distance from any point on the distal edge of the vertical conduit and the proximal edge of the resolving region of the indicator strip consistent. This promotes the fluid front to converge at the resolving region of the indicator strip.

The Vertical Conduit can be a glass fiber filter or any material that is the proper density (e.g., at about a 2-3 um pore size) that does not degrade the analyte and/or other fluid components (e.g., if the analyte is a cell, the material should not or should minimally effect cell lysis). Exemplary materials include glass, paper made from coated cellulose, cotton and synthetic fibers, or blends of various fiber materials) known to those of skill in the art. Glass is common because it induces particularly minimal cell lysis.

The Vertical Conduit, in some embodiments, is of a semicircular (crescent) shape that can be used to make the distance from any point on the distal edge of the vertical pad and the proximal edge of the resolving region of the indicator strip consistent. This promotes the fluid front to converge at the resolving region of the indicator strip. In other embodiments, the shape of the filter suitable for this purpose can include, but is not limited to, half circles, rectangles, triangles and other geometric shapes known to those of skill in the art. In general, better separation is effected with wider rather than longer Vertical Conduits.

In some embodiments, the conduit need not be a distinct material; rather, the housing can be etched to create channels through which the fluid travels. Without being bound by any theory, capillary forces within the etched channels could induce migration of the fluid, such as blood, within the channels. The size of the channels can be empirically designed based on the differential separation to be effected between the particulate analyte of interest and the remaining components of the fluid. In some embodiments, the surfaces of the channels can be prepared, coated, or covered in a way to prevent the fluid, such as blood, from travelling across it and instead traveling exclusively within the strip to facilitate proper separation. Any coating known to those of skill in the art to create a hydrophobic surface, such as an adhesive, can be used.

f. Indicator Housing

The Indicator Housing is bonded to the Proximal Cover and provides a minimal internal volume around the separation components. This prevents humidity and other environmental variables from affecting fluid migration characteristics in the device. The Indicator Housing is made from a thin rigid material known to those of skill in the art and including, but not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). In some embodiments, rigid Polyvinyl Chloride is used. The thickness of the material can range from about 0.038 inches to about 0.042 inches; in some embodiments, the thickness is 0.040 inches. The size and shape of the Indicator Housing are similar to or the same as those of the Proximal Cover.

The Indicator Housing has two holes; one hole is circular in the shape of about 0.1, 0.2, 0.3, 0.4, 0.5, 0.6, 0.7, 0.8 0.9 or 1.0 inches in diameter and is positioned proximally with respect to the second hole. The second hole has a shape similar or identical to the shape of the Indicator Strip (any shape having a linear section). In an exemplary embodiment, the Indicator Housing has a narrow rectangular midsection about 0.1, 0.15, 0.2, 0.25, 0.3, 0.35, 0.4, 0.45 or 0.5 inches wide and 3, 3.5, 4, 4.5, or 5 inches long and about 0.5 inch to 1.0 inch diameter wide circular ends.

The Indicator Housing is adhered to the Proximal Cover (using adhesive transfer tape, glue or other adhesives known to those of skill in the art) such that the circular proximal hole in the Housing is positioned directly above the circular proximal hole in the Proximal Cover. In positioning the Indicator Housing in this way, the Vertical Conduit is located in, and perpendicular to the plane of, the proximal wide circular end of the second (dumbbell or other shape with wide ends flanking a narrow midsection) hole. The Indicator Housing provides a minimal internal volume around the separation components. This prevents humidity and other environmental variables from affecting fluid migration characteristics in the device.

Alternate Embodiment of the Indicator Housing

In one embodiment, the Indicator housing can be designed to compress the indicator strip between two layers of adhesive (adhesive transfer tape such 3M's 467 MP 2.3 mils adhesive transfer tape, glue or other adhesive known to those of skill in the art)-coated rigid material. Types of rigid materials include, but are not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). In one embodiment, the material is Rigid Poly Vinyl Chloride. The thickness can range from about 0.1 to about 0.11, 0.12, 0.13, 0.14, 0.15, 0.16, 0.17, 0.18, 0.19, 0.20, 0.21, 0.22, 0.23, 0.24 or 0.25 inches. In one embodiment, the thickness is from about 0.019 inches to about 0.021 inches. In another embodiment, the material is Rigid Poly Vinyl Chloride and the thickness is 0.020 inches. The compression can minimize variability in the thickness of the Indicator Strip material, thereby controlling the volumetric uptake of the fluid, such as blood. The size and shape of the Indicator Housing are the same as those of the Proximal Cover.

In one embodiment, there are two openings in the Indicator Housing; the first is a circular opening of about 0.5 inches in diameter. The second opening is positioned distally in respect to the first opening, and is in the shape of a dumbbell having a narrow rectangular midsection 0.25 inches wide and 0.75 inches long, with 0.5 inch diameter wide circular ends. In this manifestation, the Indicator Housing with the dumbbell-shaped opening is constrained to a thickness equal to or slightly less than the nominal thickness of the indicator strip, thereby compressing the indicator strip to a defined thickness. In one embodiment, this thickness is about 0.012 inches. The proximal end of the dumbbell opens downwardly towards the proximal hole to provide a continuous space for the Vertical Conduit while maintaining face to face contact between the Vertical Conduit and the Indicator Strip. This vertical shaft descending down from the proximal end of the dumbbell shaped opening is a half circle to full circle in shape, having a shared proximal surface from the dumbbell above. In one embodiment, this opening is slightly larger than a half moon at 0.35 inches long. Similar to other manifestations, the Indicator Housing is adhered using 3M's 467 MP 2.3 mils or other adhesive transfer tape, glue or other adhesive known to those of skill in the art to the Proximal Cover such that the circular proximal hole in the cover is positioned directly above the circular proximal hole in the Indicator Housing.

g. Indicator Strip

The indicator strip is a lateral flow porous membrane made of three separate, but overlapping materials. Specifically, from the proximal to the distal end of the indicator strip, the following three materials are used: Ahlstrom 8975 (a borosilicate glass fiber with a PVA binding (polyvinylalcohol) with a thickness of 355-508 μm and water absorption of 19 μl/cm$^2$; Ahlstrom, Helsinki, Finland), blocked Pall Vivid 170 polyester-backed nitrocellulose (180 μm thick, 150-225 sec/4 cm capillary speed for water and 45-59 μg/cm2 protein (BSA) binding capacity; Pall Corporation, Port Washington, N.Y.), and Whatman LF1 (a 247 μm-thick, PVA-treated glass fiber paper that retains particles larger than 2 μm; Whatman, N.J., U.S.A.). The strip is rectangular in shape, following the shape of the second hole of the indicator housing. The width of the strip is 2 mm, and the overall length of the strip is 78 mm as follows, from proximal to distal ends (with a total of 4 mm overlap): Ahlstrom 8975 (20 mm length), Pall Vivid 170 (15 mm length) and Whatman LF1 (47 mm length). To construct the strip, strip components are assembled against a standard lateral flow backing (a PVC sheet with adhesive coating on one side). First, the Vivid 170 filter is blocked with 1 mg/ml neutravidin in PBS for 1 hour at room temperature, then washed twice for 5 minutes each time in PBS, rinsed twice with water and allowed to dry overnight on the benchtop. The filter is coated with neutravidin to focus the point where any aggregated particles of biotin-neutravidin traveling with the sample fluid through the indicator strip would arrest in the strip in order to produce a tighter blockage in the strip that lets less fluid through. Fluid samples without neutravidin analyte in solution do not show visibly arrested particles along the neutravidin-coated strip. The components are laid down with Vivid 170 being first pressed against the backing (with its own backing in contact with the device backing). The Ahlstrom 8975 and LF1 are then laid down with 2 mm of overlap over each end of the Vivid 170 strip. The Ahlstrom 8975 filter is allowed to overhang the adhesive backing by 5 millimeters.

Using 3M's 467 MP 2.3 mil. adhesive transfer tape, the indicator strip is adhered to the bottom surface of the distal top which, as described herein, also forms the top of the device with its outer, top surface. Thus, the strip is pressed to the underside of the roof of the device so that the strip is sandwiched between the roof of the device and the backing. The distal top, with the indicator strip and its backing adhered to its bottom surface, is adhered using 3M's 467 MP 2.3 mil. adhesive transfer tape to the indicator housing such that the indicator strip is positioned within the second hole (i.e., the rectangular cutout) of the indicator housing thereby creating a sealed internal volume housing the indicator strip. The indicator strip is thus contained in a space wherein the bottom, or floor, of the space provided by the proximal cover serves as a base for the strip, the rectangular hole in the indicator housing provides the walls of the space around the strip and the bottom surface of the distal top provides the roof of the space. The most proximal end of the overhang of the Ahlstrom 8975 filter of the indicator strip is situated above and in contact with the top of the vertical conduit which is adhered on the proximal cover. An optional distal pad can be included at the distal end of the indicator strip to provide a sink to collect excess sample fluid in the event that capillary flow of the fluid is not stopped in the indicator strip. If an analyte (e.g., neutravidin) is present in the sample fluid at sufficient concentration, a flow-modifying agent (e.g., LPA Biotin) that would be added to the sample prior to migration of the fluid through the medium binds with the analyte (e.g., neutravidin) to form a cross-linked network in which latex beads (which can also be added to the sample before migration through the strip) become entrapped thereby blocking the pores of the strip and causing flow of the sample to stop. The amount of blockage of flow in the filters is directly proportional to the amount of analyte in the sample. Therefore, if the fluid front does not move past a specified position in the strip in a specified amount of time after sample fluid addition, this indicates that the concentration of the specific analyte in the sample fluid is above a threshold value.

In some embodiments of the device, a solution prepared by solubilizing dry bromophenol blue (BPB) into 95% ethanol at 10 mg/ml [weight-to-volume (w/v)] can be applied onto the center of the distal pad (or distal end) of the indicator strip and allowed to dry for 5 minutes. The blue color provides a visual indicator that fluid migrated to the distal pad of the indicator strip, indicating saturation of the strip.

h. Distal Top

The Distal Top is printed with graphics indicating the function of the device. The graphics represent the range of measurement of a parameter of interest associated with an analyte that has migrated in the Indicator Strip. In exemplary embodiments, the graphics represent INR (indicative of blood coagulation time). The range is determined based on the calibration of the device, which is described below.

The Distal Top is made of a thin rigid, transparent material such as, but not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET) The thickness of the material can range from about 0.003 inches to about 0.005, 0.007, 0.008, 0.01, 0.015, 0.0175 or 0.020 inches; in one embodiment the thickness is 0.010 inches. The Distal Top also includes an air escape opening of about 0.005, 0.01, 0.015, 0.02, 0.025, 0.03, 0.035, 0.04, 0.045 or 0.05 inches in diameter at the distal end of the Indicator Housing, allowing displaced air to escape as blood is drawn into the device. In one embodiment, the diameter of the air escape opening is about 0.020 inches in diameter.

One surface of the Distal Top forms the top of the device facing the exterior. The Indicator Strip is adhered (using adhesive transfer tape or other adhesives known to those of skill in the art) to the opposite, or bottom, surface of the Distal Top such that the narrow rectangular portion of the Indicator Strip aligned with the narrow rectangular transparent portion of the distal top and the proximal and distal windows aligned with the proximal and distal wide ends of the Indicator Strip, respectively. The windows facilitate visual observation of the presence of sufficient blood sample reaching the proximal end of the indicator strip and of successful migration of plasma through the strip to the point of saturation. The thus-formed Distal Top/Indicator Strip element was adhered (using adhesive transfer tape or other adhesives known to those of skill in the art) to the top surface of the Indicator House such that the Indicator Strip was positioned within the second hole of the Indicator Housing, thereby creating a sealed internal volume housing the Indicator Strip.

Split Flow Device

A split-flow device would be similar in design to a stopped-flow device described above, varying in the following aspects: (1) the sample would be introduced at the center of the linear indicator strip (2) the hole in the proximal housing, which houses the vertical pad and allows sample introduction, is oriented perpendicular to the linear indicator strip, as opposed to inline with the indicator strip (3) the vertical conduit is rectangular as opposed to being circular or semicircular. Such a device is described in Example 2. In other embodiments, the fluid paths can diverge radially from a single point, instead of being in diametrically opposite directions, or they can be applied to follow parallel paths.

Arc Flow Device

Example 3 describes the assembly of exemplary convergent pathway devices that can be used for qualitative or quantitative analysis of a component of a sample fluid based on comparison of migration distances (and thus, indirectly, a comparison of flow rates) of the fluid in modified and unmodified paths. The devices are assembled using components and specifications as described herein. The outer housing of an exemplary device is a rigid material that is solid on the bottom of the device and has an orifice on the top of the device for application of a fluid sample into a proximal well. In an exemplary embodiment, an assembled device is rectangular in shape with rounded proximal and distal ends. Seven separate physical elements are adhered in a layered format to generate the assembled device which can then be assembled into an outer housing. The elements thus assembled create within the device a fluid pathway as follows: a proximal well for receiving a fluid sample which is in fluid communication with a volumetric capillary reservoir for transfer of the sample to the underside of a vertical conduit via a distal exit orifice, and a point of contact between the top of the vertical conduit and a proximal portion of a ring of porous medium referred to as an indicator dial. In particular embodiments of the device, the ring of porous medium is oval (e.g., egg-shaped) or in the shape of a racetrack (i.e., having two parallel straight segments joined at each end by a rounded semicircle). In other embodiments of the device, the indicator dial is replaced with a linear rectangular indicator strip.

Relationship between Linear Flow and Circular ("Arc") Fluid Flow

Using Linear Lateral Flow Experiments to Predict ArcFlow Results

It is a simple matter to convert data obtained from linear strips into hypothetical results for circular strips. It is assumed that the position of the liquid front along a linear strip with time corresponds to the position along an arm in a circular strip. The presumed point of convergence between the two arms of the circular strip (treated and untreated) is found by plotting on the same graph both the front position versus time along a treated linear strip, and the circumference of the strip minus the front position versus time along an untreated linear strip. The point of convergence of these two plots yields both the expected position of the front convergence along the treated arm, and the expected time that this convergence occurs. This is illustrated in Example 6.

Exemplary Devices

Exemplary devices and methods for analyzing a fluid variable in a blood sample are now described. The method includes a process by which administered blood is exposed to a clotting initiating factor, such as Ca2+, then focused onto a graduated indicator strip that correlates cessation of fluid with impaired coagulation. The device includes an indicator along the test strip that indicates to the user that the blood has migrated the entire distance of the test strip thereby providing an indication that the test was successful. In addition, the device embodies an indicator along another portion of the test strip to indicate to the user when sufficient blood has been added.

Figure 4:
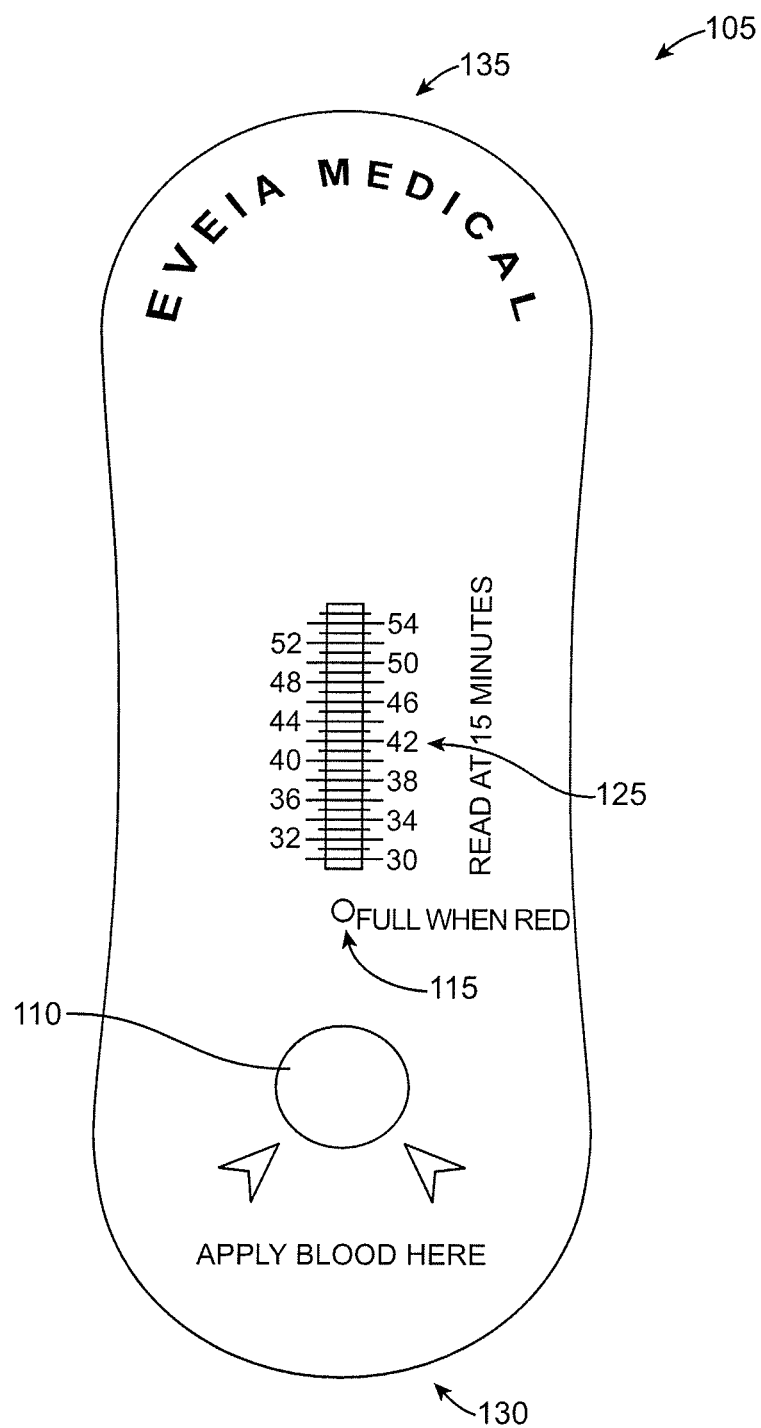

FIG. 4 shows a top view of an exemplary embodiment of the device 105. The device includes a well 110 that is configured to receive a sample of blood. One or more indicator windows are located on the device for providing relevant information to the user. For example, a first indicator window 115 provides an indication as to when a sufficient amount of blood has been applied to the device. A second indicator window 120 provides an indication as to whether the device has run correctly. The indicator windows can be configured to display a predetermined color (such as red or blue) or other indication to represent that a certain criteria has been satisfied. A graduated scale 125 is located on the front of the device to indicate the INR value or clotting time. The illustrated embodiment of the device generally has an elongated shape (from a proximal end 130 to a distal end 135) that is configured to be held by a user. It should be appreciated that the shape and size of the device may vary.

One or more labels may be provided on the device to provide any of a variety of information to the user. For example, a label 110 adjacent the well 110 includes language such as "Apply Blood Here" to indicate to the user that blood should be applied to the well 110. Any of a wide variety of other labels can be provided on the device.

Figure 6:
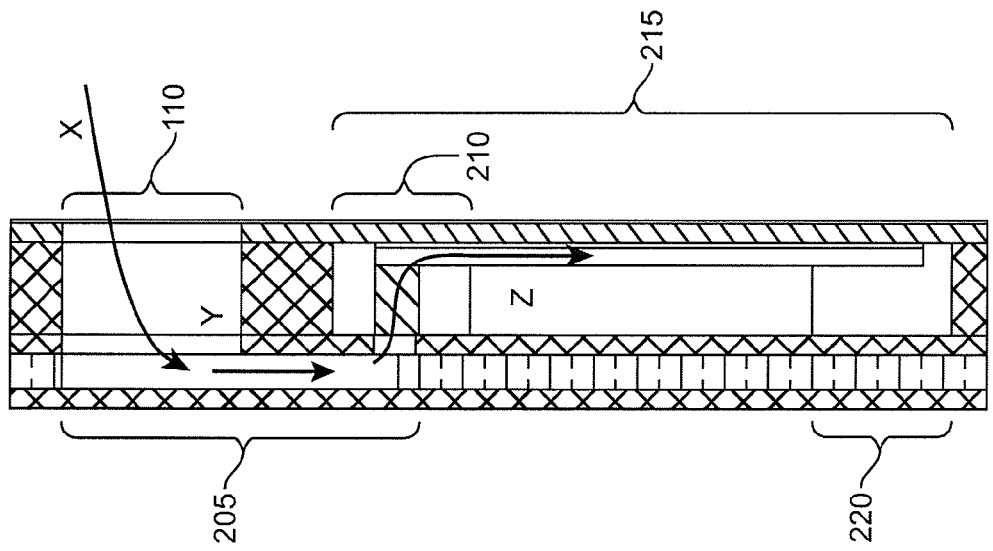
Figure 5:
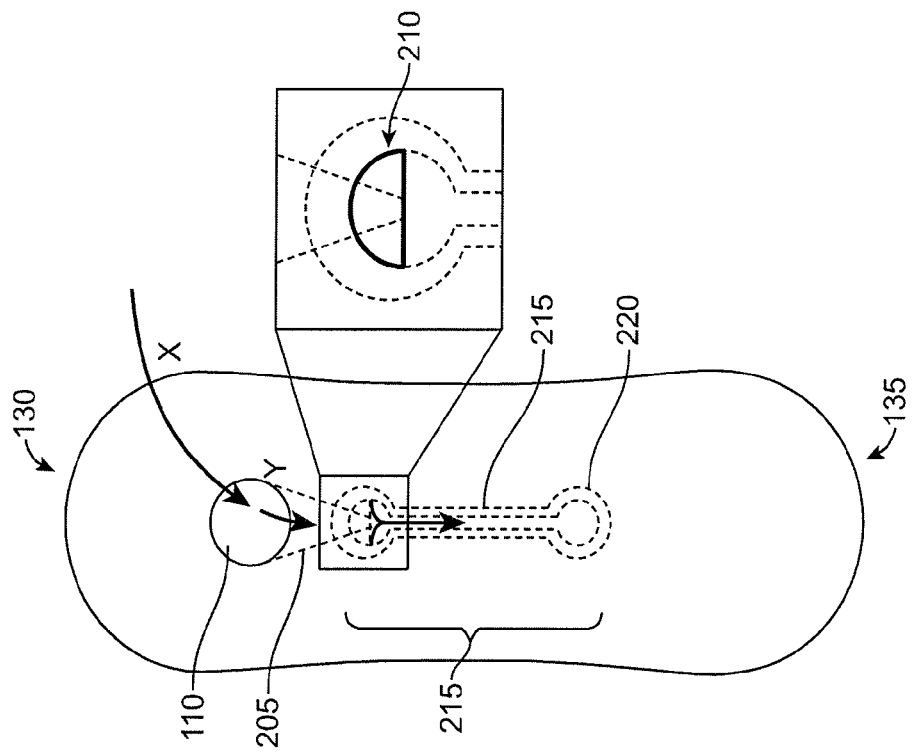

FIG. 5 shows a top view of the device 105 with a top cover removed. FIG. 6 shows a side, cross-sectional view of the device 105. The well 110 (which is configured to receive blood) forms an opening in the top of the device and extends downwardly toward the bottom of the device. As shown in FIG. 6, the bottom end of the well 110 communicates with a capillary reservoir 205 that extends from the well 110 toward the distal end 135 of the device. As shown in FIG. 5, the capillary reservoir tapers in size moving from the well in a distal direction.

The capillary reservoir 205 communicates with a vertical conduit 210 that provides a pathway for fluid to flow from the capillary reservoir 205 toward an elongated indicator strip 215 that is positioned at least partially above the capillary reservoir. The indicator strip 215 may be glass fiber filter paper. The indicator strip 215 extends distally along the length of the device and terminates at an excess volume reservoir 220 that is configured to receive and collect excess volume of fluid, as described more fully below. It should be appreciated that FIG. 6 is not drawn to scale. In an embodiment, the indicator strip is dye-free. The depth and relative sizes of various components may be exaggerated for clarity of illustration.

Figure 7:
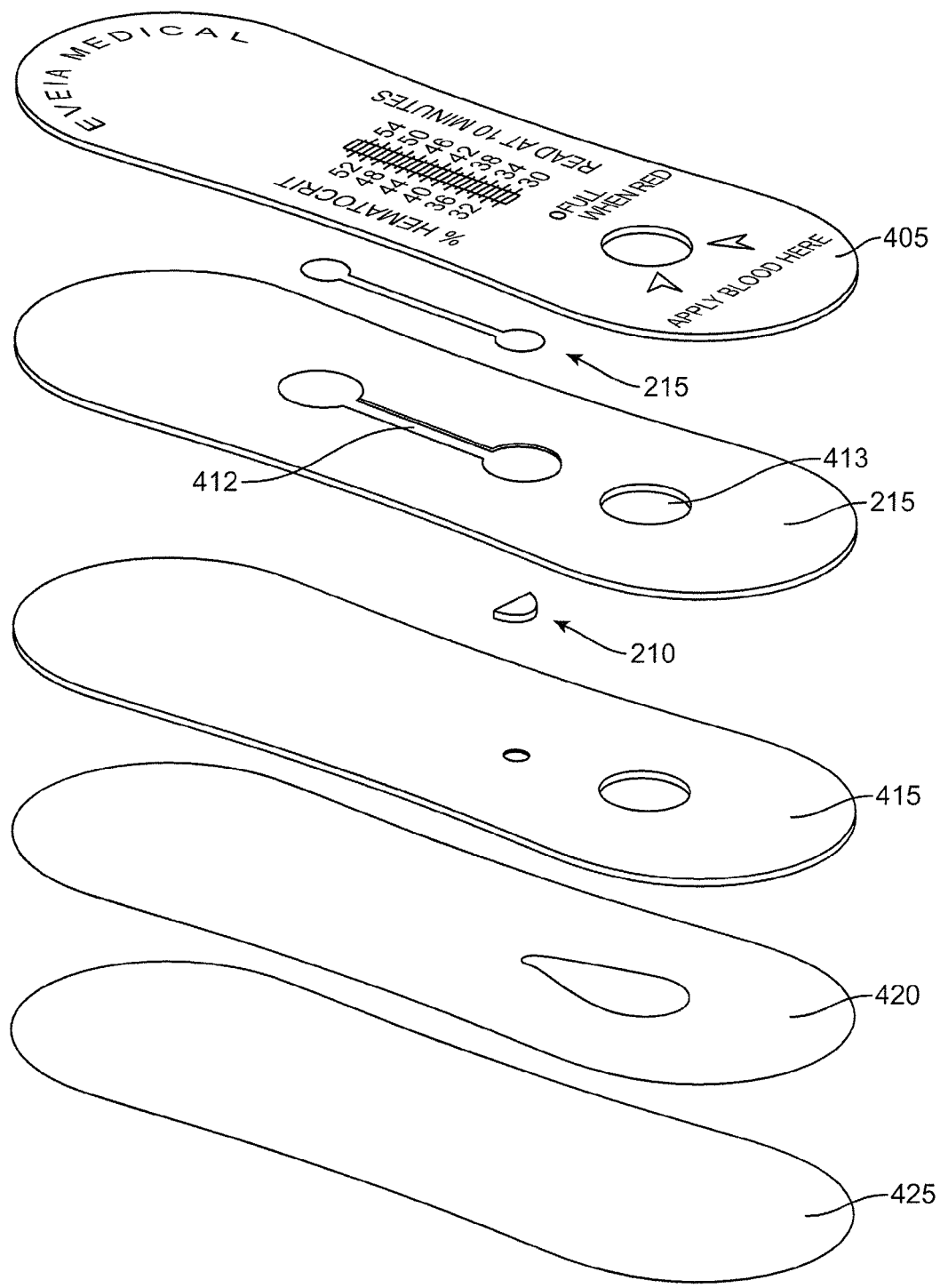

The device 105 may be formed of various components that are assembled to collectively form the device. FIG. 7 shows an exploded view of an exemplary set of layered components that form the device 105. It should be appreciated that the configuration of the components can vary and is not limited to what is shown in FIG. 7. A top cover 405 forms a top layer of the device. The indicator strip 215 is positioned immediately below and adjacent the top cover 405 such that the indicator strip 215 is adhered to the underside of the top cover 405. A middle layer 410 is positioned below the top cover 405 and includes a cut-out 412 that comprises an indicator housing around the separator components of the device. The vertical conduit 210 is sized and shaped to be positioned at least partially within the cut-out 412. The vertical conduit 210 is adhered to the top of a layer 415 such that it extends upwardly through the cut-out 412 and communicates with the indicator strip 215. An additional middle layer 420 is positioned below the layer 415 and above a bottom layer 425, which forms a base of the device. The layers may include various additional cut-outs that align with one another to form reservoirs and/or passageways of the device 105, such as, for example, the capillary reservoir 205, the well 110, and the excess volume reservoir 220.

Figure 8:
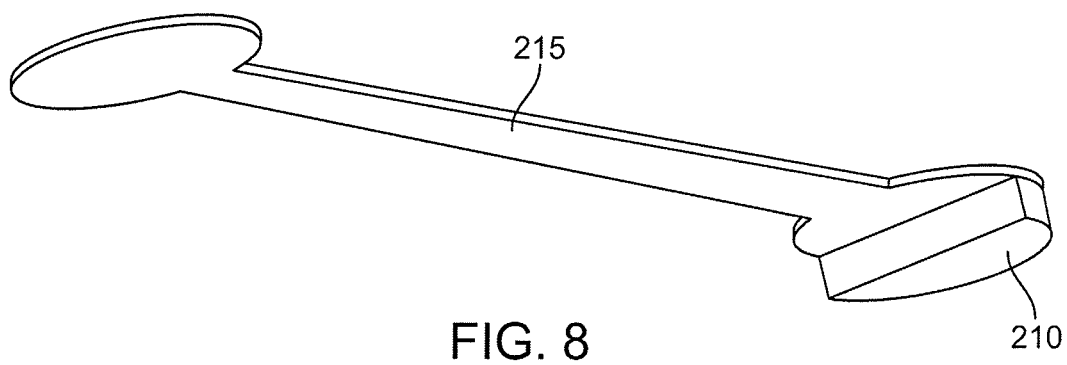

FIG. 8 shows an exemplary component that enables blood flow in the device 105. The component has a shape that is configured to resolve variations in flow rate or migration of the fluid front over a measurable distance. The vertical separator 210 is positioned at one end of the component. In an embodiment, the vertical conduit is crescent-shaped. The capillary reservoir forms a pathway between the vertical conduit 210 and a first end (proximal end) of the indicator strip 215. The opposite, second end (distal end) of the indicator strip 215 communicates with the excess volume reservoir 220.

An exemplary method of using the device is now described. A sample of blood is deposited into the well 110 via the opening on the top of the device. The blood sample application area may be coated with heparin to inhibit blood clotting and a mild solution (such as Tween-20® solution) to promote migration of blood into the volumetric capillary reservoir 205. Blood passes through the well (such as via adhesion properties) into the capillary reservoir 205, as represented by arrows X and Y in FIG. 6. The edges of the capillary reservoir 205 (or any other portion of the device) may be coated with heparin to inhibit blood clotting and a mild solution (such as Tween-20®) solution to promote migration of blood to the distal exit of the volumetric capillary reservoir.

From the capillary reservoir 205, blood flows to the underside of the vertical separator 210, where the blood is pulled upwardly (such as via capillary and bulk-flow properties) toward and onto the indicator strip 215. The vertical conduit 210 may be positioned and adhered over a distal exit orifice that controls blood flow so that blood can only enter the indicator region of the device via capillary action of the indicator strip and is therefore unable to flow around and avoid being properly resolved within the indicator strip. Blood migration through a vertical separation component has some inherent variability. The wide, proximal end of the lateral indicator strip 215 mitigates uneven flow of blood through the paper, allowing the blood front along the distal face of the vertical separator 210 to equalize.

The blood migrates in a proximal-to-distal direction down the indicator strip 215, as represented by arrow Z in FIG. 6. Blood flow along the indicator strip provides a coagulation rate-dependent resolution that can be visibly measured and read (graduated scale 125) as clotting times or INR values. Dry bromophenol blue may be present on the distal region of the indicator strip. The powdered dye becomes visibly blue upon contact with liquids including plasma. The blue color provides an easy indicator that blood has successfully migrated to the distal pad of the indicator strip, indicating a successful run. In an embodiment, the blue color can be observed through the window 120 (FIG. 4). The device may include an air escape opening allowing displaced air to escape as blood is drawn into the device.

In another embodiment, the housing of the device is configures such that the indicator strip 215 is compressed when positioned inside the housing. In this regard, the indicator strip 215 may be positioned between a pair of layers, such as adhesive-coated rigid material, that compress the indicator strip 215. In an embodiment, the adhesive layers are 467 MP 2.3 mils adhesive transfer tape (such as manufactured by 3M) and the rigid material is a material such asStyrene, propylene, Barex, PETG, Poly Vinyl Chloride and APET, for example. The thickness can range from 0.019 inches to 0.021 inches in one embodiment although the thickness may vary. In an embodiment, the thickness is 0.020 inches. The function of compression is to minimize variability in the thickness of the indicator strip material thereby controlling the volumetric uptake of blood.

The configuration of the device can be suited for the compressed indicator strip as follows. With reference again to FIG. 7, there are two openings in the layer 410. The first is a circular opening 413, which may be for example 0.5 inches in diameter. The second opening (the cut-out 412) is positioned distally relative to the first opening 413, and is in the shape of a dumbbell having a narrow rectangular midsection (such as on in a range of 0.25 inches wide and 0.75 inches long), with wide circular ends (such as having a diameter of around 0.5 inch). Unique to this embodiment, the indicator housing (i.e., layer 410) with the dumbbell-shaped cut-out 412 is constrained to a thickness equal to or slightly less than the nominal thickness of the indicator strip 215 (which may around 0.012 inches thick, for example) and is sandwiched between the top cover 405 and layer 415, thereby compressing the indicator strip 215 to a defined thickness. The proximal end of the dumbbell-shaped cut-out 412 opens downwardly towards the proximal hole 413 to provide a continuous space for the vertical separator 210 in layers 415 and 420 while maintaining face to face contact between the vertical separator 210 and the indicator strip 215. The vertical shaft descending down via the vertical separator 210 from the proximal end of the dumbbell shaped cut-out 412 is a half circle to full circle in shape, having a shared proximal surface from the dumbbell shaped cut-out 412. In an embodiment, this opening is slightly larger than a crescent or half moon at 0.35 inches long. The layer 410 (i.e., indicator housing) also serves to provide a minimal internal air space around the separation components, thereby minimizing the effects of humidity and other environmental variables on the blood migration characteristics in the device.

Figure 9A:
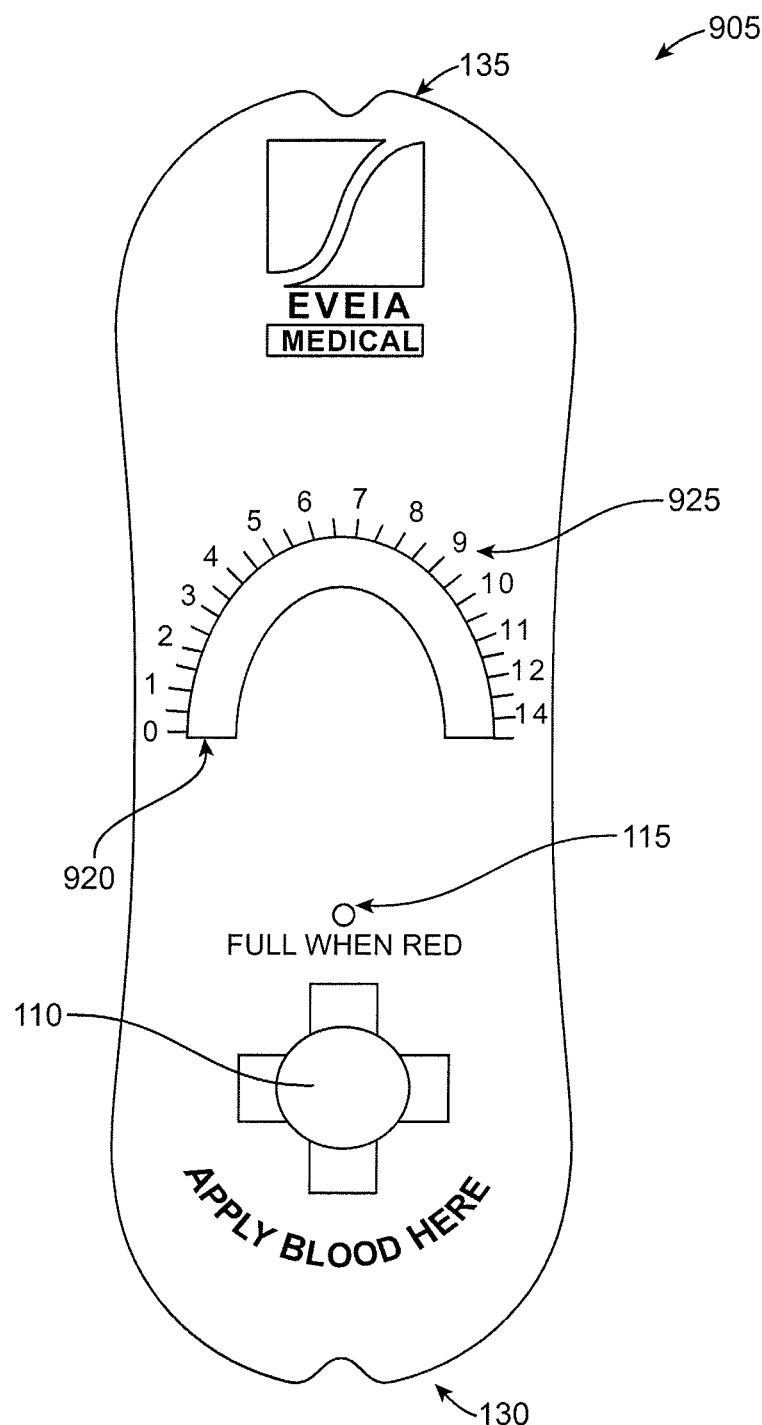
Figure 9B:
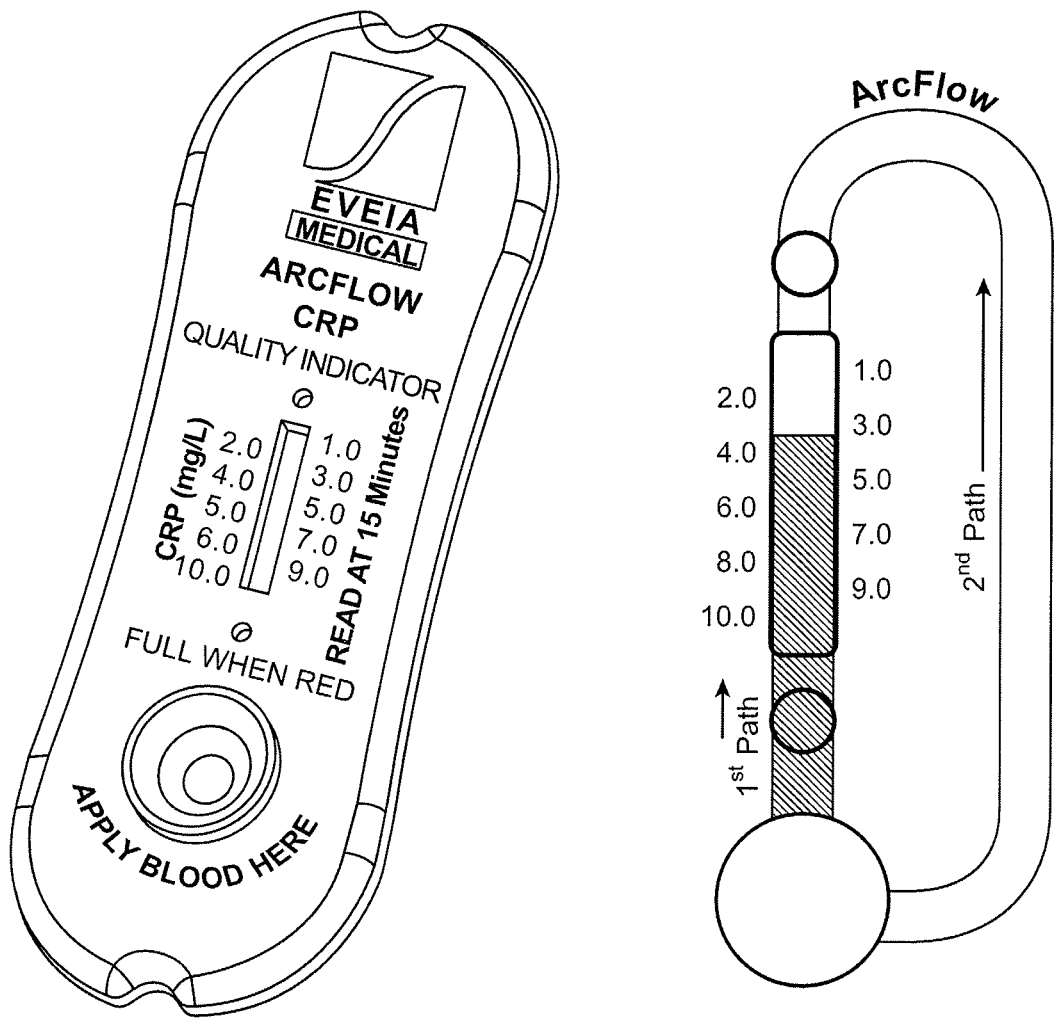

FIG. 9A shows a top view of another exemplary embodiment of the device, which is referred to using reference numeral 905. This embodiment is similar to the embodiment of FIG. 4. Like reference numerals refer to like structures between the embodiments of FIGS. 4 and 9A. The device includes a well 110 that is configured to receive a sample of blood. One or more indicator windows are located on the device for providing relevant information to the user. For example, a first indicator window 115 provides an indication as to when a sufficient amount of blood has been applied to the device. A second indicator window 920 provides an indication as to whether the device has ran correctly. In this embodiment, the second indicator window 920 has a curvilinear shape. For example, the embodiment of FIG. 9A has an arc or semicircular shape. Other closed circuit shapes, such as an oval, a rectangle with curved ends ("racetrack"), circular, semicircle, ellipse, etc.

The indicator windows can in some embodiments be configured to display a predetermined color (such as red or blue) or other indication to view a point of convergence of two fluid fronts. A graduated scale 925 is located on the front of the device to indicate a value, such as INR value or clotting time. The graduated scale has a shape that conforms or complements the shape of the indicator window 905. The illustrated embodiment of the device generally has an elongated shape (from a proximal end 130 to a distal end 135) that is configured to be held by a user. It should be appreciated that the shape and size of the device may vary.

Figure 11:
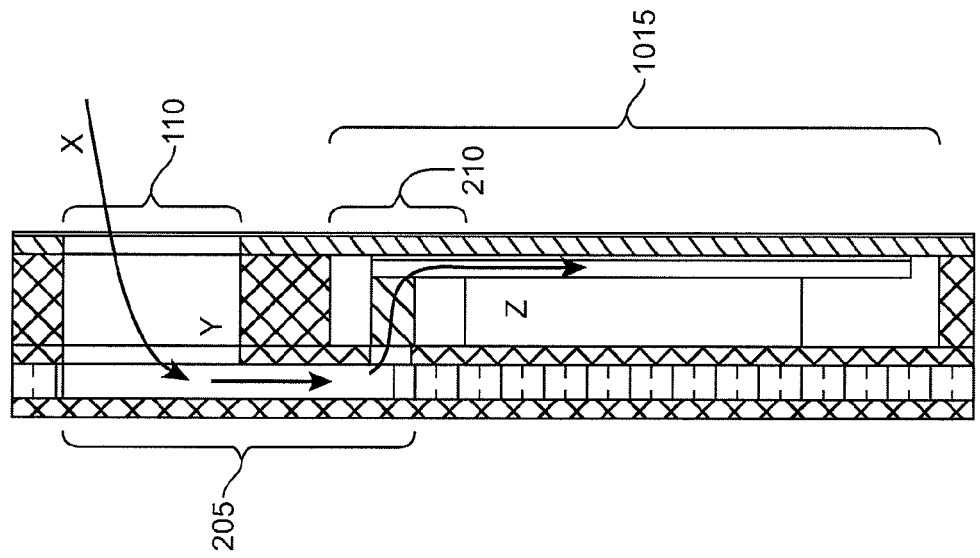
Figure 10:
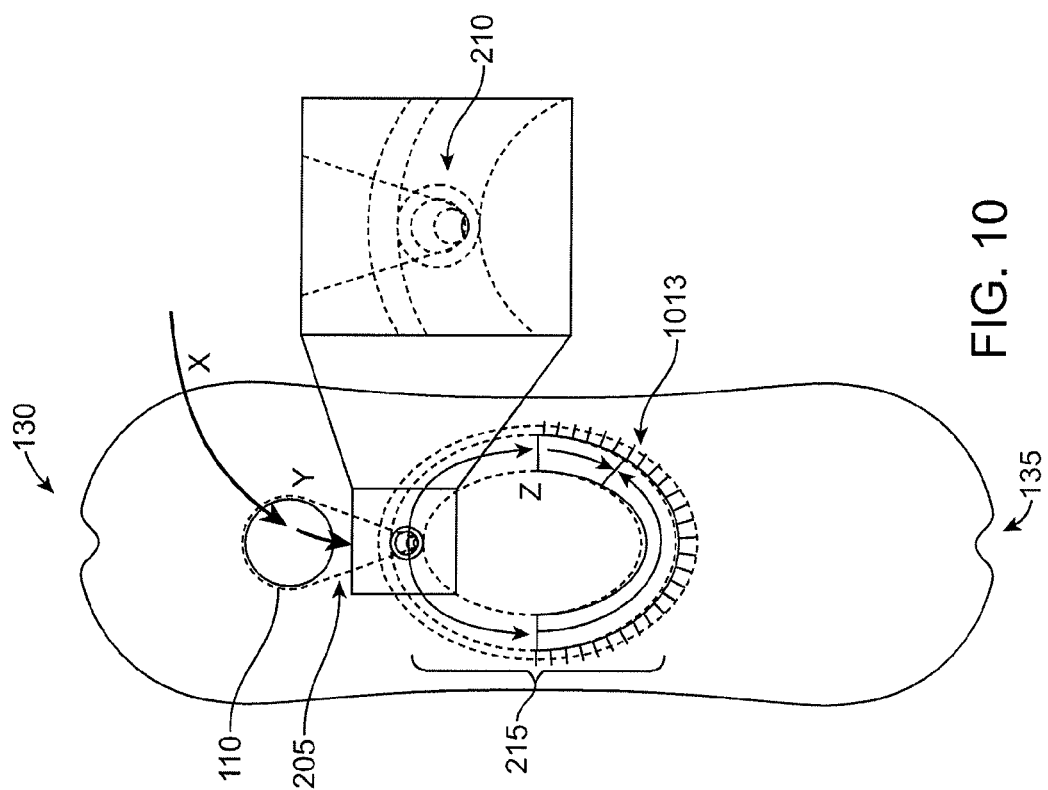

FIG. 10 shows a top view of the device 905 with a top cover removed. FIG. 11 shows a side, cross-sectional view of the device 905. The well 110 (which is configured to receive blood) forms an opening in the top of the device and extends downwardly toward the bottom of the device. As shown in FIG. 11, the bottom end of the well 110 communicates with a capillary reservoir 205 that extends from the well 110 toward the distal end 135 of the device.

The capillary reservoir 205 communicates with a vertical conduit 210 that provides a pathway for fluid to flow from the capillary reservoir 205 toward an elongated indicator dial 1015 that is positioned at least partially above the capillary reservoir. The indicator dial 1015 may be glass fiber filter paper. The indicator dial 1015 has an oval, circular, elliptical, "racetrack." etc. shape that conforms or complements the shape of the scale 925 and indicator window 920.

In an embodiment, the indicator dial 1015 is made from a thin glass-fiber lateral blood separation material. The indicator dial 1015 extends in an arced or rounded fashion distally along the length of the device and terminates at a location 1020 where fluid flowing along the indicator dial converges at location 1013. At the location 1020, saturation of the paper is reached and no further fluid migration can occur. The depth and relative sizes of various components may be exaggerated for clarity of illustration.

Figure 12:
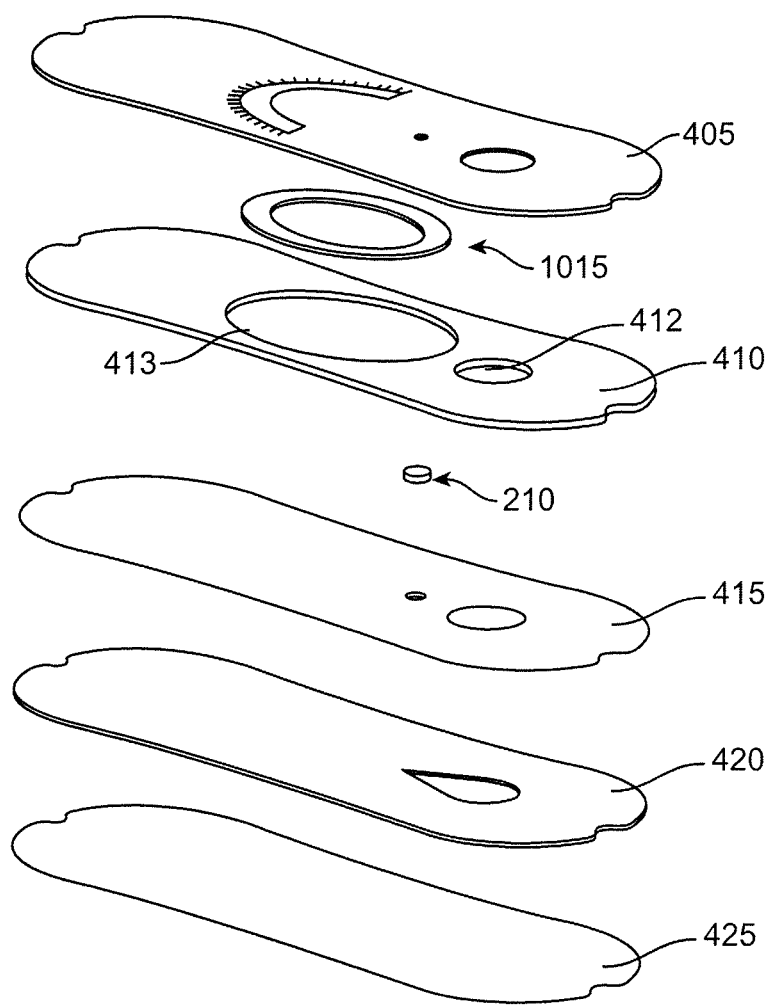

The device 905 may be formed of various components that are assembled to collectively form the device. FIG. 12 shows an exploded view of an exemplary set of layered components that form the device 105. It should be appreciated that the configuration of the components can vary and is not limited to what is shown in FIG. 12. A top cover 405 forms a top layer of the device. The indicator dial 1015 is positioned immediately below and adjacent the top cover 405 such that the indicator dial 1015 is adhered to the underside of the top cover 405. A middle layer 410 is positioned below the top cover 405 and includes a cut-out 412 that comprises an indicator housing around the separator components of the device. The middle layer 410 also includes a cut-out 413 for the indicator dial 1015. The vertical conduit 210 is sized and shaped to be positioned at least partially within the cut-out 412. The vertical conduit 210 is adhered to the top of a layer 415 such that it extends upwardly through the cut-out 412 and communicates with the indicator dial 1015. An additional middle layer 420 is positioned below the layer 415 and above a bottom layer 425, which forms a base of the device. The layers may include various additional cut-outs that align with one another to form reservoirs and/or passageways of the device 105, such as, for example, the capillary reservoir 205, the well 110, and the excess volume reservoir 220.

Figure 13:
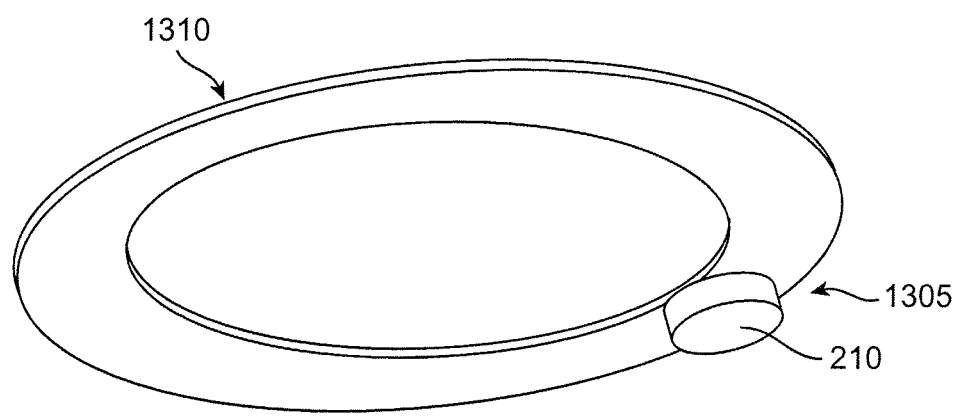

FIG. 13 depicts the components that together provide a path for sample fluid migration and form the indicator dial 1015. The indicator dial 1015 has a rounded shape and is coupled to the vertical conduit 210. Some pretreatment of the sample may occur in the vertical conduit. Sample fluid migrates up from the underside of vertical conduit 210 toward and onto a proximal end of the indicator dial 1015. The sample fluid flows around both sides of the indicator dial 1015 from the proximal end 1305. One side of the indicator dial 1015 can be treated with agents that modify flow rate in response to the concentration of analyte. The top of the device 905 has graduations (represented by scale 925, FIG. 9A) that determine the position along the circumference of the indicator dial 1015 that the fluid fronts converged, thus indicating analyte concentration or other fluid variable in the sample.

Figure 15:
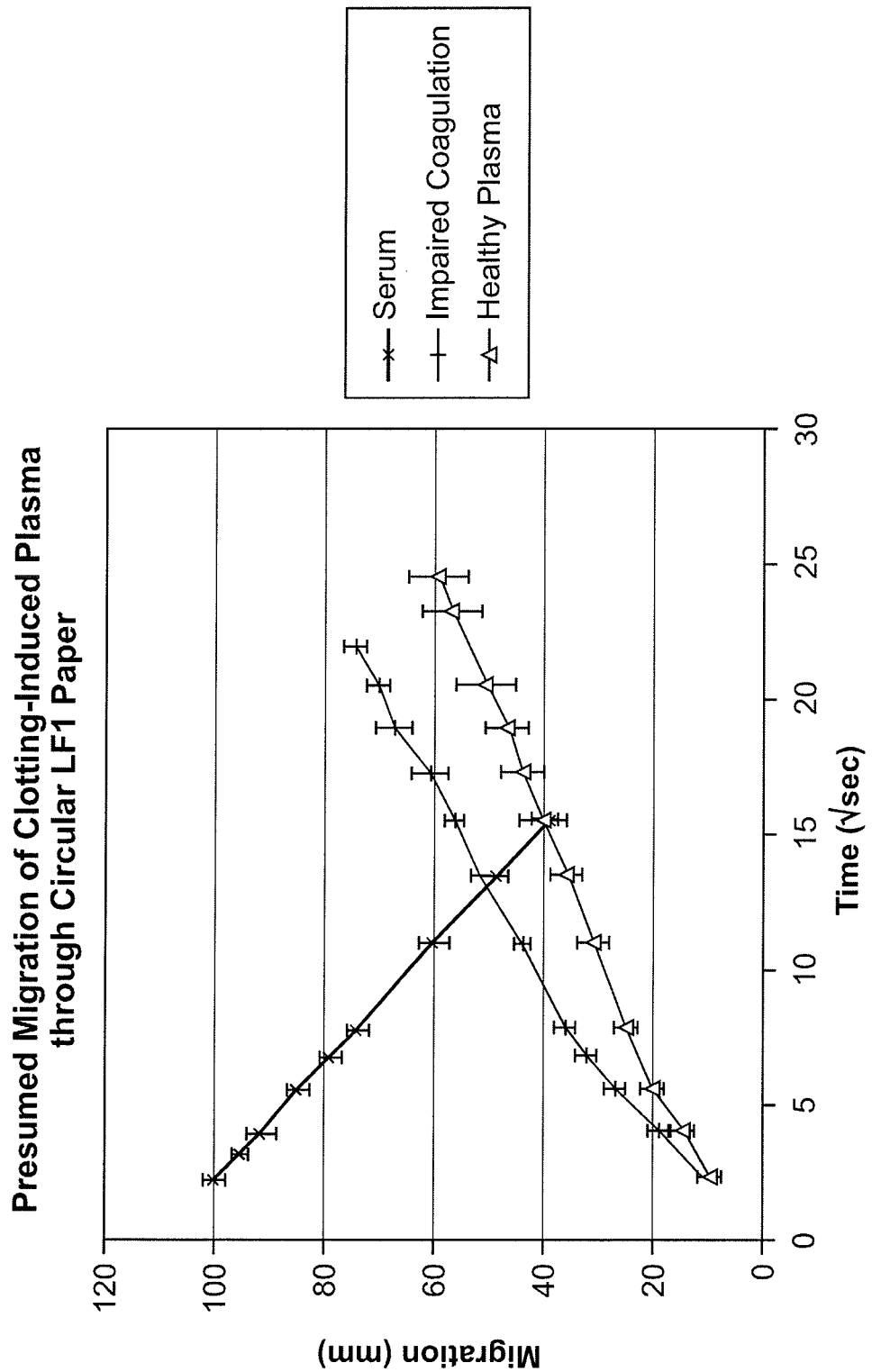

FIGS. 1A, 1B, 2, and 3 show a representation of data collected for vertical flow of water through a 0.25" wide strip of Fusion-5 separation paper (Whatman). The strip was contained in a plastic housing. At time zero, the bottom 1 mm of the strip was submerged in water containing a blue dye. At periodic intervals, the position of the liquid front was marked on the housing, and later measured with calipers. The velocity of the front (in cm/s) was determined by the central difference technique on the position data. The velocity versus 1/x was plotted as shown in FIG. 15 (the first four time points were left out, as they are subject to variability). A line was fit to this data, and kd and kr (Equation 7b) were derived from the slope and the intercept. These values were then used to integrate Equation 7a, using a 4th-order Runge-Kutta method. The values from this model were then plotted in FIG. 15 as a solid line.

E. A Method and Device for Measuring Coagulation

Measurement of coagulation time is one example of using viscosity to monitor the state of a sample. Provided herein are devices that can be used to measure coagulation in an individual or sample. Coagulation is defined as the process by which blood forms clots. It is an important part of hemostasis (the cessation of blood loss from a damaged vessel), wherein a damaged blood vessel wall is covered by a platelet and fibrin-containing clot to stop bleeding and begin repair of the damaged vessel. Disorders of coagulation can lead to an increased risk of bleeding (hemorrhage; not enough coagulation) or clotting (thrombosis; too much coagulation). The devices provided herein can thus be used to detect and/or monitor coagulation abnormalities by measuring the degree of coagulation activity in a sample.

1. Coagulation Process and Factors

The coagulation process involves a series of dependent signaling events that ultimately lead to the formation of a blot clot. Effective coagulation of blood is needed to prevent excessive blood loss at the site of injury. A rupture or injury to the blood vessel exposes highly thrombogenic subendothelial connective tissue that is composed of fibrillar collagen, which binds and activates platelets and stimulates platelet aggregation at the injury site. The activated platelets secrete factors which stimulate additional platelet activation, and other molecules, such as serotonin, phospholipids, and lipoproteins, which are important mediators of the clotting process. Fibrinogen, a component of the blood plasma also binds platelets and aids in clumping of the activated platelets. The activated platelets in turn undergo changes in cell shape to form a loose platelet plug. A clotting cascade of peptidases is simultaneously initiated that generates activated molecules such as thrombin (from cleavage of prothrombin), which further activates platelets, and fibrin (from cleavage of fibrinogen), which forms a cross-linked polymer around the platelet plug to stabilize the clot. During clot formation, coagulation factor inhibitors also circulate through the blood to prevent clot formation beyond the injury site. The specific processes of coagulation and the factors involved are presented in further detail below.

Under normal conditions, vascular endothelium is resistant to clot formation. This resistance is supported by mechanisms that enhance vasodilation, inhibit platelet adhesion and activation, suppress coagulation, and promote fibrin cleavage. Vascular endothelial cells secrete molecules such as nitrous oxide (NO) and prostacylin, which inhibit platelet aggregation and dilate blood vessels. Release of these molecules activates soluble guanylate cyclases (sGC) and cGMP-dependent protein kinase I (cGKI) and increases cyclic guanosine monophosphate (cgMP) levels, which cause relaxation of the smooth muscle in the vessel wall. Furthermore, endothelial cells express cell-surface ADPases, such as CD39, which control platelet activation and aggregation by converting ADP released from platelets into adenine nucleotide platelet inhibitors. Other membrane proteins expressed on the surface of vascular endothelial cells include heparin sulfate proteoglycans that function as cofactors for antithrombin III, which inhibits thrombin and other coagulation factors. In addition, vascular endothelial cells secrete plasminogen to promote fibrinolysis, which lyses and clears clots.

Upon blood vessel injury, the damaged vessel wall exposes the subendothelial connective tissue to the circulating blood. In contrast to normal endothelial cells, this tissue is extremely thrombogenic. The layer is composed of proteins such as von Willebrand factor (vWF) and fibrillar collagen, which bind to circulating platelets via glycoprotein receptors expressed on the surface of the platelets. The platelet glycoprotein receptor complex GPIb-V-IX binds vWF, whereby vWF can bridge the platelets to the collagen fibrils. vWF is a multimeric glycoprotein, which contributes to its ability to aggregate platelets. vWF also functions to stabilize coagulation factors, such as factor VIII, and promotes their survival in the blood stream. Furthermore, the platelet integrin receptors $\alpha_2\beta_1$ and GPVI can bind to collagen directly. Binding of collagen to $\alpha_2\beta_1$ can facilitate binding to the lower affinity GPVI receptor. The collagen interactions with $\alpha_2\beta_1$ and GPVI contribute to platelet adherence to the site of injury and furthermore promote platelet activation through activation of intracellular signaling cascades.

During clot formation, positive feedback loops are activated that enhance the maturation of a clot. Following platelet activation, expression of the platelet surface integrin $\alpha_{IIb}\beta_3$ is stimulated. $\alpha_{IIb}\beta_3$ can bind to vWF and fibrinogen. Binding of GPIb-V-IX to vWF can enhance the affinity of $\alpha_{IIb}\beta_3$ for vWF to promote platelet adhesion. Further, one fibrinogen molecule can bind to multiple $\alpha_{IIb}\beta_3$ integrin molecules from different cells, thus, enhancing platelet aggregation.

Platelet activation stimulates the release of platelet alpha and dense granules. The released contents of the granules include factors, such as vWF and ADP, which further contribute to aggregation and platelet activation. ADP helps stimulate modification of the platelet membrane that allows binding of fibrinogen to $\alpha_{IIb}\beta_3$, and vWF contributes to adhesion and aggregation as discussed above.

In addition to ADP, activated platelets also secrete factors such as serotonin and thromboxane $A_2$ ($TXA_2$) which also positively regulate platelet activation. Signal transduction cascades activated in response to thrombin binding control release of these factors. During platelet activation, thrombin binds to a G-protein coupled receptor on the surface of platelets. The receptor becomes stimulated, and the activated G-protein activates phospholipase C-γ 2 (PLCγ2), which hydrolyzes phosphatidylinositol 4,5-bisphosphate ($PIP_2$) to generate inositol triphosphate ($IP_3$) and diacylglycerol (DAG). $IP_3$ stimulates release of intracellular calcium ($Ca^{2+}$) stores from the endoplasmic reticulum by binding to $IP_3$ receptors. The released calcium in combination with collagen binding to platelets leads to the activation of phospholipase A2 ($PLA_2$). $PLA_2$ then hydrolyzes membrane phospholipids, such as phosphatidylcholine (PC) and phosphatidylethanolamine (PE), to generate arachidonic acid, which in turn stimulates the production and release of $TXA_2$.

The production of DAG by activated platelets stimulates protein kinase C, which then phosphorylates a platelet specific 47 kDa protein (p47). The phosphorylated p47 protein induces the release of the platelet granules as discussed above. Intracellular $Ca^{2+}$ release also activates myosin-light chain kinase (MLCK) that phosphorylates the light chain of myosin. The phosphorylated myosin then interacts with actin, bringing about a change in platelet morphology and motility, necessary for clot formation.

Platelet activation through collagen binding also elicits activation of a similar signaling cascade. When collagen binds to the GPVI integrin, it promotes clustering of GPVI with the Fc receptor γ-chain (FcγR). The clustering induces tyrosine phosphorylation of the FcγR by Src-family kinases Lyn and Fyn, which promote binding and activation of the tyrosine kinase Syk. Syk, in turn phosphorylates the transmembrane adapter protein LAT, which then assembles a signaling complex composed of proteins including phosphoinositide 3-kinase (PI3K), PLCγ2, adaptor proteins such as Gads, SLP-75, and SLAP-130, and the RhoGTP exchange factor Vav. PI3K can then regulate protein kinase B (PKB), phosphoinositide-dependent kinase (PDK1) and integrin-linked kinase (ILK), which can regulate integrin expression and signaling. PLCγ2 generates $IP_3$ and DAG to mobilize calcium and activate PKC as described above.

For stable clot formation, cross-linked fibrin polymers must be formed surrounding the activated platelet plug. Fibrin formation is generated though activation of coagulation factor cascades, which occurs simultaneously with platelet activation following vessel injury. Two converging pathways can be activated, the intrinsic and extrinsic pathway. Key factors that participate in the intrinsic and extrinsic coagulation cascades are listed in Tables 1 and 2. The high-molecular weight kininogen, prekallikrein, and factors XII, XI, IX, and VIII participate in the intrinsic pathway, while tissue factor and the factor VII complex contribute to the extrinsic pathway. The two pathways converge at the activation of factor X (to generate FXa), through proteolytic action of the activated factor IX (FIXa)/factor VIII (FVIIIa) tenase complex (intrinsic) or by the activated factor VII (FVIIa)/tissue factor (TF) complex (extrinsic). Activated factor X (FXa), with the help of factor V, calcium, and platelet phospholipid, generates thrombin from prothrombin. In turn, thrombin cleaves fibrinogen to produce fibrin and also activates factor XIII (transglutamidase), which cross-links fibrin polymers to form the stable clot. The surface of activated platelets facilitates the formation of the activated coagulation factor complexes and thus participates in amplification of the cascade.

The primary pathway for initiation is the extrinsic pathway; the intrinsic pathway functions to amplify the production of activated factor X. Following vascular injury, tissue factor (TF) in the vessel wall is exposed and generated. TF is expressed by endothelial cells, subendothelial tissue, and monocytes. When the vessel wall is disrupted TF produced by the subendothelial layer is exposed. In the case of endothelial cell damage in the absence of a vessel wall lesion, contact is made between the blood and TF expressed on the damaged endothelial layer in the cell wall. vWF aids in the interaction of platelets with the damaged endothelium. TF binds to VII and in turn catalyzes the activation of factor X. The thrombin that is generated by the extrinsic pathway then contributes to activation of factor XI of the intrinsic cascade, leading to the activation of factor IX. Factor IX also can be activated directly by the TF/factor VII complex. The intrinsic cascade also can be activated via factor XII-mediated activation of factor XI when prekallikrein is converted to kallikrein in response to collagen contact with the vessel surface (called the contact pathway).

TABLE 1

Clotting Factors

| Factor | Common Name(s) | Pathway | Characteristic |
|---|---|---|---|
| Prekallikrein (PK) | Fletcher factor | Intrinsic | Functions with HMWK and factor XII |
| High molecular weight kininogen (HMWK) | contact activation cofactor; Fitzgerald, Flaujeac Williams factor | Intrinsic | Co-factor in kallikrein and factor XII activation, necessary in factor XIIa activation of XI, precursor for bradykinin (a potent vasodilator and inducer of smooth muscle contraction |
| I | Fibrinogen | Both | |
| II | Prothrombin | Both | Contains N-term. gla segment |
| III | Tissue Factor | Extrinsic | |
| IV | Calcium | Both | |
| V | Proaccelerin, labile factor, accelerator (Ac-) globulin | Both | Protein cofactor |
| VI | Accelerin | Both | This is Va, redundant to Factor V |
| VII | Proconvertin, serum prothrombin conversion accelerator (SPCA), cothromboplastin | Extrinsic | Endopeptidase with gla residues |
| VIII | Antihemophiliac factor A, antihemophilic globulin (AHG) | Intrinsic | Protein cofactor |
| IX | Christmas Factor, antihemophilic factor B, plasma thromboplastin component (PTC) | Intrinsic | Endopeptidase with gla residues |
| X | Stuart-Prower Factor | Both | Endopeptidase with gla residues |
| XI | Plasma thromboplastin antecedent (PTA) | Intrinsic | Endopeptidase |
| XII | Hageman Factor | Intrinsic | Endopeptidase |
| XIII | Protransglutaminase, fibrin stabilizing factor (FSF), fibrinoligase | Both | Transpeptidase |

Table adapted from King (2010) http://themedicalbiochemistrypage.org/blood-coagulation.html#clinical

TABLE 2

Functional Classification of Clotting Factors

| Factors | Activities |
|---|---|
| *Zymogens of Serine Proteases* | |
| Factor XII | binds to exposed collagen at site of vessel wall injury, activated by high-MW kininogen and kallikrein |
| Factor XI | activated by factor XIIa |
| Factor IX | activated by factor XIa in presence of $Ca^{2+}$ |
| Factor VII | activated by thrombin in presence of $Ca^{2+}$ |
| Factor X | activated on surface of activated platelets by tenase complex and by factor VIIa in presence of tissue factor and $Ca^{2+}$ |
| Factor II | activated on surface of activated platelets by prothrombinase complex |
| *Cofactors* | |
| Factor VIII | activated by thrombin; factor VIIIa is a cofactor in the activation of factor X by factor IXa |
| Factor V | activated by thrombin; factor Va is a cofactor in the activation of prothrombin by factor Xa |
| Factor III (tissue factor) | a subendothelial cell-surface glycoprotein that acts as a cofactor for factor VII |
| *Fibrinogen* | |
| Factor I | cleaved by thrombin to form fibrin clot |
| *Transglutaminase* | |
| Factor XIII | activated by thrombin in presence of $Ca^{2+}$; stabilizes fibrin clot by covalent cross-linking |
| *Regulatory/Other Proteins* | |
| von Willebrand factor | associated with subendothelial connective tissue; serves as a bridge between platelet glycoprotein GPIb/IX and collagen |
| Protein C | activated to protein Ca by thrombin bound to thrombomodulin; then degrades factors VIIIa and Va |
| Protein S | acts as a cofactor of protein C; both proteins contain gla residues |
| Thrombomodulin | protein on the surface of endothelial cells; binds thrombin, which then activates protein C |
| Antithrombin III | most important coagulation inhibitor, controls activities of thrombin, and factors IXa, Xa, XIa and XIIa |

Table adapted from King (2010) http://themedicalbiochemistrypage.org/blood-coagulation.html#clinical 2. Coagulation Disorders The devices provided herein can be used to monitor coagulation activity in subjects who suffer from coagulation disorders. Conditions resulting from thrombosis (undesired blood clot formation) are the leading cause of death and morbidity in the developed world. Such conditions include stroke, heart attack, deep vein thrombosis, and pulmonary embolism, among others. Conversely, disorders such as hemophilia and von Willebrand Disease are characterized by coagulation deficiencies, resulting in excessive bleeding. These and other coagulation disorders are described in detail below.

a. Hemophilia

Hemophilia is a bleeding disorder that is caused by a deficiency in one or more blood coagulation factors. It is characterized by a decreased ability to form blood clots at sites of tissue damage. Congenital X-linked hemophilias include hemophilia A and hemophilia B, or Christmas disease, which are caused by deficiencies in FVIII and FIX, respectively. Hemophilia A occurs at a rate of 1 out of 10,000 males, while hemophilia B occurs in 1 out of 50,000 males.

Patients with hemophilia suffer from recurring joint and muscle bleeds, which can be spontaneous or in response to trauma. The bleeding can cause severe acute pain, restrict movement, and lead to secondary complications including synovial hypertrophy. Furthermore, the recurring bleeding in the joints can cause chronic synovitis, which can cause joint damage, destroying synovium, cartilage, and bone.

b. Thrombotic Diseases and Conditions

Thrombotic diseases are characterized by hypercoagulation, or the deregulation of hemostasis in favor of development of blot clots. Exemplary thrombotic diseases and conditions include arterial thrombosis, venous thrombosis, venous thromboembolism, pulmonary embolism, deep vein thrombosis, stroke, ischemic stroke, myocardial infarction (heart attack), unstable angina, atrial fibrillation, renal damage, percutaneous translumenal coronary angioplasty, disseminated intravascular coagulation, sepsis, artificial organs, shunts or prostheses, and other acquired thrombotic diseases.

c. von Willebrand Disease von Willebrand Disease (vWD) is due to inherited deficiency in von Willebrand factor (vWF). vWD is the most common inherited bleeding disorder of humans. Deficiency of vWF results in defective platelet adhesion and causes a secondary deficiency in factor VIII. The result is that vWF deficiency can cause bleeding that appears similar to that caused by platelet dysfunction or hemophilia. vWD has been classified into several major subtypes. Type I vWD is the most common and is inherited as an autosomal dominant trait. This variant is due to simple quantitative deficiency of all vWF multimers. Type 2 vWD is also subdivided further dependent upon whether the dysfunctional protein has decreased or paradoxically increased function in certain laboratory tests of binding to platelets. Type 3 vWD is clinically severe and is characterized by recessive inheritance and virtual absence of vWF.

d. Acquired Coagulation Disorders

Acquired coagulation disorders are the result of conditions or diseases, such as vitamin K deficiency, liver disease, disseminated intravascular coagulation (DIC), or development of circulation anticoagulants. The defects in blood coagulation are the result of secondary deficiencies in clotting factors caused by the condition or disease. For example, production of coagulation factors from the liver is often impaired when the liver is in a diseased state. Along with decreased synthesis of coagulation factors, fibrinolysis becomes increased and thrombocytopenia (deficiency in platelets) is increased. Decreased production of coagulation factors by the liver also can result from fulminant hepatitis or acute fatty liver of pregnancy. Such conditions promote intravascular clotting which consumes available coagulation factors.

3. Pharmacological Coagulation Treatments

The devices provided herein can be used to monitor coagulation activity in patients undergoing treatment with coagulation-modifying agents. Such coagulation agents include, but are not limited to, the anticoagulants and procoagulants described below.

Coumarin drugs (based on the chemical benzopyrone), such as warfarin (COUMADIN®) as well as the glycosaminoglycans, heparin and heparan sulfate, are employed clinically as anticoagulants. Heparin acts as an anticoagulant because it binds to, and activates, antithrombin III which then inhibits the serine proteases of the coagulation cascade. Heparin is abundant in granules of the mast cells that line the vasculature. In response to injury, heparin is released and inhibits coagulation. The coumarin drugs inhibit coagulation by inhibiting the vitamin K-dependent γ-carboxylation reactions necessary to the function of thrombin, and factors VII, IX, and X as well as proteins C and S. These drugs act by inhibiting the reduction of the quinone derivatives of vitamin K to their active hydroquinone forms. Because of the mode of action of coumarin drugs, it takes several days for their maximum effect to be realized. For this reason, heparin is normally administered first followed by warfarin or warfarin-related drugs.

The plasminogen activators also are useful for controlling coagulation. Because tPA is highly selective for the degradation of fibrin in clots, it can restore the patency of the coronary arteries following thrombosis, in particular during the short period following myocardial infarct. Streptokinase (an enzyme from the *Streptococci* bacterium) is another plasminogen activator with therapeutic uses.

Aspirin is an inhibitor of platelet activation. By virtue of inhibiting the activity of cyclooxygenase, aspirin reduces the production of $TXA_2$ by platelets. Aspirin also reduces endothelial cell production of prostacyclin ($PGI_2$), an inhibitor of platelet aggregation and a vasodilator.

Other classes of anticoagulation drugs function by inhibiting the activation of platelets and their subsequent aggregation. The drug clopidogrel (PLAVIX®) is an irreversible inhibitor of the ADP receptor on platelet membranes. When ADP binds to platelets they are activated and aggregate leading to amplification of the coagulation response, thus PLAVIX® interferes with this process. PLAVIX® is prescribed for the treatment of peripheral vascular and cerebrovascular disease as well as coronary artery disease to prevent the formation of thrombotic plaques.

Another family of anticoagulants is the GPIIb-GPIIIa antagonists which inhibit platelet aggregation. This family of drugs includes REOPRO® (abciximab; a human monoclonal antibody), INTEGRILIN® (eptifibatide; a cyclic hexapeptide derived from a protein found in the venom of the southeastern pygmy rattlesnake) and AGGRASTAT® (tirofiban; a synthetic organic non-peptide molecule).

While the anticoagulant drugs have been a major tool in the treatment or prevention of coagulation disorders described herein, overly stringent anticoagulant regimens can dramatically increase the risk of death by hemorrhage (in fact, overly aggressive use of anticoagulants is strongly linked to increased risk of death regardless of cause), making it vital to monitor such patients for coagulation ability. Anticoagulants are normally given on a daily basis, and at least in early stages of therapy, testing for coagulation activity also follows a daily routine.

In some diseases or conditions, procoagulants are indicated. Coagulation factor concentrates, for example, are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly used coagulation factor products. Recombinant activated human factor VII also is used in the treatment of major bleeding. Other procoagulants include Tranexamic acid and aminocaproic acid which inhibit fibrinolysis, and thus lead to reduced bleeding. Since procoagulant therapy can increase the risk of unwanted thrombosis, close monitoring of coagulation activity in these patients is critical.

4. Coagulation Measurement

The devices provided herein can be used to measure coagulation activity. The lateral flow devices provided herein measure the coagulation ability of a blood sample by detecting changes in the rate of the capillary flow of the sample fluid through porous media such as filter paper. In one embodiment, sample fluid to be tested flows by capillarity down two or more converging arms of a common element of porous media, in which at least one of the arms has been modified by the addition of agents which promote the coagulation cascade, thus decreasing flow rate. The fluid fronts will converge at a position determined by their relative flow rates, which is thus indicative of the coagulation ability of the sample fluid. In another embodiment, sample fluid to be tested flows by capillarity in parallel down two or more individual arms of a common element of porous media, in which at least one of the arms has been modified by the addition of agents which promote the coagulation cascade, thus decreasing flow rate. The fluid fronts will arrest at points determined by their relative flow rates; a comparison of these points is thus indicative of the coagulation ability of the sample fluid. In another embodiment, sample fluid to be tested flows by capillarity down a linear element of porous media, which has been modified by the addition of agents which promote the coagulation cascade, thus decreasing flow rate to zero. The fluid front will arrest at a point determined by the stopped flow of the sample, which is thus indicative of the coagulation ability of the sample fluid. Specific uses for the devices provided herein include, but are not limited to: (1) Basic monitoring of coagulation deficiencies. (2) Monitoring of patients taking anticoagulants, for example: activated partial thromboplastin time (APTT) is monitored in patients taking heparin and prothrombin time (PT) is monitored in patients taking Warfarin. (3) Thromboplastin generation tests (TGT) to differentiate between factor VIII clotting issues in people suffering from hemophilia A and factor IX clotting issues as in hemophilia B individuals. (4) Testing of specific factors to ascertain deficiencies within coagulation pathways.

Substantial efforts have been made to measure clotting components or evaluate blood coagulation activity. Most methodologies rely upon immunologic and clotting techniques. The basis of in vitro testing of blood coagulation has commonly been a determination of changes in turbidity, viscosity or electrical conductivity of a blood sample caused by the conversion of fibrinogen to fibrin during clot formation. Accordingly, a normal blood sample tends to produce a strong gel clot, whereas samples producing thin, watery, webby-type clots are indicative of some coagulation abnormality. Screening tests for coagulation disorders routinely include the prothrombin time (PT) and the activated partial thromboplastin time (APTT), described in detail below. Automated coagulation instrumentation, both mechanical and optical density-based, provide data about the end point of the clotting times in the various coagulation tests. The fibrometer-type of instrument measures increasing conductivity which may be correlated to the formation of clots. Essentially, the screening tests for coagulation disorders are designed to detect a significant abnormality in one or more of the clotting factors and to localize this abnormality to various steps in the coagulation pathway. The devices provided herein also can be used to measure coagulation activity and can be modified by the addition of agents to identify specific abnormalities in the coagulation pathway.

The degree of coagulation activity is usually measured by a prothrombin time (PT) test which determines the time required for blood clot formation. Prothrombin time (PT) measures the extrinsic pathway of coagulation. Induction of this pathway requires calcium. The process can be accelerated by the introduction of thromboplastin, a saline brain extract containing tissue factor, which initiates the extrinsic pathway. This pathway proceeds through a protein cascade by first activating Factor VII which in turn activates Factor X which in the presence of Factor V, converts pro-thrombin to thrombin which converts fibrinogen to fibrin. Fibrinogen is a soluble protein, but when cleaved into fibrin, coagulates into an insoluble gel. The consequence of production of fibrin polymers is increased viscosity of blood or plasma and impedance of flow, which in consequence, is therefore measurable by the devices provided herein. PT bypasses the intrinsic clotting pathway and is normal in patients with deficiencies of Factors XII, XI, IX and VIII. PT is abnormal in patients with deficiencies of Factors VII, X, V, pro-thrombin or fibrinogen.

PT times are usually either measured by automated instruments in the clinical laboratory, or by portable instruments in which finger-stick blood is placed on a disposable test strip. Because assays from different manufacturers using various reagents (or even different batches of identical reagents) can return different PT times, the World Health Organization adapted the standard of reporting the results as International Normalized Ratios (INR), which is the PT for a blood sample divided by the PT of a standardized normal sample, raised to the power of an International Sensitivity Index (ISI), a product- and batch-specific correction factor:

$$INR = \left(\frac{PT_{test}}{PT_{normal}}\right)^{ISI}$$

Where:
$PT_{test}$=Prothrombin Time (measured)
$PT_{normal}$=Normal Prothrombin Time (control)
ISI=International Sensitivity Index (an empirical constant provided by the manufacturer)

The normal range for PT is 12-15 seconds, the ISI factor is usually between 1.0 and 2.0, and the normal range for the INR is 0.9-1.3. Patients undergoing anticoagulation therapy will typically have INRs between 2.0 and 3.0; higher levels are considered overly risky. In order to reduce operator error, ISI values are often provided either through barcodes or a microchip so that the instruments can automatically perform the correct conversion to INR. Unfortunately, recent studies have shown that the INR standard fails to harmonize even the results of different laboratory assays for PT measurement, a problem that has been known since the early 1990s.

As noted above, the PT test typically reflects the integrity of the extrinsic coagulation pathway. Deficiencies in the extrinsic pathway can be identified using any of the devices provided herein. Extrinsic factor activators such as, thromboplastin, for example, can be added to one or more components of any of the devices provided herein, with or without calcium. In one embodiment, the device is a linear flow device and the extrinsic factor activator is added to the vertical conduit. In another embodiment, the device is a split-flow device and the extrinsic factor activator is added to one arm of the lateral flow strip. In another embodiment, the device is a convergent flow device and the extrinsic factor activator is added to one side of the circular porous medium or proximal pad.

APTT measures coagulation factors of the intrinsic pathway, including Factors XII, XI, IX, VIII, X, V, II and I which may be abnormal due to heritable disorders or heparin therapy. APTT is therefore useful as a presurgical screen and for monitoring heparin therapy. The APTT is typically performed by adding an activator such as kaolin (insoluble silicate), ellagic acid, silica, or negatively-charged phospholipids, for example, to a plasma sample. This activates Factors XII and XI. Phospholipid substitutes for platelet in the activation of Factor VIII by Factors IX, VIII and V. Blood coagulation is initiated in this clotting test by adding calcium. Factor VII is the only factor not affected by the partial thromboplastin time and the APTT is, therefore, normal in patients with a Factor VII deficiency. Deficiencies in the intrinsic pathway can be identified using any of the devices provided herein. Intrinsic factor activators such as kaolin (insoluble silicate), ellagic acid, silica, or negatively-charged phospholipids, for example, can be added to one or more components of any of the devices provided herein, with or without calcium. In one embodiment, the device is a linear flow device and the intrinsic factor activator is added to the vertical conduit. In another embodiment, the device is a split-flow device and the intrinsic factor activator is added to one arm of the lateral flow strip. In another embodiment, the device is a convergent flow device and the intrinsic factor activator is added to one side of the circular porous medium or proximal pad.

Another test used to identify specific defects in coagulation is the Thromboplastin Generation Test (TGT) (W. H. Bell and H. G. Alton, Nature 174:880-881, 1954). In this type of test, a patient's serum, plasma, or platelets are substituted in a system that is complete except for one of the factors to be tested for (antihemophilic factor, plasma thromboplastin antecedent, plasma thromboplastin component, or platelets), and the rate of thromboplastin generation is determined. Thromboplastin generation tests (TGT) can be used, for example, to differentiate between factor VIII clotting issues in people suffering from hemophilia A and factor IX clotting issues as in hemophilia B individuals. The devices provided herein can be modified to perform TGT tests by the addition of various clotting factors indicative of the specific deficiency for which the test is performed and determined by one of skill in the art.

In some embodiments, a device described herein is used to measure a blood sample that has been treated with a calcium chelator to prevent clotting. Calcium is a required cofactor in the coagulation cascade, so blood treated with a calcium chelator, such as, for example citrate, does not clot. The coagulation cascade can be reactivated by introducing a molar excess of calcium relative to citrate. Other calcium chelators, such as EDTA, for example, produce similar effects. In some embodiments, the test is performed using whole blood. In other embodiments, the initial vertical separation component, or vertical conduit, of the device separates plasma from blood. The vertical conduit can be a material, such as a glass fiber filter (e.g., Millipore AP25), capable of separating cells from fluid (i.e., plasma or serum) in a vertical orientation, if such separation is desired. In a convergent flow device embodiment, the separated plasma reaches the indicator dial and migrates in both directions, initially at equal rates. In a particular embodiment, the indicator dial is made of thin glass fiber material. Specifically, MF1 glass fiber (Whatman, N.J., U.S.A.) is used. One direction of the dial is treated with calcium to allow the coagulation cascade to initiate. This side of the dial also can be treated with thromboplastin, for example, or any other material that can accelerate coagulation. The other side of the dial remains untreated so that migration of plasma in this direction is not retarded due to coagulation. The untreated side can optionally contain bromophenol blue to help visualize progression of the fluid front and/or identify the point of convergence. The plasma migrating in each direction on the dial eventually meets somewhere on the opposing side of the dial. The point where the plasma meets directly indicates the capability of the blood sample to coagulate. For example, a blood sample that is completely deficient in coagulation will meet 180° from where the plasma entered the quantitative dial since blood migrating in each direction will have traveled at the same rate (the actual location where uncoagulated blood meets can be modified to allow the dial to read different ranges of INR). With blood samples that have increasingly healthy coagulation function, the point of convergence of the plasma on the dial increasingly favors the side of the dial where coagulation (and therefore retardation of plasma migration) occurs.

In a split flow device embodiment, the separated plasma reaches a starting point on the linear porous strip, such as, for example, the midpoint of the lateral strip and initially migrates both directions at equal rates. One direction of the strip is treated with calcium to allow the coagulation cascade to initiate. This side of the strip also can be treated with thromboplastin, for example, or any other material that can accelerate coagulation. The other side of the strip remains untreated so that migration of plasma in this direction is not retarded due to coagulation. The plasma fronts migrating in each direction on the strip eventually arrest somewhere on each side of the strip. The relative points where the plasma front arrests directly indicates the capability of the blood sample to coagulate. For example, a blood sample that is completely deficient in coagulation will have identical arrested fronts relative to the starting point since blood migrating in each direction will have traveled at the same rate. With blood samples that have increasingly healthy coagulation function, the migration distance of the plasma front on the treated side of the strip decreases relative to the migration distance of the sample on the untreated side.

In a stopped flow device embodiment, the separated plasma reaches a starting point on the linear porous strip, such as, for example, the proximal end lateral strip and migrates towards the distal end. One or more regions of the strip can be treated with calcium to allow the coagulation cascade to initiate. One or more regions of the strip also can be treated with thromboplastin, for example, or any other material that can accelerate coagulation. In some embodiments of the device, bromophenol blue can be applied onto the center of the distal pad (or distal end) of the indicator strip in order to provides a visual indicator that fluid migrated to the distal pad of the indicator strip, indicating saturation of the strip. The migrating plasma front eventually arrests somewhere on the strip. The point where the plasma front arrests directly indicates the capability of the blood sample to coagulate. For example, a blood sample that is completely deficient in coagulation will have a longer migration distance than a sample with some coagulation activity. With blood samples that have increasingly healthy coagulation function, the migration distance of the plasma front on the strip decreases.

F. EXAMPLES

Example 1

Stopped-Flow Device Assembly

This example describes the assembly of an exemplary device that can be used for qualitative or semi-quantitative analysis of a component of a sample fluid based on the characteristics of fluid flow in a porous medium. The device is assembled using components and specifications as described herein. In an exemplary embodiment, an assembled device is rectangular in shape with proximal and distal ends. The dimensions of the device are 0.787 inch×by 5.3 inches. The outer housing of the exemplary device is a rigid material (specifically, acrylonitrile butadiene styrene (ABS), Snow White; Lustran 348-012002) that is solid on the bottom of the device and has an orifice on the top of the device for application of a fluid sample into a proximal well. Seven separate physical elements are adhered in a layered format to generate a device which can then be assembled into an outer housing made of ABS. The elements thus assembled create within the device a fluid pathway as follows: a proximal well for receiving a fluid sample which is in fluid communication with a volumetric capillary reservoir for transfer of the sample to the underside of a vertical conduit via a distal exit orifice, and a point of contact between the top of the vertical conduit and a proximal portion of a porous medium referred to as an indicator strip. In particular embodiments of the device, the porous medium is rectangular in shape.

A portion of the top of the exterior surface of the device is a transparent solid material for viewing the position of a fluid front as it migrates through the porous medium. For example, in a particular embodiment, the window is rectangular in shape positioned above a segment of the indicator strip. This transparent window in the housing facilitates visualization of the fluid front. Additional portions of the top of the exterior surface may also be a transparent solid material such as, for example, one or more windows positioned above a location(s) on the indicator strip that provide(s) a visual indication of successful migration of fluid into the porous medium. A detailed description of the components of the device and assembly thereof follows.

A. Proximal Bottom

The proximal bottom is a solid, thin, rigid material having an outer surface and an inner surface (see, e.g., FIG. 7). Specifically, Rigid Poly Vinyl Chloride is used to construct the proximal bottom at a thickness of 0.01 inch. All shapes can be produced using an Allen Datagraph template maker (Allen Datagraph Systems, Inc., Derry, N.H., U.S.A.). Parts can be designed in a computer-aided design (CAD) program, then "printed" by the template maker, which cut sheets of plastic into the desired shapes. The outer surface of the proximal bottom provides the outer-facing, solid base of the device, whereas the opposite, or inner, surface provides the inner-facing bottom of the device. The inner-facing bottom serves as a bottom of a volumetric capillary reservoir as well as provides a surface for the fluid sample to be applied. The fluid sample application area of the inner surface of the proximal bottom can be coated with substances (e.g., a mild 0.3% Tween-20® solution) to promote migration of fluid into the volumetric capillary reservoir. If the sample fluid is blood, the sample application area can be coated with a 20 µl solution of 70% ethanol containing 195 U/ml of Heparin sodium salt (to inhibit clotting of the blood sample).

B. Proximal Housing

The proximal housing is a thin, rigid material. Specifically, Rigid Poly Vinyl Chloride is used to construct the proximal housing at a thickness of 0.02 inch. The size and shape of the proximal housing are the same as those of the proximal bottom (see, e.g., FIG. 7). There is a hole in the proximal housing in the shape of a 0.576 inch long center to center tear drop with the 0.5 inch diameter wide end of the tear drop positioned proximally compared to the position of the 0.12 inch diameter narrow end of the tear drop. The proximal housing is adhered to the proximal bottom using 3M's 467 MP 2.3 mil. adhesive transfer tape (3M, St. Paul, Minn.). Once adhered to the proximal bottom, the edges of the hole in the proximal housing provide the walls of a volumetric capillary reservoir and set the volume for the reservoir at 0.002 cubic inches (33 µl). The wide, circular end of the tear drop shape of the reservoir also serves as the fluid delivery reservoir. The edges of the reservoir and the portion of the proximal cover that caps the volumetric capillary reservoir can together be coated with a substance (e.g., a mild 0.3% Tween-20® solution) to promote migration of fluid into the volumetric capillary reservoir.

C. Proximal Cover

The proximal cover is a thin, rigid material. Specifically, Rigid Poly Vinyl Chloride is used to construct the proximal cover at a thickness of 0.01 inch. The size and shape of the proximal cover are the same as those of the proximal housing (see, e.g., FIG. 7). There are two holes in the proximal cover. One hole is circular in shape measuring 0.5 inches in diameter and is positioned proximally with respect to the second hole, which is 0.125 inches in diameter. The proximal cover is adhered to the proximal housing 3M's 467 MP 2.3 mil. adhesive transfer tape such that the larger, proximal, circular hole is positioned over the wide, circular end of the tear drop shape of the reservoir formed by the proximal housing. Once adhered, the proximal cover caps the volumetric capillary reservoir, leaving a circular opening for the fluid sample delivery reservoir. The smaller, distal circular hole in the proximal cover provides the distal exit orifice of the volumetric capillary reservoir. The distal exit orifice is sized and located to promote capillary wicking of fluid into the vertical conduit. As mentioned above, the portion of the proximal cover that caps the volumetric capillary reservoir and edges of the reservoir can together be coated with a substance (e.g., a mild 0.3% Tween-20®) solution to promote migration of fluid into the volumetric capillary reservoir.

D. Vertical Conduit

The vertical conduit in one exemplary embodiment of the device is a polyethylene DBS filter. In embodiments in which the fluid to be analyzed is whole blood, the vertical conduit can be a material, such as a glass fiber filter (e.g., Millipore AP25), capable of separating cells from fluid (i.e., plasma or serum) in a vertical orientation, if such separation is desired. A particular polyethylene filter that can be used is Porex x4897 polyethylene dry blend surfactant (DBS) disk (3/16 inch diameter) with the following specifications can be used: 15-45 µm pore size; 1/16 inch thickness (Porex, Fairburn, Ga., U.S.A.). A semicircular or crescent shape is used to make the distance from any point on the distal edge of the vertical conduit and the proximal edge of the resolving region of the indicator strip consistent. This promotes the fluid front to converge at the resolving region of the indicator strip. The vertical conduit is adhered to the proximal cover using 3M's 467 MP 2.3 mil. adhesive transfer tape and situated directly above the distal exit orifice. The vertical conduit is positioned perpendicular to the plane of the housing. The distal orifice controls fluid flow such that fluid can enter the indicator housing only via capillary action of the indicator strip and, therefore, is unable to flow around and avoid being properly resolved within the indicator strip.

E. Indicator Housing

The indicator housing is a thin, rigid material. Specifically, Rigid Poly Vinyl Chloride is used to construct the indicator housing at a thickness of 0.04 inch. The size and shape of the indicator housing are the same as those of the proximal cover (see, e.g., FIG. 7). There are two holes in the indicator housing. One hole is circular in shape measuring 0.5 inches in diameter and is positioned proximally with respect to the second hole. The second hole is a cutout in the shape of the indicator strip. In a particular embodiment, the second hole is a rectangular cutout measuring 0.25 inches wide and 3.5 inches long. The indicator housing is adhered to the proximal cover using 3M's 467 MP 2.3 mil. adhesive transfer tape such that the circular proximal hole in the housing is positioned directly above the circular proximal hole in the proximal cover. In positioning the indicator housing in this way, the vertical conduit is located in, and perpendicular to the plane of, the proximal end of the rectangular cutout such that the fluid flow through the vertical conduit is perpendicular to the plane of the indicator housing. The indicator housing provides a minimal internal volume around the porous media components. This prevents humidity and other environmental variables from affecting fluid migration characteristics in the device.

F. Indicator Strip

The indicator strip is a lateral flow porous membrane made of three separate, but overlapping, materials. Specifically, from the proximal to the distal end of the indicator strip, the following three materials are used: Ahlstrom 8975 (a borosilicate glass fiber with a polyvinyl alcohol (PVA) binding with a thickness of 355-508 µm and water absorption of 19 µl/cm$^2$; Ahlstrom, Helsinki, Finland), blocked Pall Vivid 170 polyester-backed nitrocellulose (180 µm thick, 150-225 sec/4 cm capillary speed for water and 45-59 µg/cm2 protein (BSA) binding capacity; Pall Corporation, Port Washington, N.Y.), and Whatman LF1 (a 247 µm-thick, PVA-treated glass fiber paper that retains particles larger than 2 µm; Whatman, N.J., U.S.A.). The strip is rectangular in shape, following the shape of the second hole of the indicator housing. The width of the strip is 2 mm, and the overall length of the strip is 78 mm as follows, from proximal to distal ends (with a total of 4 mm overlap): Ahlstrom 8975 (20 mm length), Pall Vivid 170 (15 mm length) and Whatman LF1 (47 mm length). To construct the strip, strip components are assembled against a standard lateral flow backing (a PVC sheet with adhesive coating on one side). First, the Vivid 170 filter is blocked with 1 mg/ml neutravidin in PBS for 1 hour at room temperature, then washed twice for 5 minutes each time in PBS, rinsed twice with water and allowed to dry overnight on the benchtop. The filter is coated with neutravidin to focus the point where any aggregated particles of biotin-neutravidin traveling with the sample fluid through the indicator strip would arrest in the strip in order to produce a tighter blockage in the strip that lets less fluid through. Fluid samples without neutravidin analyte in solution do not show visibly arrested particles along the neutravidin-coated strip. The components are laid down with Vivid 170 being first pressed against the backing (with its own backing in contact with the device backing). The Ahlstrom 8975 and LF1 are then laid down with 2 mm of overlap over each end of the Vivid 170 strip. The Ahlstrom 8975 filter is allowed to overhang the adhesive backing by 5 millimeters.

Using 3M's 467 MP 2.3 mil. adhesive transfer tape, the indicator strip is adhered to the bottom surface of the distal top which, as described herein, also forms the top of the device with its outer, top surface. Thus, the strip is pressed to the underside of the roof of the device so that the strip is sandwiched between the roof of the device and the backing. The distal top, with the indicator strip and its backing adhered to its bottom surface, is adhered using 3M's 467 MP 2.3 mil. adhesive transfer tape to the indicator housing such that the indicator strip is positioned within the second hole (i.e., the rectangular cutout) of the indicator housing thereby creating a sealed internal volume housing the indicator strip. The indicator strip is thus contained in a space wherein the bottom, or floor, of the space provided by the proximal cover serves as a base for the strip, the rectangular hole in the indicator housing provides the walls of the space around the strip and the bottom surface of the distal top provides the roof of the space. The most proximal end of the overhang of the Ahlstrom 8975 filter of the indicator strip is situated above and in contact with the top of the vertical conduit which is adhered on the proximal cover. An optional distal pad can be included at the distal end of the indicator strip to provide a sink to collect excess sample fluid in the event that capillary flow of the fluid is not stopped in the indicator strip. If an analyte (e.g., neutravidin) is present in the sample fluid at sufficient concentration, a flow-modifying agent (e.g., LPA Biotin) that would be added to the sample prior to migration of the fluid through the medium, or early in the migration through the medium, binds with the analyte (e.g., neutravidin) to form a cross-linked network in which latex beads (which can also be added to the sample before, or early in, migration through the strip) become entrapped thereby blocking the pores of the strip and causing flow of the sample to stop. The amount of blockage of flow in the filters is directly proportional to the amount of analyte in the sample. Therefore, if the fluid front does not move past a specified position in the strip in a specified amount of time after sample fluid addition, this indicates that the concentration of the specific analyte in the sample fluid is above a threshold value.

In some embodiments of the device, 2 µl of a solution prepared by solubilizing dry bromophenol blue (BPB) into 95% ethanol at 10 mg/ml [weight-to-volume (w/v)] can be applied onto the center of the distal pad (or distal end) of the indicator strip and allowed to dry for 5 minutes. The blue color provides a visual indicator that fluid migrated to the distal pad of the indicator strip, indicating saturation of the strip.

G. Distal Top

The distal top is a thin rigid material. Specifically, Rigid Poly Vinyl Chloride is used to construct the distal top at a thickness of 0.01 inch. The size and shape of the distal top are the same as those of the indicator housing (see FIG. 7). The distal top contains a circular 0.02 inch diameter hole at the distal end of the indicator housing rectangular cutout which serves as an air escape opening allowing displaced air to escape as fluid is drawn into the device. One surface of the distal top forms the top of the device facing the exterior. Using 3M's 467 MP 2.3 mil. adhesive transfer tape, the indicator strip is adhered to the opposite (or bottom) surface of the distal top such that it is aligned with a rectangular transparent portion, or window, of the distal top. Additionally, a proximal and distal transparent portion, or window, of the distal top aligned with the proximal and distal ends of the indicator strip, respectively. The proximal window facilitates visual observation of the presence of sufficient fluid sample application onto the indicator strip, whereas the distal window facilitates visual observation of distal pad of the strip such that it can readily be determined if the fluid front reached the distal end of the strip and saturated the strip. Using 3M's MP 2.3 mil. adhesive transfer tape, the thus-formed distal top/indicator strip element is adhered to the top surface of the indicator housing such that the indicator strip is positioned within the second hole (rectangular cutout) of the indicator housing thereby creating a sealed internal volume housing the indicator strip.

The outer-facing surface of the distal top or the exterior of the outer casing is printed with graphics indicating the function of the device. For example, a graduated scale or other type of positional indicator to determine the position of the fluid front is used to determine whether the sample contains a threshold level of the analyte, or an unmarked window could be used such that if flow stops within a section of the medium visible through the window, it would indicate that the threshold concentration has been reached. A calibration curve is prepared with known amounts (i.e., standards) of analyte in order to determine what the threshold concentration of analyte is for the strip. The device can then be adjusted (e.g., by varying microbead concentration and placement, polymer concentration, antibody concentration) until the desired threshold concentration is achieved at the desired position on the indicator strip. If the device is to be used for quantitative measurements of analyte, the markings would be concentration units in the relevant range. Other labeling may provide general information.

Example 2

Non-Convergent Pathway Device Assembly

This example describes the assembly of an exemplary device that can be used for qualitative or quantitative analysis of a component of a sample fluid based on comparison of flow rates of the fluid in modified and unmodified paths. A non-convergent pathway, or split-flow, device is similar in design to a stopped-flow device, varying only in three aspects: (1) sample would be introduced at the center of the linear indicator strip (2) the hole in the proximal housing, which houses the vertical pad and allows sample introduction, is oriented perpendicular to the linear indicator strip, as opposed to inline with the indicator strip (3) the vertical conduit is rectangular as opposed to being circular or semicircular.

The device is assembled using components and specifications as described herein. In an exemplary embodiment, an assembled device is oblong or rectangular in shape with left and right ends and a semicircle protrusion extending proximally from the midpoint of the device. The dimensions of the device are 5.0 inches (from left to right)×1.58 inches (from proximal to distal when measured at its longest point). The outer housing of the exemplary device is a rigid material (specifically, acrylonitrile butadiene styrene (ABS), Snow White; Lustran 348-012002) that is solid on the bottom of the device and has an orifice on the top of the device for application of a fluid sample into a proximal well. Seven separate physical elements are adhered in a layered format to generate a device which can then be assembled into an outer housing made of ABS. The elements thus assembled create within the device a fluid pathway as follows: a proximal well for receiving a fluid sample which is in fluid communication with a volumetric capillary reservoir for transfer of the sample to the underside of a vertical conduit via a distal exit orifice, and a point of contact between the top of the vertical conduit and a central portion of a porous medium referred to as an indicator strip. In particular embodiments of the device, the porous medium is rectangular in shape.

A portion of the top of the exterior surface of the device is a transparent solid material for viewing the position of the two fluid fronts they migrate from the central point of introduction towards both ends of the porous medium. For example, in a particular embodiment, the window is rectangular in shape positioned above a segment of the indicator strip. This transparent window in the housing facilitates visualization of the fluid fronts. Additional portions of the top of the exterior surface may also be a transparent solid material such as, for example, one or more windows positioned above a location(s) on the indicator strip that provide(s) a visual indication of successful migration of fluid into the porous medium. A detailed description of the components of the device and assembly thereof follows.

A. Proximal Bottom

The proximal bottom is a solid, thin, rigid material having an outer surface and an inner surface. Specifically, Rigid Poly Vinyl Chloride is used to construct the proximal bottom at a thickness of 0.01 inch. All shapes can be produced using an Allen Datagraph template maker (Allen Datagraph Systems, Inc., Derry, N.H., U.S.A.). Parts can be designed in a computer-aided design (CAD) program, then "printed" by the template maker, which cut sheets of plastic into the desired shapes. The outer surface of the proximal bottom provides the outer-facing, solid base of the device, whereas the opposite, or inner, surface provides the inner-facing bottom of the device. The main body of the proximal bottom is 1.0" by 5.0", but in addition has a bulge to one side at the center of the long side, which adds an additional 0.58" in width. This bulge accommodates the volumetric capillary reservoir. The inner-facing bottom serves as a bottom of a volumetric capillary reservoir as well as provides a surface for the fluid sample to be applied. The fluid sample application area of the inner surface of the proximal bottom can be coated with substances (e.g., a mild 0.3% Tween-20® solution) to promote migration of fluid into the volumetric capillary reservoir. If the sample fluid is blood, the sample application area can be coated with a 20 µl solution of 70% ethanol containing 195 U/ml of Heparin sodium salt (to inhibit clotting of the blood sample).

B. Proximal Housing

The proximal housing is a thin, rigid material. Specifically, two sheets of Rigid Poly Vinyl Chloride are used to construct the proximal housing at a total thickness of 0.02 inch. The size and shape of the proximal housing are the same as those of the proximal bottom. There is a hole in the proximal housing in the shape of a 0.88 inch long center to center tear drop with the 0.5 inch diameter wide end of the tear drop positioned proximally compared to the position of the 0.12 inch diameter narrow end of the tear drop. This hole is positioned to have its long axes perpendicular to the axis of the indicator strip, such that the small end of the tear drops is positioned directly under the center of the indicator strip. The proximal housing is adhered to the proximal bottom using 3M's 467 MP 2.3 mil. adhesive transfer tape (3M, St. Paul, Minn.). Once adhered to the proximal bottom, the edges of the hole in the proximal housing provide the walls of a volumetric capillary reservoir and set the volume for the reservoir at 0.002 cubic inches (33 µl). The wide, circular end of the tear drop shape of the reservoir also serves as the fluid delivery reservoir. The edges of the reservoir and the portion of the proximal cover that caps the volumetric capillary reservoir can together be coated with a substance (e.g., a mild 0.3% Tween-20® solution) to promote migration of fluid into the volumetric capillary reservoir.

C. Proximal Cover

The proximal cover is a thin, rigid material. Specifically, Rigid Poly Vinyl Chloride is used to construct the proximal cover at a thickness of 0.01 inch. The proximal cover is the same size as the rectangular portion of the proximal housing and proximal bottom (5 inches×1 inch). The proximal housing does not include the semicircle protrusion, or central bulge, on the proximal side. There is one hole in the proximal cover. The hole is elliptical in shape measuring 0.06 inches (at its widest point; from left to right)×0.19 inches (at its widest point; proximal to distal) and is positioned in the middle of the proximal cover. The proximal cover is adhered to the proximal housing 3M's 467 MP 2.3 mil. adhesive transfer tape such that the elliptical hole is positioned over the wide, circular end of the tear drop shape of the reservoir formed by the proximal housing. Once adhered, the proximal cover caps the volumetric capillary reservoir, leaving a elliptical opening for the fluid sample delivery reservoir. As mentioned above, the portion of the proximal cover that caps the volumetric capillary reservoir and edges of the reservoir can together be coated with a substance (e.g., a mild 0.3% Tween-20®) solution to promote migration of fluid into the volumetric capillary reservoir.

D. Vertical Conduit

The vertical conduit in one exemplary embodiment of the device is a glass fiber filter (e.g., Millipore AP25), capable of separating cells from fluid (i.e., plasma or serum) in a vertical orientation. The vertical conduit is rectangular in shape and measures 0.13 inch×0.25 inch. The vertical conduit is adhered to the proximal cover using 3M's 467 MP 2.3 mil. adhesive transfer tape and situated directly above the distal exit orifice. The vertical conduit is positioned perpendicular to the plane of the housing. The distal orifice controls fluid flow such that fluid can enter the indicator housing only via capillary action of the indicator strip and, therefore, is unable to flow around and avoid being properly resolved within the indicator strip.

E. Vertical Conduit Housing

The vertical conduit housing is a thin, rigid material. Specifically, two sheets of Rigid Poly Vinyl Chloride are used to construct the proximal cover at a total thickness of 0.02 inch. The vertical conduit housing is the same size as the proximal cover (5 inches×1 inch). There is one hole in the vertical conduit housing. The hole is circular measuring 0.50 inches in diameter and is positioned in the middle of the vertical conduit housing to accommodate the vertical conduit. The vertical conduit housing is adhered to the proximal cover using 3M's 467 MP 2.3 mil. adhesive transfer tape so that the central hole lines up with the central hole on the proximal cover.

F. Indicator Housing

The indicator housing is a thin, rigid material. Specifically, Rigid Poly Vinyl Chloride is used to construct the indicator housing at a thickness of 0.04 inch. The size and shape of the indicator housing are the same as those of the proximal cover. There is one hole in the indicator housing. The hole is in rectangular measuring 4.52 inches (from left to right)×0.53 inches (proximal to distal) and is positioned in the middle of the proximal cover. The indicator housing is adhered to the vertical conduit housing 3M's 467 MP 2.3 mil. adhesive transfer tape. In positioning the indicator housing in this way, the vertical conduit is located in, and perpendicular to the plane of, the center of the rectangular cutout such that the fluid flow through the vertical conduit is perpendicular to the plane of the indicator housing. The indicator housing provides a minimal internal volume around the porous media components. This prevents humidity and other environmental variables from affecting fluid migration characteristics in the device.

G. Indicator Strip

The indicator strip is a lateral flow porous membrane made of Whatman LF1 (a 247 µm-thick, PVA-treated glass fiber paper that retains particles larger than 2 µm; Whatman, N.J., U.S.A.). The strip is rectangular in shape, following the shape of the indicator housing. The strip measures 3.93 inches (from left to right)×0.04 inches (from proximal to distal). The thickness of the indicator strip varies along its length from left to right, with the thickest portion set in the middle of the device. The thickest middle portion of the strip measures 0.25 inches thick and occupies the 0.97 inch (1.19 inches including tapered ends) center portion of the strip. The remainder of the strip flanks the thick portion and measures 0.04 inches thick.

Using 3M's 467 MP 2.3 mil. adhesive transfer tape, the indicator strip is adhered to the bottom surface of the distal top which, as described herein, also forms the top of the device with its outer, top surface. Thus, the strip is pressed to the underside of the roof of the device so that the strip is sandwiched between the roof of the device and the backing. The distal top, with the indicator strip and its backing adhered to its bottom surface, is adhered using 3M's 467 MP 2.3 mil. adhesive transfer tape to the indicator housing such that the indicator strip is positioned within large oval hole of the indicator housing thereby creating a sealed internal volume housing the indicator strip. The indicator strip is thus contained in a space wherein the bottom, or floor, of the space provided by the vertical conduit housing serves as a base for the strip, the hole in the indicator housing provides the walls of the space around the strip and the bottom surface of the distal top provides the roof of the space. Optional pads can be included at the far left and right ends of the indicator strip to provide a sink to collect excess sample fluid in the event that capillary flow of the fluid is not stopped in the indicator strip.

In some embodiments of the device, 2 µl of a solution prepared by solubilizing dry bromophenol blue (BPB) into 95% ethanol at 10 mg/ml [weight-to-volume (w/v)] can be applied onto the center of the far left and right pads of the indicator strip and allowed to dry for 5 minutes. The blue color provides a visual indicator that fluid migrated to the left and right pad of the indicator strip, indicating saturation of the strip.

H. Distal Top

The distal top is a thin rigid material. Specifically, Rigid Poly Vinyl Chloride is used to construct the distal top at a thickness of 0.01 inch. The size and shape of the distal top are the same as those of the indicator housing. One surface of the distal top forms the top of the device facing the exterior. Using 3M's 467 MP 2.3 mil. adhesive transfer tape, the indicator strip is adhered to the opposite (or bottom) surface of the distal top such that it is aligned with a long thin rectangular transparent portion, or window, of the distal top. Semicircle notches were cut out at 1.85 inches from the left on the distal side and at 3.15 inches from the left on the proximal side to allow for proper alignment of the filter paper. Using 3M's 467 MP 2.3 mil. adhesive transfer tape, the thus-formed distal top/indicator strip element is adhered to the top surface of the indicator housing such that the indicator strip is positioned within the hole of the indicator housing thereby creating a sealed internal volume housing the indicator strip.

The outer-facing surface of the distal top is printed with graphics indicating the function of the device. For example, a graduated scale or other type of positional indicator to determine the position of the fluid front for each arm of the strip is used to determine whether the sample contains a threshold level of the analyte, or an unmarked window could be used such that if flow stops within a section of the medium visible through the window, it would indicate that the threshold concentration has been reached. A calibration curve is prepared with known amounts (i.e., standards) of analyte in order to determine what the threshold concentration of analyte is for the strip. The device can then be adjusted (e.g., by varying microbead concentration and placement, polymer concentration, antibody concentration) until the desired threshold concentration is achieved at the desired position on the indicator strip. If the device is to be used for quantitative measurements of analyte, the markings would be concentration units in the relevant range. Other labeling may provide general information.

Example 3

Convergent Pathway Device Assembly

This example describes the assembly of exemplary convergent pathway devices that can be used for qualitative or quantitative analysis of a component of a sample fluid based on comparison of migration distances (and thus, indirectly, a comparison of flow rates) of the fluid in modified and unmodified paths. The devices are assembled using components and specifications as described herein. The outer housing of an exemplary device is a rigid material that is solid on the bottom of the device and has an orifice on the top of the device for application of a fluid sample into a proximal well. In an exemplary embodiment, an assembled device is rectangular in shape with rounded proximal and distal ends (see, e.g., FIGS. 9A and 9B). The dimensions of the device are 5.3 inches by 1.5 inches (12.5 cm by 2.5 cm). Seven separate physical elements are adhered in a layered format to generate the assembled device which can then be assembled into an outer housing. The elements thus assembled create within the device a fluid pathway as follows: a proximal well for receiving a fluid sample which is in fluid communication with a volumetric capillary reservoir for transfer of the sample to the underside of a vertical conduit via a distal exit orifice, and a point of contact between the top of the vertical conduit and a proximal portion of a ring of porous medium referred to as an indicator dial. In particular embodiments of the device, the ring of porous medium is oval (e.g., egg-shaped) or in the shape of a racetrack (i.e., having two parallel straight segments joined at each end by a rounded semicircle). In other embodiments of the device, the indicator dial is replaced with a linear rectangular indicator strip.

The exterior surface of an exemplary device is a rigid material (specifically, acrylonitrile butadiene styrene (ABS), Snow White; Lustran 348-012002 (Proto Labs)) that is solid on the bottom of the device and has an orifice on the top of the device for application of a fluid sample into a proximal well. A portion of the top of the exterior surface is a transparent solid material for viewing the convergence of fluid fronts moving in opposite directions around the convergent pathways. For example, in a particular embodiment, the window is in the shape of a horseshoe positioned above a distal half of an oval-shaped indicator dial. In another embodiment, the window is rectangular in shape positioned above a straight segment of a racetrack-shaped indicator dial. This transparent window in the housing facilitates visualization of the interface at which the two separate fluid fronts migrating through each arm of the indicator dial converge. Additional portions of the top of the exterior surface may also be a transparent solid material such as, for example, one or more windows positioned above a location(s) on the indicator dial that provide(s) a visual indication of successful migration of fluid into the porous medium. A detailed description of the components of the device and assembly thereof follows.

A. Proximal Bottom

The proximal bottom of the device is a solid, thin, rigid material having an outer surface and an inner surface (see, e.g., FIG. 12). Specifically, Rigid Poly Vinyl Chloride is used to construct the proximal bottom at a thickness of 0.01 inch. All shapes are produced using an Allen Datagraph template maker (Allen Datagraph Systems, Inc., Derry, N.H., U.S.A.). Parts are designed in a computer-aided design (CAD) program, then "printed" by the template maker, which cut sheets of plastic into the desired shapes. The outer surface of the proximal bottom provides the exterior solid base of the device, whereas the opposite, or inner, surface provides the interior bottom of the device. The inner surface of the proximal housing serves as a bottom closure of a volumetric capillary reservoir as well as provides a surface for the fluid sample to be applied. In some embodiments of the device, the fluid sample application area of the interior of the proximal bottom is coated with a substance to pre-treat the fluid in order to facilitate its migration. For example, if the fluid sample is blood, the sample application area may be coated with, for instance, a 20 µl solution of 70% ethanol containing 195 U/ml of Heparin sodium salt (to inhibit clotting of the blood sample) and a mild 0.3% Tween-20® solution to promote migration of blood into the volumetric capillary reservoir.

B. Proximal Housing

The proximal housing is a thin, rigid material. Specifically, Rigid Poly Vinyl Chloride is used to construct the proximal housing at a thickness of 0.02 inch. The size and shape (i.e., length and width) of the proximal housing are the same as those of the proximal bottom (see, e.g., FIG. 12). There is a hole in the proximal housing in the shape of a 0.576 inch long center to center tear drop with the 0.5 inch diameter wide end of the tear drop positioned proximally compared to the position of the 0.12 inch diameter narrow end of the tear drop. The proximal housing is adhered to the proximal bottom using 3M's 467 MP 2.3 mil. adhesive transfer tape (3M, St. Paul, Minn.). Once adhered to the proximal bottom, the edges of the hole in the proximal housing provide the walls of a volumetric capillary reservoir and set the volume for the reservoir at 0.002 cubic inches (33 µl). The wide, circular end of the tear drop shape of the reservoir also serves as the fluid delivery reservoir. Thus, the proximal housing sets the volume for the volumetric capillary reservoir and directs the sample fluid to the distal exit of the capillary reservoir. In some embodiments of the device, the edges of the reservoir are coated with a substance to pre-treat the fluid sample. For example, the edges of the reservoir may be coated with a mild Tween-20® solution to promote migration of the sample fluid to the distal exit of the reservoir. In some instances, when the fluid sample is blood, the edges of the reservoir and the portion of the proximal cover that caps the volumetric capillary reservoir are together coated with a 10 µl solution of 70% ethanol containing 195 U/ml Heparin sodium salt to inhibit clotting of the blood sample and a mild 0.3% Tween-20® solution to promote migration of blood into the volumetric capillary reservoir.

C. Proximal Cover

The proximal cover is a thin, rigid material. Specifically, Rigid Poly Vinyl Chloride is used to construct the proximal cover at a thickness of 0.01 inch. The size and shape (i.e., length and width) of the proximal cover are the same as those of the proximal housing (see, e.g., FIG. 12). There are two holes in the proximal cover. One hole is circular in shape measuring 0.5 inches in diameter and is positioned proximally with respect to the second hole, which is 0.125 inches in diameter. The proximal cover is adhered to the proximal housing 3M's 467 MP 2.3 mil. adhesive transfer tape such that the larger, proximal, circular hole is positioned over the wide, circular end of the tear drop shape of the reservoir formed by the proximal housing. Once adhered, the proximal cover caps the volumetric capillary reservoir, leaving a circular opening for the fluid sample delivery reservoir. The smaller, distal circular hole in the proximal cover provides the distal exit orifice of the volumetric capillary reservoir. The distal exit orifice is sized and located to promote capillary wicking of sample fluid into the vertical conduit. As mentioned above, the portion of the proximal cover that caps the volumetric capillary reservoir and edges of the reservoir can be coated with substances to promote migration of the fluid sample into and through the volumetric capillary reservoir.

D. Vertical Conduit

The vertical conduit is a porous material. Specifically, in an exemplary embodiment, the vertical conduit can be a glass fiber filter such as, for example, Millipore AP25 glass fiber filters with binder resin with the following specifications: 2.0 μm pore size; 1200 μm thickness; 5.8 mL/min/cm$^2$ water flow rate; 35 mm of H$_2$0 @ 10.5 fpm or 5.3 cm/s air resistance; 63.6 L/min/cm$^2$ @ 10 psi air flow; 0.03% DOP penetration at 10.5 FPM; 110 μg/cm$^2$ protein binding; and 140 g/m$^2$ weight (Millipore, Billerica, Mass.). The shape of the vertical conduit is either a 3/16 inch diameter circle or semicircle depending on whether the indicator dial is oval or racetrack-shaped, respectively. The circular or semicircular shape is used in order to make the distance from any point on the distal edge of the vertical conduit and the proximal edge of the resolving region of the indicator dial consistent (see, e.g., FIG. 13). This design promotes passage of the fluid front from the vertical conduit and into the indicator dial such that it converges at the resolving region of the indicator dial. The vertical conduit is adhered to the proximal cover using 3M's 467 MP 2.3 mil. adhesive transfer tape and situated directly above the distal exit orifice. The vertical conduit is positioned perpendicular to the plane of the housing. The distal orifice controls fluid flow such that sample fluid can enter the indicator housing only via capillary action of the indicator dial and, therefore, is unable to flow around and avoid being properly resolved within the indicator dial (i.e., the fluid is constrained to flow thorough the indicator dial). When used with blood samples, the vertical conduit may have the additional function of filtering red blood cells (which could interfere with reading of the indicator dial) from plasma.

E. Indicator Housing

The indicator housing is a thin, rigid material. Specifically, Rigid Poly Vinyl Chloride is used to construct the indicator housing at a thickness of 0.04 inch. The size and shape (i.e., length and width) of the indicator housing are the same as those of the proximal cover (see, e.g., FIG. 12). There are two holes in the indicator housing. One hole is circular in shape measuring 0.5 inches in diameter and is positioned proximally with respect to the second hole. The second hole is either oval in shape or racetrack-shaped, depending on whether the indicator dial is oval or racetrack-shaped, respectively. For one embodiment of the device, the oval is circular and the hole is 4.5 cm in diameter. The size of the hole is determined be the size of the indicator dial contained within the hole. The size of the indicator dial is determined based on the range of concentration being measured or INR values being tested and the rate of flow of the fluid around the indicator dial. To calculate the circumference of the strip, tests are performed to determine how far (and therefore how much time) samples must travel to achieve the greatest resolution between concentrations of a specific analyte or INR value (within a determined acceptable timeframe). However far the furthest migrating sample runs on average, that distance is doubled to calculate the total circumference. The distance is doubles because the competitive flow from each direction will travel at or near the same rate for the fastest migrating sample and therefore will meet halfway around the strip. The indicator housing is adhered to the proximal cover using 3M's 467 MP 2.3 mil. adhesive transfer tape such that the circular proximal hole in the housing is positioned directly above the circular proximal hole in the proximal cover. In positioning the indicator housing in this way, the vertical conduit is located in, and perpendicular to the plane of, the distal oval (or race-track shaped) hole in the indicator housing. The indicator housing provides a minimal internal volume around the indicator dial components. This prevents humidity and other environmental variables from affecting fluid migration characteristics in the device.

F. Indicator Dial

The indicator dial is a porous material that in an exemplary embodiment of the device is situated such that fluid flows laterally through it (see, e.g., FIGS. 10, 11, 13). In a particular embodiment, the indicator dial is made of thin glass fiber material. Specifically, LF1 glass fiber (Whatman, N.J., U.S.A.) is used. This is a polyvinyl alcohol-bound glass fiber filter that can remove particles greater than 2 μm. The indicator dial is a ring, and, in particular embodiments, is either oval or racetrack-shaped, corresponding to the shape of the second larger hole of the indicator housing. The outer dimensions of the indicator dial are typically between 4 and 15 cm in circumference, and most commonly 10 cm in circumference with a strip that is 2 mm wide. The shape of the indicator dial can be anywhere from circular to racetrack in shape where the two parallel side of the race track are nearly touching. Using 3M's 467 MP 2.3 mil. adhesive transfer tape, the indicator dial is adhered to the bottom surface of the distal top which, as described herein, also forms the top of the device with its outer, top surface. The distal top, with the indicator dial adhered to its bottom surface, is adhered using 3M's 467 MP 2.3 mil. adhesive transfer tape to the indicator housing such that the indicator dial is positioned within the distal second (oval or racetrack-shaped) hole of the indicator housing thereby creating a sealed internal volume housing the indicator dial. The indicator dial is thus contained in a space wherein the bottom, or floor, of the space provided by the proximal cover serves as a base for the dial, the distal second hole in the indicator housing provides the walls of the space around the dial, and the bottom surface of the distal top provides the roof of the space. A proximal portion of the indicator dial ring is situated above and in contact with the top of the vertical conduit which is adhered on the proximal cover. This design provides for fluid migration up from the underside of the vertical conduit and into the proximal end of the indicator dial. Upon entering the indicator dial, fluid migrates in both directions (clockwise and counter clockwise) around the arms of the indicator dial until the two fluid fronts converge at a point in the dial. At that point, saturation of the porous medium of the indicator dial is reached and no further fluid migration can occur.

Dyes can be included in the indicator dial material to facilitate visualization of the fluid fronts in the dial. In a particular embodiment of the device, bromophenol blue is included in the indicator dial. Dry bromophenol blue (BPB) is solubilized into 95% ethanol at 10 mg/ml [weight-to-volume (w/v)]. 2 μl of this solution is applied onto the indicator dial at one spot (located on either side of the point in the dial where fluid enters the dial from the vertical conduit) and was allowed to dry. The powdered dyes become visible upon contact with the sample fluid and make the point of convergence of the two fluid fronts easily visible.

In particular embodiments of the device, one arm of the indicator dial is treated to modify the rate of flow of the sample fluid in that arm relative to the rate of fluid flow in the other arm of the indicator dial. The treatment of an arm of the indicator dial is such that the rate of flow of fluid containing an analyte of interest will be modified in the arm in an analyte concentration-dependent manner. The treatment used in a particular device will vary based on the analyte being measured. Selection of a treatment and numerous examples of treatments are described herein. Further treatments can be determined empirically by those of skill in the art based on the teachings provided herein.

G. Distal Top

The distal top is a thin rigid material with areas of transparent material forming windows in the distal top. Specifically, Rigid Poly Vinyl Chloride is used to construct the indicator housing at a thickness of $10/1000^{th}$ of an inch per layer of Rigid Poly Vinyl Chloride. Graduations are marked on either the outer casing or the distal top. The distal top also contains two circular cut-out areas: one at the distal end and the other at the proximal end. The distal circular cut-out is an air escape opening allowing displaced air to escape as sample fluid is drawn into the device. The size of the air escape hole simply needs to be large enough to allow air to escape as volume within the device is displaced by liquid. In one embodiment, the air hole is $3/32$ in diameter. The proximal circular cut-out (0.5 inches in diameter) forms the orifice through which sample fluid is introduced into the volumetric capillary reservoir and is positioned directly above the circular proximal hole in the indicator housing.

The size and shape of the distal top are the same as those of the indicator housing (see, e.g., FIG. 12). One surface of the distal top forms the top of the device facing the outer casing. Using 3M's 467 MP 2.3 mil. adhesive transfer tape, the indicator dial is adhered to the opposite (or interior) surface of the distal top such that a portion of the indicator dial aligns with a portion of the distal top that aligns with the window on the outer casing. For a device having an oval indicator dial, the horseshoe-shaped distal half of the indicator dial ring aligns with a horseshoe-shaped transparent portion of the distal top. For a device having a racetrack-shaped indicator dial, the straight segment on the left of the dial aligns with a rectangular transparent portion of the distal top. A second transparent window in the distal top is circular, $1/8^{th}$ inches in diameter, and located between the fluid delivery well orifice and the horseshoe-shaped (or rectangular) transparent window. This circular window is positioned above the proximal edge of the indicator dial at or near the point where fluid enters the indicator dial from the vertical conduit. For embodiments of the device having a racetrack-shaped indicator dial, a second circular window is positioned distal to the distal end of the rectangular window. The circular windows facilitate visual observation of the presence of fluid sample reaching the proximal or distal ends of the indicator dial and thus inform the user when enough sample has been applied.

Using 3M's 467 MP 2.3 mil. adhesive transfer tape, the thus-formed distal top/indicator dial element is adhered to the top surface of the indicator housing such that the indicator dial is positioned within the distal hole of the indicator housing thereby creating a sealed internal volume housing the indicator dial. The horseshoe-shaped or rectangular transparent window in the distal top facilitates visualization of the point of convergence of the fluid fronts migrating around each arm of the indicator dial.

H. Calibration of an Exemplary Device

The outer-facing surface of the distal top or outer casing is printed with graphics indicating the function of the device. A graduated scale around the distal half of the circumference of the oval indicator dial, or on one or both of the long sides of the rectangular window, allows readout of the position of the convergence of the two fluid fronts. A calibration curve is prepared with known amounts or characteristics of the fluid variable being assayed (i.e., standards) in order to determine the positions on the indicator dial at which the two fluid fronts will converge for differing amounts or characteristics of the fluid variable. The device can then be adjusted (e.g., by varying concentration and/or placement of antibodies, microbeads, polymers and precipitating agents) until the fluid front convergence positions for differing amounts/characteristics of a fluid variable are achieved at the desired locations on the indicator dial. If the device is to be used for quantitative measurements of analyte, the markings would be, for example, concentration units in the relevant range. Other labeling can provide general information.

Example 4

Analyte Effects on Fluid Flow Rate in Porous Media

In this example, fluid samples containing an analyte (neutravidin) were tested for migration distance using a linear lateral flow device as described below.

A. Device Assembly

A set of six linear lateral flow devices was assembled to assess the migration distances of fluid samples in the presence or absence of analyte. The devices were similar to the device described in Example 1, with the exception that these devices did not possess an outer housing. A 20 mm wide master lateral flow strip was first assembled as described below, and 2 mm wide individual strips were subsequently cut from the master strip. The master strip components were assembled against a standard lateral flow backing (PVC sheet with adhesive coating on one side). From proximal to distal, the lateral flow materials were: (1) 20 mm borosilicate glass fiber filter paper with a PVA binding (Ahlstrom 8975) (2) 15 mm blocked nitrocellulose membrane (VIVID™ 170; Pall), and (3) 47 mm PVA-treated glass fiber filter paper (Whatman LF1). Prior to assembly, the nitrocellulose membrane (VIVID™ 170; Pall) was blocked with 1 mg/ml neutravidin in PBS for 1 hour at room temp, washed 2× for 5 minutes in PBS, rinsed 2× with $H_2O$, and dried overnight at room temperature. Materials were laid down with the second component (VIVID™ 170; Pall) being first pressed against the adhesive backing, with its own backing in contact with the device backing. The first (Ahlstrom 8975) and third (Whatman LF1) components were subsequently laid down such that they flanked the second component (VIVID™ 170; Pall) with 2 mm of overlap over each end of the second (VIVID™ 170; Pall) component. Additionally, the first component (Ahlstrom 8975) was laid down such that a portion of the material was left to overhang from the adhesive backing on the proximal end of the master strip by 5 mm.

A total of six 2 mm wide individual strips were then cut from the 20 mm wide master strip and built into individual devices using components described in Example 1. The 2 mm wide strips were pressed to the underside of the roof of the device such that the strip materials were sandwiched between the roof of the device and the backing. Assembled devices contained a $3/16$ inch diameter polyethylene pad (POR-4897; POREX®) that formed a bridge between the capillary reservoir and the overhung proximal end of the first strip component (Ahlstrom 8975).

B. Sample Migration Test

In this example, fluid samples containing an analyte (neutravidin) were tested for migration distance using the devices described in part A of this example. The fluid samples were prepared by adding neutravidin (Pierce) or PBS to a master mix of dyed latex beads and LPA-biotin in PBS.

The LPA-biotin used in these experiments was synthesized according to the following protocol. The reaction below was set up in a 15-ml screw-capped tube: 16 µl 20% APMA, 984 µl 20% acrylamide, 952 µl $dH_2O$, 40 µl 10% APS and 8 µl TEMED. This was mixed well and incubated static at room temperature for 2 hours. 4.0 ml dH$_2$O was added and subsequently mixed with a 1-ml pipet, attempting to achieve a fairly uniform suspension. Mixing was continued on a rotating/oscillating platform until a uniform suspension was achieved (approx 4-6 h). 4-6 ml of the LPA-NH$_2$ suspension was transferred to dialysis tubing and dialyzed 2 times against 1.8 L dH$_2$O in a 2 L beaker (with stirring) at room temperature overnight for the first dialysis and for 2-4 hrs for the second. The LPA-NH$_2$ was recovered from the dialysis tubing and transferred to a 15-ml screw-capped tube. Basic amine concentration was then determined using a Ninhydrin Assay.

The biotinylation of LPA-NH$_2$ was achieved using the following protocol. A reaction was set up containing 1.2 ml LPA-NH$_2$ (approx. 1.7 µM NH$_2$), 112 µl 500 mM Na$_2$HPO$_4$, 8.16 µl 500 mM NaH$_2$PO$_4$, and 16.7 µl 2 mg/ml sulfo-NHS-LC-biotin (suspended in water immediately prior to addition to reaction). This reaction was mixed well then incubated at 4° C. overnight. Following the overnight incubation, the remaining amines were capped with acetic anhydride as follows: the pH of reaction was adjusted to ~7.0 by adding NaH$_2$PO$_4$; the solution was chilled in an ice water bath, then three 2-µl aliquots of neat acetic anhydride were added at 15 min intervals with mixing after each addition. The biotinylation/acetic anhydride reaction products were dialyzed against dH$_2$O using a Pierce 20,000 MWCO Slide-A-Lyzer dialysis cassette (using Pierce's recommended protocol).

Following the synthesis of LPA-biotin, a sample master mix was prepared by mixing 15 µl of a 1% slurry in PBS of 53 nm dyed latex beads (Bangs Labs; Cat #DS02B/8692), 15 µl of a 1% slurry in PBS of 120 nm dyed latex beads (Bangs Labs; Cat #DS02B/9112), 15 µl of 14.7 µM LPA-biotin in PBS and 155 µl of PBS (200 µl total). 80 µl of the master mix was aliquoted into two tubes. Each tube was spiked with either 20 µl PBS or 20 µl of 1 mg/ml neutravidin in PBS, mixed 3× quickly, and immediately pipetted onto the test strip device via the sample port, or proximal well, of the device. Migration distances of the fluid front were recorded over time and compared. Tests were performed in triplicate. Mean migration distance and standard deviation were calculated for each time point. The results are presented in TABLE 3 below.

TABLE 3

Sample Migration Test

| Time (min) | Mean Migration Distance (mm) n = 3 | | | |
|---|---|---|---|---|
| | −neutravidin | std dev | +neutravidin | std dev |
| 0 | 0 | 0 | 0 | 0 |
| 0.08 | 10.17 | 0.29 | 8.17 | 2.57 |
| 0.17 | 17.50 | 2.29 | 15.67 | 1.61 |
| 0.25 | 21.33 | 1.04 | 20.33 | 0.29 |
| 0.5 | 25.67 | 0.29 | 26.33 | 1.53 |
| 0.75 | 29.00 | 0.00 | 28.67 | 0.58 |
| 1 | 32.17 | 0.29 | 30.00 | 0.00 |
| 1.5 | 35.83 | 0.58 | 34.33 | 0.76 |
| 2 | 40.17 | 0.29 | 36.00 | 1.00 |
| 3 | 45.17 | 1.89 | 40.50 | 3.97 |
| 4 | 51.33 | 0.58 | 42.67 | 5.06 |
| 5 | 56.33 | 3.79 | 44.17 | 5.97 |
| 6 | 62.00 | 2.00 | 45.5 | 6.50 |
| 7 | 67.33 | 3.79 | 46.33 | 6.66 |
| 8 | 72.00 | 5.20 | 47.33 | 7.18 |
| 9 | 73.67 | 2.31 | 47.33 | 7.18 |
| 10 | 75.00 | 0.00 | 47.33 | 7.18 |
| 15 | 75.00 | 0.00 | 49.83 | 8.81 |
| 20 | 75.00 | 0.00 | 49.83 | 8.81 |

The results of this experiment show that samples lacking neutravidin migrated farther than the samples containing neutravidin. These results were observed at all time points after two minutes. The migration distances measured before two minutes showed little variation. Thus, the presence of an analyte in a fluid sample was reproducibly detected based on cessation of fluid migration on the test strip.

Example 5

Viscosity Effects on Fluid Flow Rate in a Porous Medium

The following example describes an experiment conducted to demonstrate how fluid viscosity differences can affect fluid flow rates in a porous membrane and to demonstrate how this principle can be used as a basis of measuring the ability of a blood sample to coagulate.

A. Device Assembly

Strips were constructed using a single linear piece of porous filter paper (Ahlstrom 8975) cut to 2 mm by 80 mm. The strips were pressed to the underside of the roof of the device. For each assembled device, a 3/16 inch diameter thromboplastin-treated polyethylene pad (POR-4897; POREX®) was affixed to the device such that the disk formed a bridge between the capillary reservoir and the overhung proximal end of the strip material (Ahlstrom 8975). Prior to assembly, each POREX® pad was treated with 20 µl of a 20% glycerol/ 2× thromboplastin DS (Fisher Scientific Cat#292273DEM) solution and dried overnight at room temperature.

B. Plasma Migration

In this experiment, the migration distances of human blood plasma samples with reported international normalized ratios (INRs) were measured at various time points after application of the samples to the linear porous strip device described in part A.

Commercially available INR control plasmas (Fisher Scientific Cat#23-029-227) were prepared according to manufacturer's instructions. INR samples of 1.0, 1.1, 2.3, and 4.0 were tested using the linear test strips described above. For each INR plasma sample, 900 µl of the plasma sample was mixed with 100 µl of a 2.59% slurry of 200 nm dyed latex beads (Polysciences Cat#15706). 80 µl of this mix was applied to each device and migration distances were recorded. Ten linear strip tests per INR sample were performed. The following table presents mean migration distances of samples and standard deviations for each INR at time points between 0 and 240 seconds.

TABLE 4

Plasma Migration

| Time (sec) | Mean Migration Distance (mm) n = 10 | | | | | | | |
|---|---|---|---|---|---|---|---|---|
| | INR 1.0 | std dev | INR 1.1 | std dev | INR 2.3 | std dev | INR 4.0 | std dev |
| 0 | 0 | 0 | 0 | 0 | 0 | 0 | 0 | 0 |
| 5 | 7.60 | 0.57 | 7.6 | 1.29 | 8.15 | 2.14 | 9 | 1.58 |
| 10 | 13.05 | 1.01 | 12.8 | 1.99 | 13.7 | 2.90 | 14.35 | 1.92 |
| 15 | 17.85 | 1.55 | 17.75 | 2.18 | 18.1 | 3.36 | 18.5 | 2.00 |
| 20 | 22.15 | 1.27 | 22 | 2.61 | 22.15 | 4.44 | 22.8 | 1.99 |
| 30 | 28.25 | 1.62 | 29 | 3.04 | 28.05 | 5.12 | 29.5 | 2.21 |
| 45 | 28.75 | 2.07 | 31.45 | 2.63 | 35.3 | 5.56 | 37.35 | 2.42 |
| 60 | 28.75 | 2.07 | 31.45 | 2.63 | 39.45 | 4.59 | 45.1 | 2.51 |
| 75 | 28.75 | 2.07 | 31.45 | 2.63 | 41.2 | 3.58 | 51.1 | 3.07 |
| 90 | 28.75 | 2.07 | 31.45 | 2.63 | 41.65 | 3.59 | 54.75 | 3.00 |
| 120 | 28.75 | 2.07 | 31.45 | 2.63 | 41.65 | 3.59 | 55.35 | 3.10 |
| 240 | 28.75 | 2.07 | 31.45 | 2.63 | 41.65 | 3.59 | 55.35 | 3.10 |

This experiment showed that plasma samples with higher INR values consistently migrated farther than samples with lower INRs. This occurred because samples with higher INR values have longer coagulation times, and thus migrated farther before a coagulation-induced slowing occurred due to the increased viscosity of the coagulated plasma relative to uncoagulated plasma. The resolution of migration distances between samples was apparent at 45 seconds with complete resolution observed at 120 seconds. Thus, it was possible to properly distinguish samples with different coagulation properties within the range of INRs tested and within 120 seconds based on migration distance through a porous test strip.

The beads and dye used in these experiments aided in the visualization of the fluid front. For example, the beads migrated with the fluid front. However, a small amount of dye also was included to help visualize the actual fluid. After an extended period of time (i.e. 30 minutes or more), serum would trickle out beyond the plasma front where the beads had stopped in some samples. This serum was the color of the dye since the beads were still contained within the plasma clot.

The INR samples above were further analyzed for coagulation properties using a standard visual test. Specifically, 30 µl of each INR sample at 37° C. was pipetted into a sample tube. 60 µl of 37° C. Thromboplastin-DS (ISI of 1.0) was forcibly dispensed into the tube then gently pipetted. Clotting time was determined visually or based on when the fluid became resistant to pipetting (whichever was observed first). Five tests per INR sample were performed. INR values were calculated based on mean coagulation times (prothrombin times) and using the formula for INR calculation below:

$$INR = \left(\frac{PT_{test}}{PT_{normal}}\right)^{ISI}$$

Where:
$PT_{test}$=Prothrombin Time (measured)
$PT_{normal}$=Normal Prothrombin Time (control)
ISI=International Sensitivity Index (an empirical constant provided by the manufacturer)

The calculated mean INR values for each sample were compared to the plasma migration results above. TABLE 5 below presents mean coagulation times (3$^{rd}$ column from the left) and respective mean calculated INRs (2$^{nd}$ column from the left) for the standard test, and presents mean distances where samples arrested on the porous test strips (3$^{rd}$ column from the right).

TABLE 5

Plasma Migration vs. Coagulation Time

| | Standard Test (n = 5) | | | | Migration in Porous Strip (n = 10) | | |
|---|---|---|---|---|---|---|---|
| Reported INR | Calc. INR | Mean Time | Std Dev | CV (%) | Mean Distance (mm) | Std Dev | CV (%) |
| 1.0 | 1.0 | 16.8 | 0.84 | 4.98 | 28.75 | 2.07 | 7.21 |
| 1.1 | 1.2 | 19.0 | 0.71 | 3.72 | 31.45 | 2.63 | 8.36 |
| 2.3 | 2.3 | 34.0 | 1.0 | 2.94 | 41.65 | 3.59 | 8.62 |
| 4.0 | 3.7 | 49.6 | 2.41 | 4.86 | 55.35 | 3.10 | 5.60 |

This experiment showed that migration distances of plasma in a porous strip are proportional to coagulation times measured using a standard visual assay. Specifically, samples with longer coagulation times consistently generated longer migration distances. Thus, the measurement of plasma flow in a porous medium was able to generate predictable results for the assessment of plasma coagulation properties.

Example 6

Projected Viscosity Effects on Fluid Flow Rate in a Convergent Flow Porous Medium The following example describes an experiment conducted to demonstrate how fluid viscosity differences can affect fluid flow rates in a linear porous membrane and how data obtained from a linear flow device can be used to predict convergent migration values on a circular flow device.

A. Device Assembly

Strips were constructed using a single linear piece of PVA-treated glass fiber paper (Whatman LF1) cut to 2 mm by 100 mm. The strips were pressed to the underside of the roof of the device such that the strip material was sandwiched between the roof of the device and the backing. For each assembled device, a ³⁄₁₆ inch diameter thromboplastin-treated polyethylene pad (POR-4897; POREX®) was affixed to the device such that the disk formed a bridge between the capillary reservoir and the overhung proximal end of the strip material (Whatman LF1). Prior to assembly, each POREX® pad was treated with 20 µl of a 2× thromboplastin DS (Fisher Scientific Cat#292273DEM) solution and dried overnight at room temperature.

B. Plasma and Serum Migration

In this experiment, the migration distances of human blood plasma samples with known coagulation properties were measured at various time points after application of the samples to the linear porous strip device described in part A.

Healthy plasma (Fisher Scientific Cat#176198), coagulation impaired plasma (Fisher Scientific Cat#176214) and serum (no clotting ability) samples were tested using the linear test strips described above. For each sample, 900 µl of the plasma or serum sample was mixed with 100 µl of a 2.59% slurry of 200 nm dyed latex beads (Polysciences Cat#15706). 80 µl of this mix was applied to each device and migration distances were recorded. Three linear strip tests per plasma or serum sample were performed. The following table presents mean migration distances of samples and standard deviations for each sample at time points between 5 and 900 seconds (not all time points were recorded for all samples).

TABLE 6

Plasma and Serum Migration

| | | Mean Migration Distance (mm) n = 3 | | | | |
|---|---|---|---|---|---|---|
| Time | | Healthy | std | Coag-impaired | std | | std |
| sec | √sec | Plasma | dev | Plasma | dev | Serum | dev |
| 5 | 2.24 | 9.2 | 0.29 | 10.8 | 1.04 | 9.8 | 1.26 |
| 10 | 3.16 | | | | | 14.5* | 0.71 |
| 15 | 3.87 | 14.5 | 0.00 | 17.8 | 3.33 | 18.3* | 2.47 |
| 30 | 5.48 | 19.8 | 1.53 | 26.5 | 1.80 | 25.2 | 1.44 |
| 45 | 6.71 | | | 32.0 | 1.80 | 31.3 | 2.02 |
| 60 | 7.75 | 24.8 | 1.76 | 35.7 | 1.76 | 36.0 | 1.73 |
| 120 | 10.95 | 30.8 | 2.36 | 44.2 | 0.76 | 50.3 | 2.93 |
| 180 | 13.42 | 35.7 | 2.75 | 51.2 | 1.76 | 61.8 | 2.02 |
| 240 | 15.49 | 40.5 | 3.50 | 55.8 | 1.44 | 71.5 | 3.04 |
| 300 | 17.32 | 43.8 | 3.55 | 60.7 | 3.25 | | |
| 360 | 18.97 | 46.3 | 4.04 | 67.3* | 3.18 | | |
| 420 | 20.49 | 50.3 | 5.03 | 70.3 | 2.34 | | |

TABLE 6-continued

Plasma and Serum Migration

Mean Migration Distance (mm) n = 3

| Time | | Healthy | std | Coag-impaired | std | | std |
|---|---|---|---|---|---|---|---|
| sec | √sec | Plasma | dev | Plasma | dev | Serum | dev |
| 480 | 21.91 | | | 74.5* | 2.12 | | |
| 540 | 23.24 | 56.5 | 5.07 | 73.8* | 1.06 | | |
| 600 | 24.49 | 59.2 | 5.62 | | | | |
| 660 | 25.69 | 61.3 | 6.43 | | | | |
| 720 | 26.83 | 61.3* | 7.42 | | | | |
| 780 | 27.93 | 62.5* | 7.78 | | | 76.5* | 0.71 |
| 840 | 28.98 | 67.2 | 8.04 | | | | |
| 900 | 30.00 | 68.7 | 8.50 | | | | |

*The calculated mean migration distance was based on the results of two tests.

As expected, the serum samples with no clotting ability migrated faster along the test strip than the plasma samples. Conversely, the healthy plasma samples (with the best clotting ability) were slower to migrate along the test strip than the other samples. By 240 seconds (4 minutes), for example, the healthy plasma samples had migrated an average of 40.5 mm, the coagulation impaired plasma samples had migrated an average of 55.8 mm, and the serum samples had migrated an average of 71.5 mm.

C. Predicting Migration Times and Distances on a Convergent Flow Device

The migration time and distance data for plasma and serum samples presented above was obtained using a linear flow device. This data was converted to hypothetical results for circular, or convergent flow, strips using a straightforward graphical approach. It was assumed that the position of the liquid front along a linear strip with time corresponded to the position along an arm in a circular strip. The presumed point of convergence between the two arms of the circular strip (treated and untreated) was found by plotting, on the same graph, both the front position versus time along a treated linear strip, and the circumference of the strip minus the front position versus time along an untreated linear strip. The point of convergence of these two plots yielded both the expected position of the front convergence along the treated arm, and the expected time that this convergence occurred. In this case, the serum data represented migration along an untreated arm. We assumed the circumference of the circular strip was 110 mm, thus the position of the serum front was subtracted from 110 mm. This is shown graphically in FIG. 15. The intersections show that healthy plasma migrating along the treated arm would be expected to converge with the untreated arm at approximately 40 mm along the treated arm after approximately 225 seconds, while impaired plasma would converge at a point 50 mm along the treated arm after approximately 169 seconds.

Figure 14:
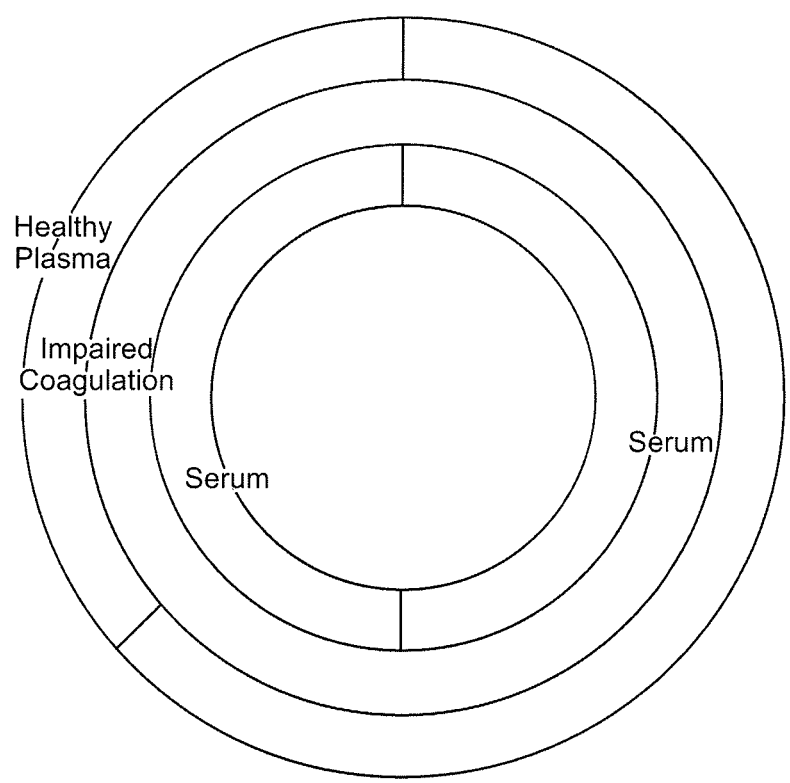

Thus, data obtained using a linear flow strip can be used to predict the point of convergence on a circular, or convergent flow, device. A graphical illustration of the predicted points of convergence between the plasma and serum samples on a 110 mm Whatman LF1 circle is presented in FIG. 14.

Example 7

Viscosity Effects on Fluid Flow Rate in a Convergent Flow Porous Medium

The following example describes an experiment conducted to demonstrate how fluid viscosity differences can affect fluid flow rates in a convergent flow device. Specifically, this example shows how coagulation activity correlates with the point of convergence on a ring shaped porous medium.

A. Device Assembly

Strips were constructed using a single linear piece of PVA-treated glass fiber paper (Whatman LF1) adhered to a Rigid Poly Vinyl Chloride backer and cut using an Allen Datagraph template maker (Allen Datagraph Systems, Inc., Derry, N.H., U.S.A.) to 3 mm by 130 mm. The backed strips were pressed to the underside of the roof of the device such that backing was pressed against the roof of the device. A section of each strip (3 mm in length) was cut and removed at the most proximal point on the circle. For each assembled device, two 3/16 inch diameter polyethylene pads (POR-4897; POREX®) were affixed to the device such that the disk formed a bridges between the capillary reservoir and the two proximal ends of the strip material (Whatman LF1) that were created upon cutting a section of the strip out. Prior to assembly, one of the two POREX® pads was treated with 20 µl of a 2x thromboplastin DS (Fisher Scientific Cat#292273DEM) solution and dried overnight at room temperature. The capillary reservoir was designed so that it forks at the distal end to lead to two holes that feed up to the undersides of the treated and untreated polyethylene pads. The entire device was 8 cm in length by 5.5 cm wide and constructed consistent with standard methods described within this patent. Bromophenol blue (amounting to less than 1 mg) was spotted one quarter of the way around the strip on the arm leading from the untreated porex pad.

B. Plasma and Serum Migration

In this experiment, the migration distances of human blood plasma samples with known coagulation properties were measured at various time points after application of the samples to the circular porous strip device described in part A.

Healthy plasma (Fisher Scientific Cat#176198) and serum (no clotting ability) samples were tested using the circular test strips described above. For each sample, 135 µl of the plasma or serum sample was mixed with 15 µl of a 2.59% slurry of 200 nm dyed latex beads (Polysciences Cat#15706). The entire volume (150 µl) of this mixture was applied to each device via the sample port, or proximal well, and allowed to flow up through the sample channel to the proximal left and right pads of the circular strip. An even flow of fluid from the channel to both the left and right pads was qualitatively observed. Migration distances were recorded at various time points for each arm of the circular strip. Two circular strip tests per serum sample were performed and three circular strip tests per healthy plasma sample were performed. The following table presents migration distances of samples at time points between 0 and 180 seconds.

TABLE 7

Plasma and Serum Migration in a Convergent Flow Device

| | Migration Distance (mm) | | | | | | | | | |
|---|---|---|---|---|---|---|---|---|---|---|
| | Healthy Plasma 1 | | Healthy Plasma 2 | | Healthy Plasma 3 | | Serum 1 | | Serum 2 | |
| Time (sec) | Lt arm | Rt arm | Lt arm | Rt arm | Lt arm | Rt arm | Lt arm | Rt arm | Lt arm | Rt arm |
| 0 | 0 | 0 | 0 | 0 | 0 | 0 | 0 | 0 | 0 | 0 |
| 30 | 34 | 39 | 36 | 41 | 35 | 35 | 39 | 38 | 39 | 36 |
| 60 | 43 | 47 | 45 | 55 | 44 | 49 | 52 | 52 | 51 | 51 |
| 90 | 47 | 58 | 51 | 63 | 47 | 57 | 61 | 60 | 62 | 61 |
| 120 | 55 | 66 | 55 | 69 | 52 | 67 | 66 | 64 | 64 | 66 |
| 180 | 47 | 83 | 51 | 79 | 55 | 75 | 66 | 64 | 64 | 66 |

As expected, the serum samples with no clotting ability migrated with equal speed along each arm of the circular test strip. The two fluid fronts converged at the 180° point of the circular strip. Conversely, the healthy plasma samples (with normal clotting ability) were slower to migrate along the treated arm (left side) of the circular test strip. Thus, in all three cases of healthy plasma, the point of convergence of the two fluid fronts was left of the 180° point of the circular strip.

Example 8

Effects of Immunochemically-Modified Beads on Fluid Flow Rate in Porous Media

The following example describes an assay which uses a modified linear test strip device. In particular, this device has been modified to cause the agglutination of immunochemically-modified microbeads in the presence of the analyte, thereby modifying the flow rate in response to the concentration of the analyte.

A. Device Assembly

A set of eight linear lateral flow devices was assembled to assess the migration distances of fluid samples in the presence or absence of analyte. A 20 mm wide master lateral flow strip was first assembled as described below, and 2 mm wide individual strips were subsequently cut from the master strip. The master strip components were assembled against a standard lateral flow adhesive backing (PVC sheet with adhesive coating on one side). From proximal to distal, the lateral flow materials were: (1) 20 mm 20 mm borosilicate glass fiber filter paper with a PVA binding (Ahlstrom 8975), (2) 7 mm blocked nitrocellulose membrane (VIVID™ 170; Pall), and (3) 60 mm glass fiber matrix material (Whatman FUSION 5™). Prior to assembly, the nitrocellulose membrane (VIVID™ 170; Pall) was blocked with 1 mg/ml neutravidin in PBS for 1 hour at room temp, washed 2× for 5 minutes in PBS, rinsed 2× with $H_2O$, and dried overnight at room temperature. Materials were laid down with the second component (VIVID™ 170; Pall) being first pressed against the adhesive backing, with its own backing in contact with the device backing. The first (Ahlstrom 8975) and third (Whatman FUSION 5™) components were subsequently laid down such that they flanked the second component (Vivid 170; Pall) with 1 mm of overlap over each end of the second (VIVID™ 170; Pall) component. Additionally, the first component (Ahlstrom 8975) was laid down such that a portion of the material was left to overhang from the adhesive backing on the proximal end of the master strip by 5 mm. The entire length of the strip was 80 mm.

A total of eight 2 mm wide individual strips were then cut from the 20 mm wide master strip and built into individual devices using Rigid Poly Vinyl Chloride as described in Example 1. The 2 mm wide strips were pressed to the underside of the roof of the device such that the strip materials were sandwiched between the roof of the device and the backing. Assembled devices contained a 3/16 inch diameter polyethylene pad (POR-4897; POREX®) that formed a bridge between the capillary reservoir and the overhung proximal end of the first strip component (Ahlstrom 8975).

B. Modification of Linear Device

Prior to the application of samples to the test strip devices described above, the devices were modified by the addition of agents which affect flow rate by causing the agglutination of immunochemically-modified microbeads and linear polyacrylamide in response to the concentration of a specific analyte. In this example, the analyte was C-reactive protein (CRP) and the modification was the addition of anti-CRP antibody coated beads, biotin-conjugated anti-CRP antibodies, and LPA-biotin to the POREX® pad of the device.

The anti-CRP antibody coated beads were generated as follows: 50 µl of a 10% slurry of 53 nm polystyrene beads were combined with 143 µl of rabbit anti-CRP antibody (10 mg/ml), 2.5 µl of 10% tween-20, 254.5 µl of $H_2O$, and 50 µl of 10×PBS. 50 µl of a 10% slurry of 120 nm polystyrene beads were combined with 60 µl of rabbit anti-CRP antibody (10 mg/ml) and 2.5 µl of 10% tween-20, 287.5 µl of $H_2O$, and 50 µl of 10×PBS. Beads were mixed overnight at 4° C., dialyzed 3× against 1000 ml of PBS+0.02% tween-20, and stored in 1 mg/ml BSA PBS+0.02% tween-20.

To set up experiments, 15 µl of LPA-biotin (414.7 µM; synthesized as described in Example 4) was mixed with 30 µl of neutravidin (1 mg/ml) and mixed on a thermomixer at 1200 rpm for 5 minutes at 30° C. 15 µl of mouse anti-hCRP antibody (5 mg/ml) was subsequently introduced and mixed another 10 minutes. 4.5 µl of each size bead-bound antibody (the 53 nm and 120 nm beads described above) was mixed with 4 µl of the LPA-biotin-neutravidin-antibody mix and 0.5 µl of red dye. 13 µl of this mixture was applied to the device and allowed to soak into the POREX® pad that sits between the capillary reservoir and the linear test strip.

C. CRP Sample Migration

After waiting 30 seconds, the sample was loaded via the sample port, or proximal well. Each sample contained either 100 µl of 60 ng/ml hCRP (AbD Serotec Cat#1707-2029) in 1 mg/ml BSA in PBS or 100 µl of 1 mg/ml BSA in PBS. Migrations of the samples were analyzed over time. A total of four tests were performed for each sample type. The following table presents mean migration distances of samples and standard deviations for each sample type at time points between 0.8 and 35 minutes.

To compare multiple tests, each pair of tests was normalized against the final migration point of the −CRP sample (at 35 minutes). Percent relative migration of all four +CRP and −CRP samples were then analyzed statistically. Mean percent relative migration values and standard deviations were calculated and are presented in the table below.

TABLE 8

Migration of CRP Samples

| Time (min) | Mean Migration Distance (mm) n = 4 | | | | Mean % Relative Migration | | | |
|---|---|---|---|---|---|---|---|---|
| | +CRP | std dev | −CRP | std dev | +CRP | std dev | −CRP | std dev |
| 0.08 | 16 | 0.00 | 15.75 | 0.96 | 31 | 10 | 30 | 8 |
| 0.17 | 18.5 | 0.58 | 18.5 | 1.00 | 33 | 12 | 33 | 11 |
| 0.25 | 20 | 0.00 | 20 | 0.00 | 36 | 12 | 36 | 12 |
| 0.5 | 21.25 | 0.50 | 22.25 | 0.96 | 38 | 13 | 40 | 14 |
| 0.75 | 22.5 | 0.58 | 23.25 | 0.96 | 41 | 15 | 42 | 15 |
| 1 | 23.5 | 0.58 | 24 | 0.82 | 42 | 15 | 43 | 15 |
| 1.5 | 25.25 | 1.50 | 26.25 | 0.50 | 45 | 16 | 47 | 16 |
| 2 | 26.75 | 1.50 | 28.25 | 0.96 | 48 | 17 | 51 | 17 |
| 3 | 28.75 | 1.89 | 31.75 | 1.71 | 51 | 16 | 57 | 17 |
| 4 | 30.75 | 3.77 | 34.75 | 3.30 | 54 | 15 | 61 | 15 |
| 5 | 33.25 | 5.68 | 37 | 4.24 | 58 | 12 | 65 | 15 |
| 6 | 34.75 | 7.32 | 38 | 5.35 | 59 | 10 | 66 | 14 |
| 7 | 36 | 8.76 | 39 | 6.38 | 61 | 8 | 67 | 12 |
| 8 | 36.75 | 9.07 | 39.25 | 6.65 | 62 | 8 | 68 | 12 |
| 9 | 37.5 | 9.98 | 40 | 7.53 | 63 | 7 | 69 | 11 |
| 10 | 39.25 | 10.05 | 41.5 | 7.59 | 67 | 11 | 71 | 13 |
| 12 | 40.75 | 10.44 | 43 | 9.31 | 69 | 10 | 73 | 11 |
| 15 | 43.25 | 12.15 | 47.25 | 12.42 | 73 | 10 | 80 | 8 |
| 20 | 44.75 | 13.33 | 51.25 | 14.73 | 75 | 11 | 86 | 6 |
| 25 | 47 | 13.34 | 55.5 | 17.94 | 79 | 8 | 92 | 6 |
| 30 | 48.5 | 15.07 | 59 | 20.85 | 81 | 7 | 97 | 4 |
| 35 | 48.75 | 15.37 | 60.75 | 20.56 | 81 | 6 | 100 | 0 |

Individual pairs of samples consistently showed the +CRP sample migrated slower than the −CRP sample, though inter-test variability remained high. To remove such inter-test variability from the analysis, percent relative migration was calculated which showed consistently lower relative migration for the +CRP sample. Thus, the presence of CRP presumably caused a measureable agglutination of the immunobeads within the test strip device, resulting in slower migration through the porous test strip. The increased viscosity of the sample, caused by LPA, also presumably modified the flow rate.

Example 9

Modification of Fluid Flow by Effectively Decreasing Porosity or Permeability of a Porous Medium A. Precipitation (1) Addition of Enzymes and/or Substrates One example of flow-modifying agents would be a set of enzymes and substrates that in the presence of the analyte form a precipitate that blocks the pores of the media, thus restricting flow. One example of the use of precipitation to change flow rate can be demonstrated by an assay to measure glucose in a sample material. In this immediate embodiment, enzymes glucose oxidase and horseradish peroxidase can be bound to a region of a test strip. In a convergent flow embodiment, the unmodified arm will lack glucose oxidase and HRP. The sample can be mixed in a known ratio with a substrate such as 3,3'-Diaminobenzidine (DAB) and the sample applied to the test strip. As the sample migrates toward and through the region with the immobilized enzymes, the glucose contained within the sample will react with the glucose oxidase producing hydrogen peroxide and d-Gluconic Acid. In turn, the hydrogen peroxide and the DAB will react with the horseradish peroxidase to produce an insoluble brown-black precipitate that will serve to locally decrease the pore size of the support membrane thus decreasing the local flow rate. This change in flow rate can then be measured and related directly to the quantity of glucose present in the sample. The quantity of the precipitating material is proportional to the quantity of the glucose present in the sample, thus more glucose present would result in more precipitate forming thus slowing the flow of the liquid fraction of the sample more. It is also possible to have only one of the enzymes immobilized and have the other mixed with the sample traveling through the test strip, the goal being for a precipitate to form in a localized region of the membrane thus affecting the flow rate. In addition, the process could be performed simply by mixing the substrate and the sample directly with the enzymes so that precipitate will form in a non-localized fashion but still serve to decrease the pore size of the membrane and affect flow rates. Persons skilled in the art will recognize that many other types of analysis could be performed using this process the requirements being that a precipitate can be caused to form, the quantity of this precipitate being proportional to the quantity of the analyte to be measured and that this precipitate can affect the flow rate of the liquid portion of the sample through the membrane. Other potential substrate systems include but are not limited to combining alkaline phosphatase with the commonly known substrate pair BCIP/NBT.

(2) Immobilization of Analyte and Enzyme

In yet another example, localized formation of a precipitate can be caused by antibody binding in a localized area of a test strip that a liquid sample can migrate through. In a preferred embodiment intended to measure C-Reactive Protein (CRP) in a sample, two antibodies designated a1 and a2 that can bind to a CRP molecule or molecular complex can be employed. Antibody a1 can be associated either covalently or non-covalently with an enzyme such as horseradish peroxidase. The second antibody a2 can be unmodified or modified with a molecule such as biotin. In this embodiment, a sample suspected of containing CRP can be mixed with antibody a1, glucose and a precipitating substrate such as 3,3'-Diaminobenzidine (DAB). A region of the test strip will have antibody a2 and glucose oxidase bound either specifically or non-specifically to a region distal to the point of sample application. The sample will then migrate through the prepared test strip such as a nitrocellulose or nylon membrane, CRP bound antibody a1 will be retained by binding to antibody a2 causing an increase in the localized concentration of glucose oxidase in a dose responsive manner. Binding of CRP-bound antibody a1 to antibody a2 serves to increase glucose oxidase concentration by causing it to be retained in a specific area of the strip, therefore increasing the local concentration. In a convergent flow embodiment of the device, the unmodified arm will lack one or all of the components necessary for the precipitation reaction. Membrane bound glucose oxidase will react with glucose added to the sample producing hydrogen peroxide, in turn, the hydrogen peroxide will react with the peroxidase labeled antibody a1 and DAB forming an insoluble precipitate that will affect the flow rate of the liquid fraction of the sample in a dose responsive manner. This change in flow rate can be measured to determine the concentration of CRP in the sample. It is noted that unbound antibody a1 will also cause the formation of precipitate however due to the transient nature of this antibody presence, the quantity and rate of formation will simple contribute to a reasonable constant rate of precipitate formation that will be reasonable consistent from sample to sample. Those skilled in the art will recognize that many different targets can be measured using this approach, the major requirements being that antibody binding cause the formation of a precipitate that can affect flow rate of the liquid fraction of a sample in a manner proportional to the amount of antibody binding. In addition, those skilled in the art will recognize that this system can be used in a competitive binding fashion where the presence of analyte in the sample will compete with added target analyte to cause a decrease in binding to a localized area of the test strip causing a decrease in the localized formation of a precipitate to form thus increasing the flow rate of the liquid portion of the sample in a manner inversely proportional to concentration of target in a sample. In addition, those skilled in the art will recognize that antibody a2 may be biotinylated or labeled with some other specific capture label and a specific capture moiety such as a biotin binding protein such as avidin, neutraavidin or streptavidin bound to the test strip enabling both antibodies (a1, a2) to be added to the sample and the entire complex captured, but only antibody a2 captured in a dose responsive manner. Those skilled in the art will recognize that there are many ways to capture antibodies that include but are not limited to His tag, species specific anti-antibodies, Protein A and Protein G in addition to many others. Other potential substrate systems include but are not limited to combining alkaline phosphatase with the commonly known substrate pair BCIP/NBT.

B. Use of Microbeads to Effectively Decrease Pore Size of a Medium

There are several possible means to use micro-sized polystyrene beads combined with immunochemistry principles to change porosity/permeability of the porous media. The change in flow rate provides an inversely proportional indication of target analyte concentration within a sample. Accumulation of beads within the void volume of a porous membrane such as lateral flow papers (Fusion 5, Whatman) or nitrocellulose membranes (Vivid) serves to attenuate flow of the applied sample by changing the effective porosity and permeability. Precise accumulation of beads can be achieved through the application of specific molecular recognition elements such as antibodies, proteins, nucleic acids and their derivatives targeting a desired analyte. Immobilization of beads at a desired segment on the membrane will cause a change in sample flow rate on a test strip designed for a specific target. The combination of reagents and materials described in this procedure provide a rapid, analyte specific, semi-quantitative test to measure solutes such as protein, nucleic acids, and metabolites from biological samples. Several approaches can be used to accentuate bead localized membrane pore blocking and reduce sample flow in response to a target analyte. One of these is to combine the obstruction of membrane pores by bead accumulation with enzyme mediated precipitation reactions directed by bead localization. In this instance, the combination of beads coated with enzymes or antibody enzyme fusions can be used to generate localized precipitates in the presence of specific target analytes. The combination of a non-uniform localized precipitate formation and bead accumulation would very effectively generate a reduction in sample flow rate. The presence of very small precipitates would complement pore blocking by beads as localized precipitation would plug remaining gaps due to variations in membrane pore size that are left open by beads. Alternatively, the incorporation of water soluble polymers alone or in combination with beads or enzymes would also serve to reduce flow rates in proportion to the target analyte concentration. These polymers could be used as non-specific blocking reagents or be functionalized with molecular recognition elements to add specificity to bead accumulation or precipitate formation reaction. Polymers could be conjugated or fused to bead surfaces or enzymes to add shape and create a more non-uniform blocking agent to restrict flow. The added non-uniform volume of the polymers would work in the same vein as precipitation formation to plug remaining gaps not blocked by beads due to varying membrane pore size and more effectively reduce sample flow rates.

Example 10

Modification of Fluid Flow by Effectively Increasing Viscosity of a Fluid

A. Agglutination

An alternative version of this type of assay uses the agglutination of beads within a sample to prevent or decrease flow of a sample on a test strip. Using the CRP example above, a sample is mixed with a1 and a2 antibodies to CRP adhered to beads. The sample is then applied to a porous lateral flow membrane strip. If the sample contains CRP, the beads will agglutinate, plug the void volume, and create a barrier preventing or slowing entry of the sample into the membrane. In the absence of CRP, the beads remain dispersed throughout the sample and allow sample flow into the membrane. The agglutination of beads at the sample addition site effectively reduces pore size and the available space for fluid flow within the test strip. The degree of agglutination and quantity of beads accumulated at this segment of the test strip is directly proportional to the amount of CRP in the sample. Thus, the flow rate of sample and beads into the test strip is a direct indicator of CRP concentration within the sample. As above, the migration of colored indicator beads provides a direct correspondence to the migration of liquid sample into the strip and presence of target analyte. Similarly, beads may also be non-spherical modified shapes, functionalized with different surface chemistries, or combined with other mechanisms to affect flow rate within a porous membrane. The addition of non-specific beads (beads not bound to a molecular recognition element) can be used to cause a further reduction in flow rate generated from protein coated beads specifically recognizing a target analyte and effectively amplify the signal. It is also possible to have antibody coated beads on a sample or reagent pad that precedes the immobilized neutravidin segment and are taken up by the sample as it flows through the test strip. Experts familiar with lateral flow and other immunological techniques with recognize that many other types of analysis can be performed with this method. The essential aspect of this assay is the specific accumulation of beads within the flow matrix resulting in a proportional decrease in flow rate due to the reduction in void volume available for sample flow.

Agglutination of suspended particles can slow flow rate by increasing the bulk viscosity of the fluid/particle mixture. Bulk viscosity of a mixture is proportional to particle diameter and mass fraction of the particles (Multiphase Flow and Fluidization: Continuum and Kinetic Theory Descriptions; Dimitri Gidaspow (Academic Press, 1994)). As particles agglutinate, they effectively become particles of larger diameter, without changing the mass fraction. If the extent of agglutination is dependent on analyte concentration, then flow rate will be dependent on analyte concentration.

B. Polymerization

There are several possible means to use immunochemically-modified polymers (in the presence or absence of micro-particles) combined with immunochemistry principles to change the flow characteristics through a porous medium. In all cases, analyte in the sample serves as a bridge either to cross-link polymer to polymer, or polymer to micro-particle. The cross-links are due to the formation of the classical sandwich complex formed in many immunoassays, in which the analyte is bound by two different antibodies which are linked to two different polymer molecules or micro-particles. As the polymers become more highly cross-linked with each other in the presence of analyte—either directly, or through micro-particles as intermediaries—the viscosity of the fluid increases, slowing flow. If the extent of cross-linking is high enough, a gel will form, leading to cessation of flow.

If the two antibodies bind to different epitopes on the analyte to form a sandwich complex, then these antibodies will be different, denoted ab1 and ab2. If only polymer is used in this device, then one scheme would be to conjugate ab1 to one preparation of polymer, and ab2 to another preparation of polymer. These two preparations of polymer could then be mixed in different ratios in order to tune the system to be responsive to different concentration ranges of analyte. In another polymer-only scheme, the antibodies ab1 and ab2 could be conjugated in different ratios to the same preparation of polymer, so that all polymer chains could potentially be conjugated with both ab1 and ab2. Any combination of the above schemes could also be used to form a gel or mesh that would stop flow.

Micro-particles coated with ab1 or ab2 or both could be added to any of the above polymer-only schemes, or appropriated preparations of antibody-coated micro-particles could replace an analogous preparation of polymer in any of the above schemes. In general, micro-particles will have different effects on flow rate than polymers. Captured or immobilized particles can affect flow rates by changing the effective porosity, pore size, and/or permeability of the porous medium. Gels or meshes which are formed by the combination of polymer and micro-particles will behave differently than gels or meshed formed by polymers alone.

REFERENCES CITED

O'Farrell B (2009). "Evolution in lateral-flow based immunoassay systems" in *Lateral Flow Immunoassay*, R C Wong and H Y Tse, editors. Humana Press, New York.

Brown M C (2009). "Antibodies: key to robust lateral-flow assays" in *Lateral Flow Immunoassay*, R C Wong and H Y Tse, editors. Humana Press, New York.

Rosen S (2009). "Market trends in lateral-flow immunoassays" in *Lateral Flow Immunoassay*, R C Wong and H Y Tse, editors. Humana Press, New York.

Washburn E W (1921). "The dynamics of capillary flow." *The Physical Review* 17:3 pp 273-283.

Batchelor G K (1967). *An Introduction to Fluid Dynamics*. The University Press, Cambridge.

Lambert P (2007). *Capillary Forces in Microassembly*. Springer Science, New York.

Nield D A (2002). "Modeling fluid flow in saturated porous media and at interfaces" in *Transport Phenomena in Porous Media II*. D B Ingham and I Pop, editors. Pergamon Press (Elsevier Science).

Nield D A, Bejan A (1992). *Convection in Porous Media*. Springer-Verlag.

McCabe W L, Smith J C, Harriot P (1985). *Unit Operations of Chemical Engineering*. 4$^{th}$ Edition. McGraw-Hill Book Company.

Qian S, Bau H H (2003). "A mathematical model of lateral flow bioreactions applied to sandwich assays". *Analytical Biochemistry*. 322 pp 89-98.

Bird R B, Stewart W E, Lightfoot E N (1960). *Transport Phenomena*. John Wiley and Sons.

The invention claimed is:

1. A method of determining the ability of a fluid variable to modify flow of a fluid, comprising:
   (a) applying the fluid to a medium comprising converging flow paths, wherein the fluid flows into each of the converging flow paths;
   (b) measuring the point of convergence of the fluid fronts in the flow paths; and
   (c) determining a change in the fluid variable that corresponds to modification in the flow of the fluid in one of the flow paths based on a change in the point of convergence of said fluid fronts;
   wherein:
   (i) one of the flow paths has been modified such that flow of the fluid in the modified flow path changes in proportion to the change in the fluid variable;
   (ii) one of the flow paths has not been modified; and
   (iii) the point of convergence of the fluid fronts in the converging flow paths proportionally corresponds to the change in the fluid variable; and
   (iv) the fluid variable comprises
      1) viscosity of the fluid.

2. The method of claim 1, wherein the fluid variable further comprises an amount or concentration of an analyte in the fluid.

3. The method of claim 2, further comprising determining the amount or the concentration of the analyte in the fluid based on the change in the point of convergence due to said modification of said flow path.

4. The method of claim according to claim 1, wherein the fluid is a solution comprising a biological molecule or a biological fluid.

5. The method of claim 4, wherein the biological fluid is selected from blood, plasma, serum, urine, saliva, seminal fluid, lavages, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof.

6. The method of claim 4, wherein the biological molecule is selected from proteins and nucleic acids.

7. The method of claim 1, wherein the medium is selected from porous or non-porous materials, or combinations thereof.

* * * * *